US011965006B2

(12) United States Patent
Deslouches et al.

(10) Patent No.: US 11,965,006 B2
(45) Date of Patent: *Apr. 23, 2024

(54) ANTIMICROBIAL AND ANTI-CANCER THERAPY

(71) Applicant: UNIVERSITY OF PITTSBURGH—OF THE COMMONWEALTH SYSTEM OF HIGHER EDUCATION, Pittsburgh, PA (US)

(72) Inventors: Berthony Deslouches, Pittsburgh, PA (US); Yuanpu Di, Wexford, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/531,100

(22) Filed: Nov. 19, 2021

(65) Prior Publication Data

US 2022/0195001 A1  Jun. 23, 2022

Related U.S. Application Data

(63) Continuation of application No. 16/462,586, filed as application No. PCT/US2017/062837 on Nov. 21, 2017, now Pat. No. 11,286,287.

(60) Provisional application No. 62/551,571, filed on Aug. 29, 2017, provisional application No. 62/424,697, filed on Nov. 21, 2016.

(51) Int. Cl.
*C07K 14/47* (2006.01)
*A61K 38/00* (2006.01)

(52) U.S. Cl.
CPC .......... *C07K 14/4723* (2013.01); *A61K 38/00* (2013.01)

(58) Field of Classification Search
None
See application file for complete search history.

(56) References Cited

U.S. PATENT DOCUMENTS

| 7,985,832 B2 * | 7/2011 | Melgarejo ............... A61P 33/02 530/300 |
| 8,071,540 B2 | 12/2011 | Montelaro et al. |
| 11,286,287 B2 * | 3/2022 | Deslouches ........ C07K 14/4723 |
| 2002/0188102 A1 | 12/2002 | Montelaro et al. |
| 2015/0258172 A1 | 9/2015 | Jillman |

FOREIGN PATENT DOCUMENTS

| CN | 104497126 | 4/2015 |
| WO | 2008/085578 | 7/2008 |
| WO | 2013/039857 | 3/2013 |
| WO | 2014/152437 | 9/2014 |
| WO | 2016/044683 | 3/2016 |

OTHER PUBLICATIONS

Mullin (Fierce Biotech, 2014), downloaded online on Nov. 25, 2020 from URL:<http://www.fiercebiotech.com/r-d/ebola-outbreak-rages-on-as-drug-development-remains-slow> (Year: 2014).*
CIDRAP News, Nov. 18, 2003, downloaded online on Nov. 25, 2020 from URL:<http://www.cidrap.umn.edu/news-perspective/2003/11/nih-launches-first-human-trial-ebola-vaccine>(Year: 2003).*
Hersh et al., Clinical Infectious Diseases 2012;54(11 ):1677-8 (Year: 2012).*
Chang et al. (J Biol Chem. Jan. 2, 2012;287(1):418-428) (Year: 2012).*
Brook et al. (Radiation Research, 122, 215-217 (1990)) (Year: 1990).*
Wu et al. (Plos One 6(8): e23500, 2011) (Year: 2011).*
International Search Report and Written Opinion dated Mar. 20, 2018, from International Application No. PCT/ JS2017/062837, 18 pages.
Lee et al. "Interactions between the plasma membrane and the antimicrobial peptide HP (2-20) and its analogues derived from Helicobacter pylori", Biochemical Journal, Feb. 15, 2006, vol. 394, pp. 105-114.
Liu, Y. et al. "Increased susceptibility to pulmonary Pseudomonas infection in Splunc1 knockout mice", J Immunol 191. 4259-4268 (2013).
Liu, Y et al. "SPLUNC1/BPIFA1 contributes to pulmonary host defense against Klebsiella pneumoniae respiratory infection", Am J Pathol 182(5), 1519-1531 (2013).
Kenichiro, I. et al. "Mechanisms of secondary structure breakers in soluble proteins", Biophysics, vol. 1. pp. 55-65 (2005).
Communication Pursuant to Rule 164(1) EPC dated Mar. 27, 2020, from related EP application No. EP 17872709.5, 14 pages.
Extended European Search Report dated Jun. 29, 2020, issued in related EP application No. 17872709.5, 11 pages.
Luo et al. Front. Microbiol., Mar. 31, 2017.

(Continued)

*Primary Examiner* — Sergio Coffa
(74) *Attorney, Agent, or Firm* — Meunier Carlin & Curfman LLC

(57) ABSTRACT

This disclosure is directed to compositions comprised of antimicrobial peptides (AMPs) having an alpha helical structure wherein one side is highly hydrophobic. Representative sequences of the antimicrobial peptides include ILKKWWββαβGLLGβLLGαVββVIKβLββI (SEQ ID No. 2), LKKWWKβαKGLLGGLLGKVββVIK (SEQ ID No. 12), and αKKααKKαKGαLGGLαGK (SEQ ID No. 18). Additional embodiments disclose methods for treating a microbial infection; reducing biofilm; decreasing inflammation; and treating infectious diseases, COPD, asthma, pulmonary fibrosis, cystic fibrosis, rhinosinusitis, septicemia, RSV, TB or cancer; in a subject in need thereof comprising administering to the subject a therapeutic amount of an antimicrobial peptide.

11 Claims, 45 Drawing Sheets

Specification includes a Sequence Listing.

(56) References Cited

OTHER PUBLICATIONS

Martineau et al., J Immunol Jun. 1, 2007, 178 (11) 7190-7198.
Genscript (downloaded on Jun. 8, 2020 from URL:< https://www.genscript.com/peptide/RP13323-LL37 Human _. html>} (Year: 2020).
First Office Action, dated Apr. 28, 2022, received in connection with CN Patent Application No. 201780071830.5, including English translation, 12 pages.
European Examination Report filed in Application No. 178727095, dated Jul. 11, 2022, 5 pages.
Lijuan Zhang et al., Influence of Pronline Residues on the Antibacterial and Synergistic Activities of α-Helical Peptides, Biochemistry 1999, 38, 8102-8111.
Office Action issued in Chinese Application No. 201780071830.5, dated Jan. 18, 2023, 4 pages.
European Search Report filed in Application No. 23165171.2, dated Jul. 24, 2023, 15 pages.

\* cited by examiner

LL37 (SEQ ID No. 25)

WLBU2 (SEQ ID No. 26)

SEQ ID No. 1

Formula I

ANTIMICROBIAL AND ANTI-CANCER THERAPY

CROSS-REFERENCE TO RELATED APPLICATIONS

This is a continuation of U.S. application Ser. No. 16/462,586 which is a national stage application filed under 35 U.S.C. § 371 of PCT/US2017/062837 that claims priority to U.S. Provisional Application Nos. 62/551,571 filed Aug. 29, 2017 and 62/424,697 filed Nov. 21, 2016, the disclosures of which are expressly incorporated by reference in their entireties.

GOVERNMENT INTERESTS

This invention was made with government support under HL125128 and AI133351 awarded by the National Heart, Lung, and Blood Institute and National Institute of Allergy and Infectious Diseases, National Institutes of Health. The government has certain rights in the invention.

INCORPORATION-BY-REFERENCE OF MATERIAL SUBMITTED ELECTRONICALLY

Incorporated by reference in its entirety herein is a computer readable sequence listing submitted concurrently herewith and identified as follows: One 14.5 kilobytes ASCII (Text) file named "10504-032US1_2019_05_21_Sequence_Listing," created on May 2, 2019.

BRIEF SUMMARY

Described herein are a number of antimicrobial peptides (AMPs) derived from a short region of SPLUNC1 (short palate lung nasal epithelial clone 1), a protein that the innate immune system normally expresses in the respiratory apparatus. Embodiments herein are directed to a composition comprising an excipient and one or more AMPs having the helical amphipathic structure provided in formula I as shown in FIG. 33 wherein residues 1, 4, 5, 8, 11, 12, 15, and 16 are hydrophobic amino acids, and residues 2, 3, 6, 7, 9, 10, 13, 14, 17, and 18 are any non-hydrophobic or hydrophilic amino acids. In some embodiments, the hydrophobic amino acids are selected from the group consisting of the L or D form of the following: alanine, isoleucine, leucine, tryptophan, phenylalanine, valine, proline, and glycine. In some embodiments, the non-hydrophobic or hydrophilic amino acid is selected from the group consisting of the L or D form of the following: arginine, lysine, aspartic acid, glutamic acid, glutamine, asparagine, histidine, serine, threonine, tyrosine, cysteine, methionine, selenocysteine, and pyrrolysine.

In some embodiments, the composition may be used in a method of treatment for microbial infection, chronic obstructive pulmonary disease (COPD), asthma, pulmonary fibrosis, cystic fibrosis, rhinosinusitis, septicemia, Respiratory syncytial virus, Influenza virus, human immunodeficiency virus, human papilloma virus, human leukemia virus, herpes simplex virus, hepatitis A, B, and C viruses, parainfluenza viruses, rhinoviruses, coronaviruses, enteroviruses, adenoviruses, tuberculosis (TB), gonorrhea, *chlamydia, C. difficile, Borrelia burgdorferi* (Lyme disease), streptococci, *Listeria monocytogenes, Mycoplasma pneumonia, Haemophilus* Influenza, *Streptococcus pneumoniae, Moraxella catarrhalis*, or *Meningococcus meningitis*. In some embodiments, the microbial infection is selected from the group consisting of *Enterococcus faecium, Staphylococcus aureus* (including MRSA), *Klebsiella pneumonia, Escherichia coli,* Enterobacteriaceae, *Pseudomonas aeruginosa, Acinetobacter baumannii, Burkholderia* spp., Carbapenem-resistant Enterobacteriaceae, Respiratory syncytial virus, Influenza virus, human immunodeficiency virus, human papilloma virus, human leukemia virus, herpes simplex virus, hepatitis A virus, hepatitis B virus, hepatitis C virus, parainfluenza viruses, rhinoviruses, coronaviruses, enteroviruses, adenoviruses, tuberculosis (TB), gonorrhea, *chlamydia, C. difficile, Borrelia burgdorferi* (Lyme disease), streptococci, *Listeria monocytogenes, Mycoplasma pneumonia, Meningococcus meningitis, Haemophilus influenza, Streptococcus pneumoniae,* and *Moraxella catarrhalis*.

Some embodiments are directed to an AMP consisting of the sequence selected from the group consisting of ILKKWWββαβGLLGβLLGαVββVIKβLββI (SEQ ID No. 2), LKKWWKβαKGLLGGLLGKVββVIK (SEQ ID No. 12), αKKααKKαKGαLGGLαGK (SEQ ID No. 18), and RRWVRRVRRVWRRVVRVVRRWVRR (SEQ ID No. 26).

Some embodiments are directed to a method of treating a microbial infection in a subject in need thereof comprising administering to the subject a therapeutic amount of an AMP selected from the group consisting of ILKKWWββαβ-GLLGβLLGαVββVIKβLββI (SEQ ID No. 2), LKKWWKβαKGLLGGLLGKVββVIK (SEQ ID No. 12), αKKααKKαKGαLGGLαGK (SEQ ID No. 18), and RRWVRRVRRVWRRVVRVVRRWVRR (SEQ ID No. 26).

Some embodiments are directed to a method of reducing biofilm in a subject in need thereof comprising administering to the subject a therapeutic amount of an AMP selected from the group consisting of ILKKWWββαβGLLGβ-LLGαVβββVIKβLββI (SEQ ID No. 2), LKKWWKβαKGLLGGLLGKVβββVIK (SEQ ID No. 12), αKKααKKαKGαLGGLαGK (SEQ ID No. 18), and RRWVRRVRRVWRRVVRVVRRWVRR (SEQ ID No. 26).

Some embodiments are directed to a method of decreasing inflammation in a subject in need thereof comprising administering to the subject a therapeutic amount of an AMP selected from the group consisting of ILKKWWββββαβ-GLLGβLLGαVββVIKβLββI (SEQ ID No. 2), LKKWWKβαKGLLGGLLGKVββVIK (SEQ ID No. 12), αKKααKKαKGαLGGLαGK (SEQ ID No. 18), and RRWVRRVRRVWRRVVRVVRRWVRR (SEQ ID No. 26).

Some embodiments are directed to a method of treating chronic obstructive pulmonary disease (COPD), asthma, pulmonary fibrosis, cystic fibrosis, septicemia, or rhinosinusitis in a subject in need thereof comprising administering to the subject a therapeutic amount of an AMP selected from the group consisting of ILKKWWββαβGLLGβLLGαVββ-VIKβLββI (SEQ ID No. 2), LKKWWKββαKGLLGGLLG-KVββVIK (SEQ ID No. 12), αKKααKKαKGαLGGLαGK (SEQ ID No. 18), and RRWVRRVRRVWRRVVRVVRR-WVRR (SEQ ID No. 26).

Some embodiments are directed to a method of treating Respiratory syncytial virus (RSV) or tuberculosis (TB) in a subject in need thereof comprising administering to the subject a therapeutic amount of an AMP selected from the group consisting of ILKKWWββαβGLLGβLLGαVββ-VIKβLββI (SEQ ID No. 2), LKKWWKββαKGLLGGL-LGKVββVIK (SEQ ID No. 12), αKKααKKαKG-αLGGLαGK (SEQ ID No. 18), and RRWVRRVRRVWRR-VVRVVRRWVRR (SEQ ID No. 26).

Some embodiments are directed to a method of treating cancer in a subject in need thereof comprising administering to the subject a therapeutic amount of an AMP selected from the group consisting of ILKKWWββαβGLLGβLLGαVββ-

VIKβLββI (SEQ ID No. 2), LKKWWKβαKGLLGGL-LGKVββVIK (SEQ ID No. 12), αKKααKKαKGαLG-GLαGK (SEQ ID No. 18), and RRWVRRVRRVWRRVVR-VVRRWVRR (SEQ ID No. 26).

In some embodiments, α is a hydrophobic amino acid selected from the group consisting of the L or D form of the following: alanine, isoleucine, leucine, tryptophan, phenylalanine, valine, proline, and glycine. In some embodiments, β is a non-hydrophobic or hydrophilic amino acid selected from the group consisting of the L or D form of the following: arginine, lysine, aspartic acid, glutamic acid, glutamine, asparagine, histidine, serine, threonine, tyrosine, cysteine, methionine, selenocysteine, and pyrrolysine.

DESCRIPTION OF DRAWINGS

For a better understanding of the nature and advantages of the present invention, refer to the following detailed description taken in connection with the accompanying drawings, in which.

DETAILED DESCRIPTION

Figure 1A:
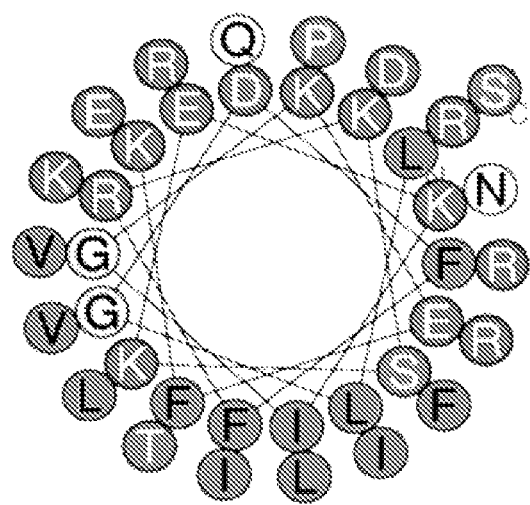
FIG. 1A illustrates the amino acid sequence of natural peptide (LL37, SEQ ID No. 25).

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

Antimicrobial resistance is on the rise with millions of deaths every year. A few infections are now completely untreatable because of resistance. Resistance arises through one of three ways: natural resistance in certain types of bacteria; genetic mutation; or by one species acquiring resistance from another. Resistance can appear spontaneously because of random mutations; or more commonly following gradual buildup over time, and because of misuse of antibiotics or antimicrobials. Resistant microbes are increasingly difficult to treat, requiring alternative medications or higher doses—which may be more costly or more toxic. Microbes resistant to multiple antimicrobials are called multidrug resistant (MDR); or sometimes superbugs. All classes of microbes develop resistance (i.e. fungi, antifungal resistance; viruses, antiviral resistance; protozoa, antiprotozoal resistance; bacteria, antibiotic resistance).

Patients with infections caused by drug-resistant bacteria are at increased risk of worse clinical outcomes and death, and consume more health-care resources than patients infected with non-resistant strains of the same bacteria.

Resistance in *Klebsiella pneumoniae*, a common respiratory bacterium that can cause life-threatening infections, to a last resort treatment (carbapenem antibiotics) has spread to all regions of the world. *K. pneumoniae* is a major cause of hospital-acquired infections such as pneumonia, bloodstream infections, and infections in newborns and intensive-care unit patients. In some countries, because of resistance, carbapenem antibiotics do not work in more than half of people treated for *K. pneumoniae* infections.

Resistance in *Escherichia coli* to one of the most widely used medicines for the treatment of urinary tract infections (fluoroquinolone antibiotics) is very widespread. There are countries in many parts of the world where this treatment is now ineffective in more than half of patients.

Resistance to first-line drugs to treat infections caused by *Staphlylococcus aureus*, a common cause of severe infections in health facilities and the community, is widespread. People with MRSA (methicillin-resistant *Staphylococcus aureus*) are estimated to be 64% more likely to die than people with a non-resistant form of the infection.

Colistin is the last resort treatment for life-threatening infections caused by Enterobacteriaceae which are resistant to carbapenems. Resistance to Colistin has recently been detected in several countries and regions, making infections caused by such bacteria untreatable.

Antimicrobial resistance is a complex problem that affects all of society and is driven by many interconnected factors. Single, isolated interventions have limited impact. Coordinated action is required to minimize the emergence and spread of antimicrobial resistance. Greater innovation and investment are required in research and development of new antimicrobial medicines, vaccines, and diagnostic tools.

Viral infections, such as those caused by Respiratory Syncytial Virus (RSV), are a major cause of lower respiratory tract infection in children and elderly adults. RSV is a major pathogenic factor frequently being associated with asthma exacerbation. Tuberculosis (TB) is an infection caused by slow-growing bacteria that grow best in areas of the body that have lots of blood and oxygen such as lung. Thus, both viral and MDR-TB infection are major infectious problems in lung.

Natural AMPs are short cationic peptides (usually <50 a.a.) that interact with microorganisms to fight against inhaled pathogens and maintain homeostasis of the airways and lung. AMPs disclosed herein have the minimum peptide length necessary to achieve optimal in vitro activity against a broad spectrum of microbial pathogens, while minimizing hemolytic and cytotoxic effects, and are also efficacious in treating viral and TB infection. It is expected that A4 AMPs will be effective against all enveloped viruses including poxvirus, herpesvirus, rhabdovirus, hepadnavirus, baculovirus, orthomyxovirus, paramyxovirus, retrovirus, togavirus, bunyavirus and flavivirus, and other RNA viruses such as Respiratory Syncytial Virus (RSV), measles, mumps, parainfluenza viruses and others.

Using in vitro and in vivo approaches, it has been demonstrated that SPLUNC1 displays antimicrobial activity and that the activity may be partly attributed to a short peptide region of 30 amino acid residues in length. This segment of SPLUNC1 has a charge of +2 and displays an α-helical amphipathic structure. Because the in vitro antibacterial activity was surprisingly low for this 30 amino acid peptide fragment, referred to as alpha4 (A4), this region was used as a template for generating antimicrobial peptide derivatives with enhanced potencies. As length may influence activity, the length was reduced to 24 or 18 residues as a comparable template for the new AMP derivatives. Disclosed herein are 3 series of AMPs with 30 residues, with 24 residues, and with 18 residues.

Based on the principle that antibacterial function depends on the arrangement of the cationic and hydrophobic residues into an amphipathic helix, the amphipathicity was increased and the effects on antibacterial activity were tested. Further, AMPs were generated by (1) increasing the cationic content, (2) decreasing the hydrophobicity, and (3) rearranging the residues with the intent to increase the amphipathicity or hydrophobic moment (pH).

Serial A4 derived AMPs were designed while modifying only one amino acid substitution at a time to determine the resulting antimicrobial activity. It was found that antimicrobial activity increases with charge and the ratio of pH/H until it reaches an optimal potency. Once the optimal activity is reached, antibacterial activity either goes down or remains the same as pH/H and charge continue to increase. The generated peptides not only display broad-spectrum antimicrobial activity against different strains of multidrug resistant bacteria and viruses but also work under extreme conditions of high salt and acidic pH. They also display substantial anti-biofilm properties and in vivo efficacy in both respiratory and septicemic models of *P. aeruginosa* infections. AMPs, particularly the novel A4 peptides described herein, exhibit great potential as new anti-viral agents; e.g., all enveloped viruses such as poxvirus, herpesvirus, rhabdovirus, hepadnavirus, baculovirus, orthomyxovirus, paramyxovirus, retrovirus, togavirus, Bunyavirus and flavivirus, and other RNA viruses such as Respiratory Syncytial Virus (RSV), measles, mumps, parainfluenza viruses and others. AMPs have shown potential as antibacterial agents; e.g., all gram-negative and gram-positive bacteria including, but not limited to, atypical bacteria, tuberculosis (TB) and *mycoplasma* and as well as anticancer agents. The in vitro and in vivo antimicrobial activities of A4-derived peptides are extremely strong and are not matched by any other currently available natural or engineered antimicrobial peptides. The safety profile of A4 derived peptides as demonstrated by the relatively low cytotoxicity against mammalian cells and the systemic toxicity in mouse blood circulation are superior to Colistin, a last resort clinical antibiotic used to treat drug resistant bacterial infection. Therefore, we have successfully developed a set of excellent antimicrobial peptides as novel peptide antibiotics that are potentially critical to the treatment of drug resistant microbial infection. Additionally, we have characterized the minimum peptide length necessary to achieve optimal in vitro activity against a broad spectrum of microbial pathogens, while minimizing hemolytic and cytotoxic effects.

Disclosed AMPs also have anti-cancer and anti-tumor activities.

Figure 1B:
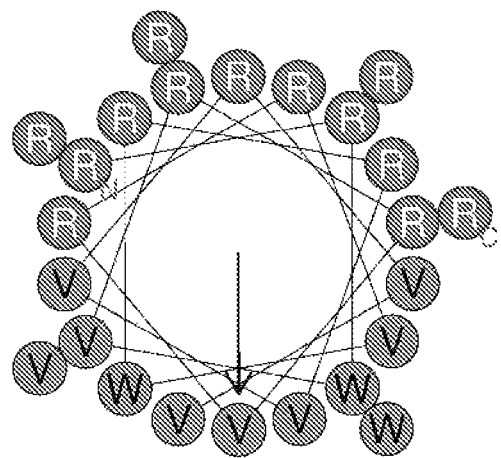
FIG. 1B illustrated the amino acid sequence of engineered peptide (WLBU2, SEQ ID No. 26). Both are cationic amphipathic peptides with the property to fold into alpha helical structures.

The amino acid sequences of natural peptide, LL37 (SEQ ID No. 25), and engineered peptide, WLBU2 (SEQ ID No. 26) can be found in Table 2. LL37 (SEQ ID No. 25) is a human α-helical peptide and WLBU2 (SEQ ID No. 26) is an engineered α-helical peptide; each alpha helical structure is illustrated in FIGS. 1A and 1B, respectively. Natural peptides tend not to work in high salt concentration, acidic pH, and in systemic circulation.

It must be noted that as used herein and in the appended claims, the singular forms "a," "an," and "the" include plural reference unless the context clearly dictates otherwise. Thus, for example, reference to an "amino acid" is a reference to one or more amino acids and equivalents thereof known to those skilled in the art, and so forth.

As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering," when used in conjunction with an AMP, can include, but is not limited to, providing an AMP into or onto the target tissue; providing an AMP systemically to a patient by, e.g., intravenous injection whereby the therapeutic reaches the target tissue; providing an AMP in the form of the encoding sequence thereof to the target tissue (e.g., by so-called gene-therapy techniques). "Administering" a composition may be accomplished by injection, topical administration, or by either method in combination with other known techniques. Such combination techniques include heating, radiation and ultrasound.

The term "animal" as used herein includes, but is not limited to, humans and non-human vertebrates such as wild, domestic and farm animals.

As used herein, the terms "antimicrobial," "anti-bacterial," or "anti-viral" refer to the ability of the AMPs described herein to prevent, inhibit or destroy the growth of microbes such as bacteria, fungi, protozoa and viruses.

As used herein, the term "peptide" refers to an oligomer of at least two contiguous amino acid residues, linked together by a peptide bond.

The term "kill" and like terms, refers to the ability of an AMP to inhibit or destroy growth of a cellular (e.g., self-replicating) microbe, such as, without limitation, a bacterium or fungus, for example, by reducing a number of colony-forming units (CFU) of the microorganism in a bacterial culture or colony, or to inhibit growth rate of a colony or culture of cells. Likewise, with reference to virus particles or virions (e.g., non-self-replicating), the term "neutralize" refers to a reduction of infectivity of a single virion and to overall infectivity (e.g., a reduction in the number of infectious units (IU) or plaque-forming units (PFU)) of a sample of virus particles. Non-limiting examples of killing of bacteria or fungi, and neutralization of virions, and methods of testing for such killing or neutralization are provided in the Examples below.

The term "inhibiting" includes the administration of an AMP of embodiments herein to prevent the onset of the symptoms, alleviating the symptoms, reducing the symptoms, delaying or decreasing the progression of the infection and/or its symptoms, or eliminating condition or infection.

By "pharmaceutically acceptable," it is meant the carrier, diluent or excipient must be compatible with the other ingredients of the formulation and not deleterious to the recipient thereof.

The term "residue" refers to the length of the amino acid sequence. For example, SEQ ID No. 16 LKKWWKKVKGLLGGLLGKVKSVIK is 24 amino acid residues long.

As used herein, the term "therapeutic" means an agent utilized to treat, combat, ameliorate, prevent or improve an unwanted condition or infection of a patient. In part, embodiments herein are directed to the treatment of bacterial, fungal, viral, protozoan or microbial infections. Embodiments also include the treatment of chronic obstructive pulmonary disease (COPD), pulmonary fibrosis, cystic fibrosis, asthma, rhinosinusitis, septicemia, RSV, or TB. Embodiments also include the treatment of cancer.

A "therapeutically effective amount" or "effective amount" of a composition is a predetermined amount calculated to achieve the desired effect, i.e., to kill bacteria, viruses, fungi, protozoa, or microbes or to destroy or kill cancerous cells or tumors. The activity contemplated by the present methods includes both medical therapeutic and/or prophylactic treatment, as appropriate. The specific dose of an AMP administered according to this invention to obtain therapeutic and/or prophylactic effects will, of course, be determined by the particular circumstances surrounding the case, including, for example, the AMP administered, the route of administration, and the condition being treated. The effective amount administered will be determined by the physician in the light of the relevant circumstances including the condition to be treated, the choice of AMP to be administered, and the chosen route of administration, and therefore the above dosage ranges are not intended to limit the scope of the invention in any way. A therapeutically effective amount of an AMP of this invention is typically an amount such that when it is administered in a physiologically tolerable excipient composition, it is sufficient to achieve an effective systemic concentration or local concentration in the tissue.

The terms "treat," "treated," or "treating" as used herein refers to both therapeutic treatment and prophylactic or preventative measures, wherein the object is to prevent or slow down (lessen) an undesired physiological condition or infection, or to obtain beneficial or desired clinical results. For the purposes of this invention, beneficial or desired clinical results include, but are not limited to, alleviation of symptoms; diminishment of the extent of cancer, the condition or infection; stabilization (i.e., not worsening) of the state of cancer, the condition or infection; delay in onset or slowing of the progression of cancer, the condition or infection; amelioration of cancer, the condition or infection; and remission (whether partial or total), whether detectable or undetectable, or enhancement or improvement of cancer, the condition or infection. Treatment includes eliciting a clinically significant response without excessive levels of side effects. Treatment also includes prolonging survival as compared to expected survival if not receiving treatment.

Generally speaking, the term "tissue" refers to any aggregation of similarly specialized cells which are united in the performance of a particular function.

Amino acid codes known to those skilled in the art and provided in Table 1 will be used throughout this disclosure.

TABLE 1

Amino Acid Codes

| 3-letter Designation | Single-letter Designation | Amino acid |
|---|---|---|
| Ala | A | Alanine |
| Arg | R | Arginine |
| Asn | N | Asparagine |
| Asp | D | Aspartic Acid |
| Cys | C | Cysteine |
| Gln | Q | Glutamine |
| Glu | E | Glutamic Acid |
| Gly | G | Glycine |
| His | H | Histidine |
| Ile | I | Isoleucine |
| Leu | L | Leucine |
| Lys | K | Lysine |
| Met | M | Methionine |
| Phe | F | Phenylalanine |
| Pro | P | Proline |
| Ser | S | Serine |
| Thr | T | Threonine |
| Trp | W | Tryptophan |
| Tyr | Y | Tyrosine |
| Val | V | Valine |
| Asx | B | Asn or Asp |
| Glx | Z | Gln or Glu |
| Xle | J | Leu or Ile |
| Sec | U | Selenocysteine |
| Pyl | O | Pyrrolysine |

Embodiments herein are directed to engineered AMPs and methods for using such engineered AMPs for the treatment of diseases including, for example, antibiotic resistant bacteria infections, COPD, asthma, pulmonary fibrosis, cystic fibrosis, rhinosinusitis, septicemia, RSV, TB, or cancer. The engineered AMPs of various embodiments may have a primary structure (i e amino acid sequence) of about 12 to about 32 residues in length, and a substantially helical secondary structure (i.e. three-dimensional structure). The helical structure may be substantially amphipathic being more hydrophobic on one face of the helix and more hydrophilic on the opposite face of the helix. Hydrophobic moment, $\mu H$, is a measure amphipathicity, and in certain embodiments, the engineered AMPs may have a $\mu H$ of about 0.1 to about 1. Such amphipathic AMPs may provide broad spectrum antimicrobial activity against bacteria, parasites, viruses, and fungi that is more effective than the activity of native AMPs. The peptides may also show other beneficial properties such as angiogenesis, chemotaxis, apoptotic properties, tissue regeneration, cytokine release, and anti-tumor properties.

Figure 33:
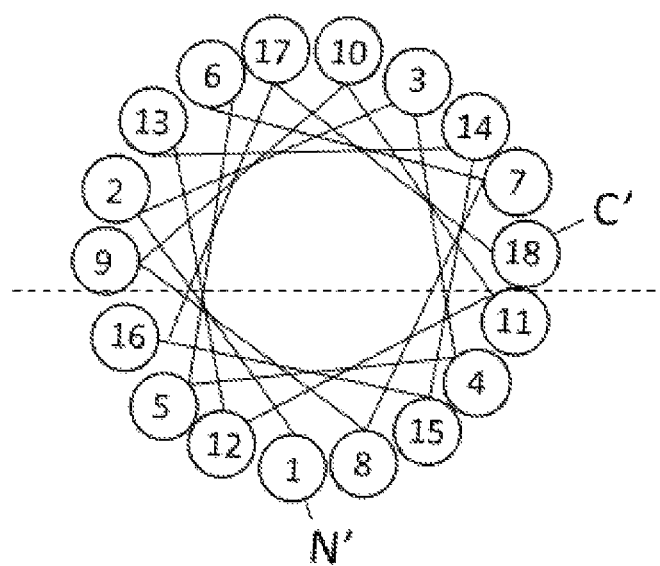
FIG. 33 is a schematic showing the structure of Formula I.

The helical structure of an AMP can be represented as illustrated in Formula I as shown in FIG. 33 where each numbered circle is a sequentially numbered amino acid residue. The linear amino acid sequence of Formula I is: N'-1-2-3-4-5-6-7-8-9-10-11-12-13-14-15-16-17-18-C'.

Amino acid residues below the dotted line, 1, 4, 5, 8, 11, 12, 15, and 16, may each individually be a hydrophobic amino acid, such as, L or D form of alanine, isoleucine, leucine, tryptophan, phenylalanine, valine, proline, or glycine. In some embodiments, one or more of amino acid residues 1, 4, 5, 8, 11, 12, 15, and 16 may be hydrophilic, so long as the face of the helix below the dotted line exhibits a hydrophobic character. In various embodiments, each residue above the dotted line, 2, 3, 6, 7, 9, 10, 13, 14, 17, and 18, may be a non-hydrophobic or hydrophilic amino acid, such as L or D form of arginine, lysine, aspartic acid, glutamic acid, glutamine, asparagine, histidine, serine, threonine, tyrosine, cysteine, methionine, tryptophan, selenocysteine, and pyrrolysine. In some embodiments, one or more of amino acid residues 2, 3, 6, 7, 9, 10, 13, 14, 17, and 18 may be hydrophobic, so long as the face of the helix above the dotted line is less hydrophobic than the face of the helix below the dotted line.

In particular embodiments, the engineered AMP may have the amino acid sequence provided in SEQ. ID. Nos. 2-23 or 27-34 as presented in TABLE 2.

TABLE 2

Antimicrobial Peptides

| Length | SEQ ID No. | Primary Sequence | Charge | H | µH | µH/H |
|---|---|---|---|---|---|---|
| 30 | 1 | ILKPGGGTSGGLLGGLLGKVTSVIPGLNNI | 2 | 0.373 | 0.558 | 0.668 |
| 30 | 2 | ILKKWWββαβGLLGβLLGαVββVIKβLββI | | | | |
| 30 | 3 | ILKKWWGTSGGLLGGLLGKVTSVIKGLNNI | 4 | 0.563 | 0.594 | 0.948 |
| 30 | 4 | ILKKWWKTSGGLLGGLLGKVTSVIKGLNNI | 5 | 0.594 | 0.561 | 1.059 |
| 30 | 5 | ILKKWWKTSKGLLGGLLGKVTSVIKGLNNI | 6 | 0.602 | 0.528 | 1.140 |
| 30 | 6 | ILKKWWKTSKGLLGGLLGKVTSVIKGLKNI | 7 | 0.605 | 0.515 | 1.175 |
| 30 | 7 | ILKKWWKTSKGLLGGLLGGVTSVIKKLKKI | 8 | 0.617 | 0.502 | 1.229 |
| 30 | 8 | ILKKWWKTSKGLLGGLLGGVTSVIKKLKKI | 8 | 0.628 | 0.502 | 1.251 |

TABLE 2-continued

Antimicrobial Peptides

| Length | SEQ ID No. | Primary Sequence | Charge | H | μH | μH/H |
|---|---|---|---|---|---|---|
| 30 | 9 | ILKKWWKTVKGLLGGLLGGVTSVIKKLKKI | 8 | 0.630 | 0.503 | 1.252 |
| 30 | 10 | ILKKWWKKVKGLLGKLLGGVKSVIKGLNNI | 8 | 0.694 | 0.487 | 1.425 |
| 30 | 11 | ILKKWWKKVKGLLGKLLGGVKKVIKGLNNI | 9 | 0.717 | 0.455 | 1.576 |
| 24 | 12 | LKKWWKβαKGLLGGLLGKVββVIK | | | | |
| 24 | 13 | LKKWWKTSKGLLGGLLGKVTSVIK | 6 | 0.606 | 0.489 | 1.239 |
| 24 | 14 | LKKWWKTVKGLLGGLLGKVTSVIK | 6 | 0.658 | 0.542 | 1.214 |
| 24 | 15 | LKKWWKKVKGLLGGLLGKVTSVIK | 7 | 0.676 | 0.490 | 1.380 |
| 24 | 16 | LKKWWKKVKGLLGGLLGKVKSVIK | 8 | 0.694 | 0.438 | 1.584 |
| 24 | 17 | LKKWWKKVKGLLGGLLGKVKKVIK | 9 | 0.728 | 0.398 | 1.829 |
| 18 | 18 | αKKααKKαKGαLGGLαGK | | | | |
| 18 | 19 | LKKWWKKVKGLLGGLLGK | 6 | 0.682 | 0.460 | 1.483 |
| 18 | 20 | LKKLLKKVKGWLGGLWGK | 6 | 0.663 | 0.460 | 1.441 |
| 18 | 21 | VKKLLKKVKGWLGGLWGK | 6 | 0.637 | 0.433 | 1.471 |
| 18 | 22 | GKKLLKKVKGWLGGLWGK | 6 | 0.570 | 0.366 | 1.557 |
| 18 | 23 | GKKLLKKGKGWLGGLWGK | 6 | 0.503 | 0.298 | 1.688 |
| 24 | 24* | GVKKKWKKKLGLKLWLKISGVVLG | 8 | 0.018 | 0.437 | 0.041 |
| 37 | 25** | LLGDFFRKSKEKIGKEFKRIVQRIKDFLRNLLPRTES | 6 | 0.214 | 0.521 | 2.43 |
| 24 | 26*** | RRWVRRVRRVWRRVVRVVRRWVRR | 13 | 0.141 | 0.798 | 5.66 |
| 24 | 27 | KLWKKGKGGKLTKSLTWVLVGILV | 6 | 0.542 | 0.013 | 0.024 |
| 18 | 28 | VWKWGKLGKLLKLGKLGK | 6 | 0.46 | 0.017 | 0.04 |
| 18 | 29 | KKLGKKVVGKLGTSKVWKLIGWLL | 7 | 0.49 | 0.016 | 0.032 |
| 24 | 30 | LKKWWKKVLGLLGGLKGKVTSVIK | 7 | 0.49 | 0.638 | 1.30 |
| 24 | 31 | LKKWLKKVLGLKGGLWGKVTSVIK | 7 | 0.49 | 0.577 | 1.18 |
| 24 | 32# | RRWVRRVRRVWRRVVRVVRRWVRR (underlined valines are substituted with D-amino acid versions) | 13 | 0.141 | NA | NA |
| 24 | 33# | RRWVRRVRRVWRRVVRVVRRWVRR (underlined valines are substituted with D-amino acid versions) | 13 | 0.141 | NA | NA |
| 24 | 34# | RRWVRRVRRVWRRVVRVVRRWVRR (underlined valines are substituted with D-amino acid versions) | 13 | 0.141 | NA | NA |

*SEQ ID No. 24 is a scrambled control without amphipathicity, used as a negative control.
**SEQ ID No. 25 is a natural peptide LL37.
***SEQ ID No. 26 is an engineered peptide WLBU2.
The uH (a measure of amphipathicity) was theoretically calculated based on the helical structure. Because the secondary structure of the D-enantiomers of WLBU2 is not predictable and has to be experimentally determined, uH calculations are not applicable to these AMPs.

Figure 3:
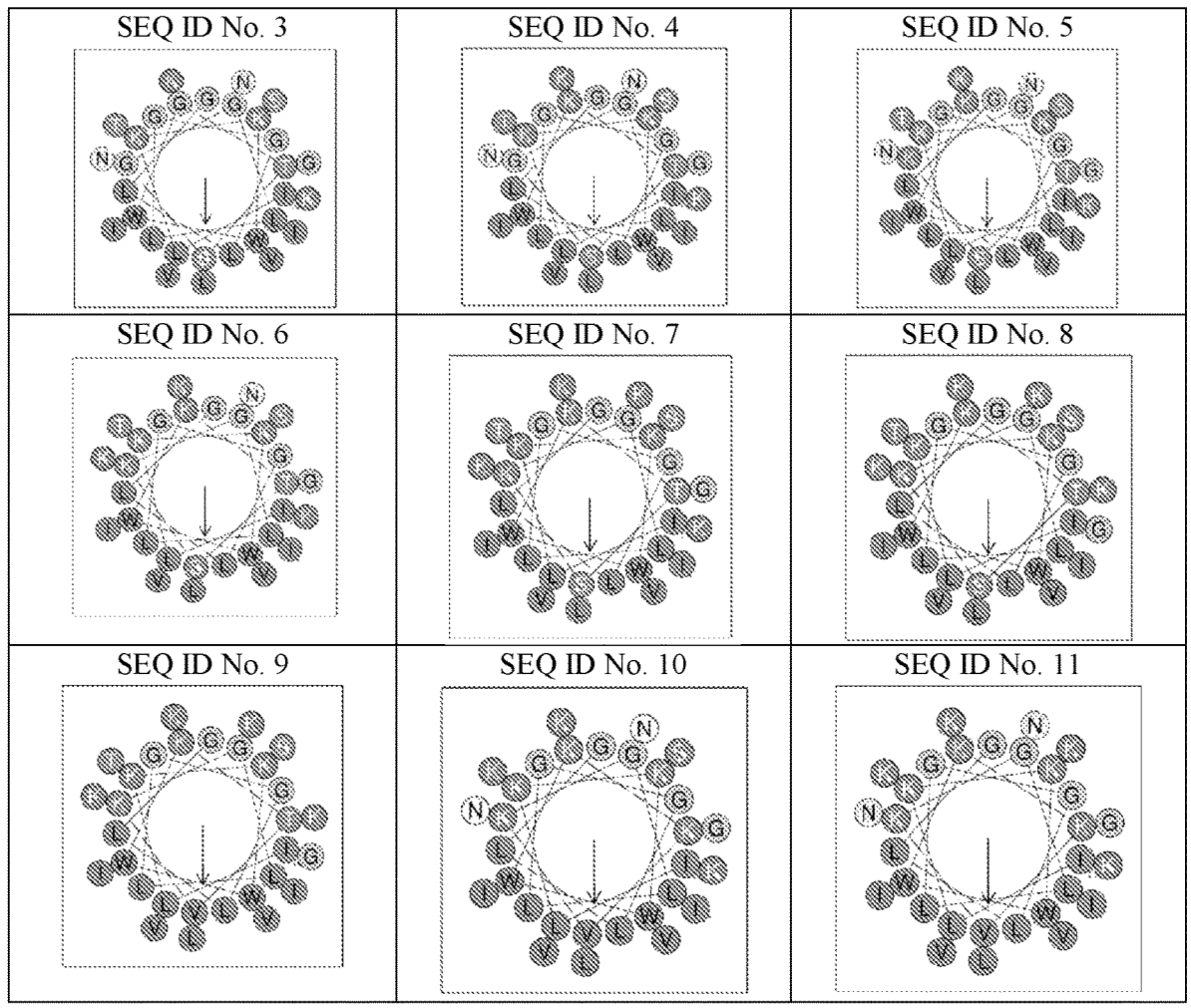
FIG. 3 illustrates the amphipathic structure of the 30 amino acid AMP series, SEQ ID Nos. 3-11, using helical wheel analyses.

In some embodiments, the 30 residue AMP sequences are identified as SEQ ID No. 3, SEQ ID No. 4, SEQ ID No. 5, SEQ ID No. 6, SEQ ID No. 7, SEQ ID No. 8, SEQ ID No. 9, SEQ ID No. 10, or SEQ ID No. 11. FIG. 3 illustrates the alpha helical structure of each of the 30 residue AMP series, wherein one face of the helix is hydrophobic and the opposite face of the helix is hydrophilic.

Figure 4:
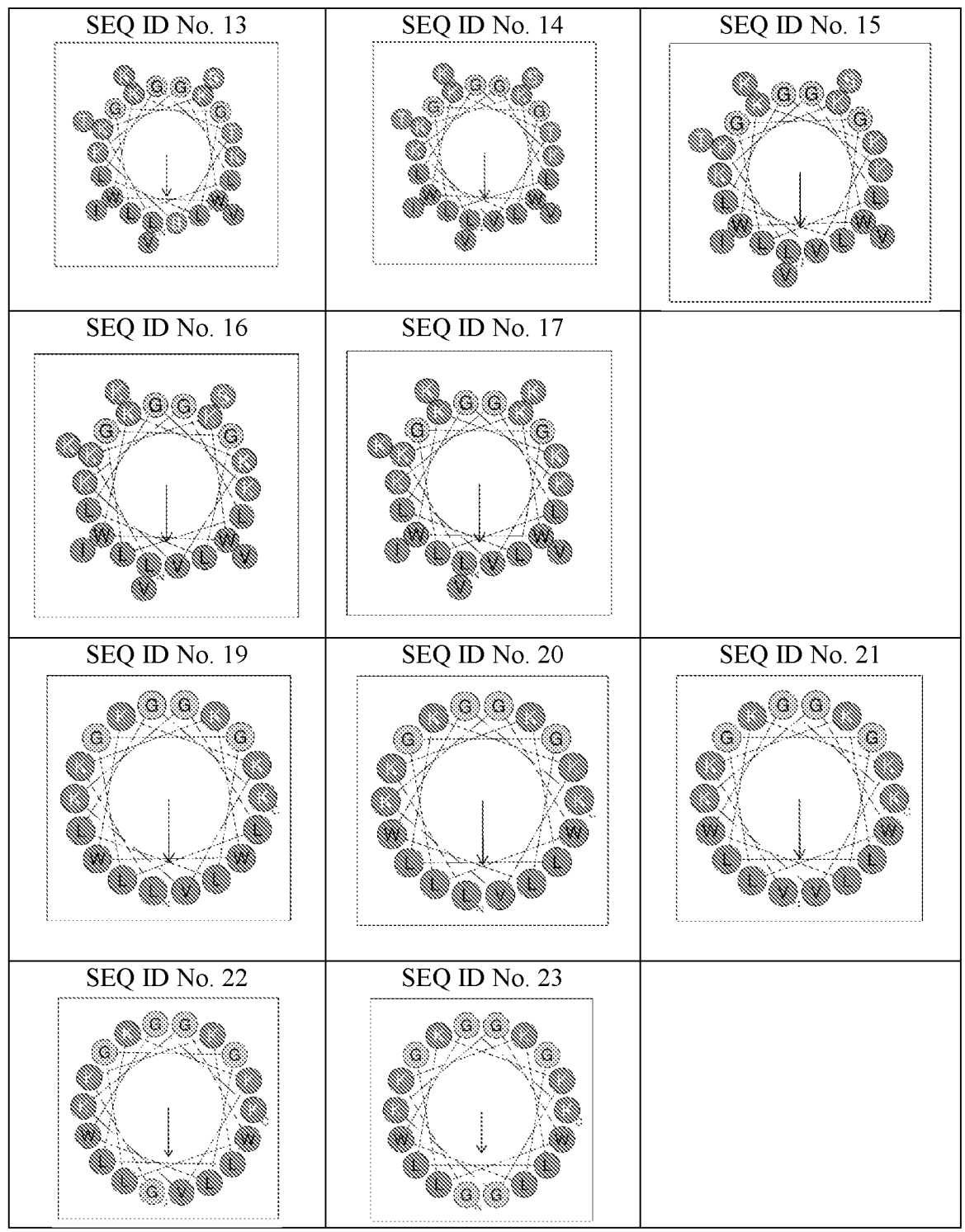
FIG. 4 illustrates the amphipathic structure of the 24 or 18 amino acids AMP series, SEQ ID Nos. 13-17, 19-23, using helical wheel analyses.

In some embodiments, the 24 residue AMP sequences are identified as SEQ ID No. 13, SEQ ID No. 14, SEQ ID No. 15, SEQ ID No. 16, SEQ ID No. 17, SEQ ID No. 27, SEQ ID No. 29, SEQ ID No. 30, SEQ ID No. 31, SEQ ID No. 26, SEQ ID No. 32, SEQ ID No. 33, or SEQ ID No. 34. FIG. 4 illustrates the representative alpha helical structures of some of the 24 residue AMP series, wherein one face of the helix is hydrophobic and the opposite face of the helix is hydrophilic.

In some embodiments, the 18 residue AMP sequences are identified as SEQ ID No. 19, SEQ ID No. 20, SEQ ID No. 21, SEQ ID No. 22, SEQ ID No. 23, or SEQ ID No. 28. FIG. 4 illustrates the representative alpha helical structures of some of the 18 residue AMP series, wherein one face of the helix is hydrophobic and the opposite face of the helix is hydrophilic.

In some embodiments, the 24 residue AMP sequences are identified as SEQ ID No. 26, SEQ ID No. 32, SEQ ID No. 33, or SEQ ID No. 34. These WLBU2-derived peptides were generated by modifying the potential neutrophil elastase digestion sites with D-amino acid substitution of valine at different sites (underlined in Table 2). Although these predicted protease digestion sites may not always be functional, the modifications enhance the peptide stability.

In certain embodiments, the amino acid sequence of the AMP can be represented by the consensus sequence (30 residue AMP consensus, SEQ ID No. 2): ILKKWWββαβGLLGβLLGαVββVIKβLββI, wherein α represents a hydrophobic residue and 13 represents a non-hydrophobic or hydrophilic residue. In some embodiments, the hydrophobic amino acid is selected from the group consisting of the L or D form of the following: alanine, isoleucine, leucine, tryptophan, phenylalanine, valine, proline, and glycine. In some embodiments, the non-hydrophobic amino acid is selected from the group consisting of the L or D form of the following: arginine, lysine, aspartic acid, glutamic acid, glutamine, asparagine, histidine, serine, threonine, tyrosine, cysteine, methionine, selenocysteine, and pyrrolysine.

In certain embodiments, the amino acid sequence of the AMP can be represented by the consensus sequence (24 residue AMP consensus, SEQ ID No. 12): LKKWWKβαKGLLGGLLGKVββVIK, wherein a represents a hydrophobic residue and β represents a non-hydrophobic or hydrophilic residue. In some embodiments, the hydrophobic amino acid is selected from the group consisting of the L or D form of the following: alanine, isoleucine, leucine, tryptophan, phenylalanine, valine, proline, and glycine. In some embodiments, the non-hydrophobic amino acid is selected from the group consisting of the L or D form of the following: arginine, lysine, aspartic acid, glutamic acid, glutamine, asparagine, histidine, serine, threonine, tyrosine, cysteine, methionine, selenocysteine, and pyrrolysine.

In certain embodiments, the amino acid sequence of the AMP can be represented by the consensus sequence (18 residue AMP consensus, SEQ ID No. 18): αKKααKKαKGαLGGLαGK, wherein α represents a hydrophobic residue. In some embodiments, the hydrophobic amino acid is selected from the group consisting of the L or D form of the following: alanine, isoleucine, leucine, tryptophan, phenylalanine, valine, proline, and glycine.

In embodiments described herein, the AMPs possess antimicrobial activity wherein a variety of bacteria, viruses, protozoa, fungi, and other microbes are killed when treated with each AMP. The microbes killed are selected from the group consisting of *Enterococcus faecium, Staphylococcus aureus* (including MRSA), *Klebsiella pneumonia, Escherichia coli*, Enterobacteriaceae, *Pseudomonas aeruginosa, Acinetobacter baumannii, Burkholderia* spp., Carbapenem-resistant Enterobacteriaceae, Respiratory syncytial virus, Influenza virus, human immunodeficiency virus, human papilloma virus, human leukemia virus, herpes simplex virus, hepatitis A virus, hepatitis B virus, hepatitis C virus, parainfluenza viruses, rhinoviruses, coronaviruses, enteroviruses, adenoviruses, tuberculosis (TB), gonorrhea, *chlamydia, C. difficile, Borrelia burgdorferi* (Lyme disease), streptococci, *Listeria monocytogenes, Mycoplasma pneumonia, Meningococcus meningitis, Haemophilus influenza, Streptococcus pneumoniae*, and *Moraxella catarrhalis*.

In embodiments described herein, the AMPs possess anti-cancer or anti-tumor activity. In some embodiments, the AMP may be selected from SEQ ID NOs. 2-23 and 27-34. In some embodiments, the AMP might be selected from SEQ ID NOs. 2, 12, 18, 26, and 32-34.

In some embodiments, a method of treating a microbial infection in a subject in need thereof comprises administering to the subject a therapeutic amount of an AMP. In some embodiments, the AMP may be selected from SEQ ID NOs. 2-23 and 27-34. In some embodiments, the AMP might be selected from SEQ ID NOs. 2, 12, 18, 26, and 32-34. In some embodiments, the AMP may be in a pharmaceutical composition further comprising a pharmaceutically acceptable excipient.

In some embodiments, the microbial infection is selected from *Enterococcus faecium, Staphylococcus aureus* (including MRSA), *Klebsiella pneumonia, Escherichia coli*, Enterobacteriaceae, *Pseudomonas aeruginosa, Acinetobacter baumannii, Burkholderia* spp., Carbapenem-resistant Enterobacteriaceae, Respiratory syncytial virus, Influenza virus, human immunodeficiency virus, human papilloma virus, human leukemia virus, herpes simplex virus, hepatitis A virus, hepatitis B virus, hepatitis C virus, parainfluenza viruses, rhinoviruses, coronaviruses, enteroviruses, adenoviruses, tuberculosis (TB), gonorrhea, *chlamydia, C. difficile, Borrelia burgdorferi* (Lyme disease), streptococci, *Listeria monocytogenes, Mycoplasma pneumonia, Meningococcus meningitis, Haemophilus influenza, Streptococcus pneumoniae*, and *Moraxella catarrhalis*. In general, antiviral activity of the A4 AMPs can be extended to all enveloped viruses such as poxvirus, herpesvirus, rhabdovirus, hepadnavirus, baculovirus, orthomyxovirus, paramyxovirus, retrovirus, togavirus, bunyavirus and flavivirus, and other RNA viruses such as Respiratory Syncytial Virus (RSV), measles, mumps, parainfluenza viruses and others.

Some embodiments are directed to a method of treating a condition in a subject in need thereof comprising administering to the subject a therapeutic amount of an AMP. In some embodiments, the condition may be selected from antibiotic resistant bacteria infections, COPD, asthma, pulmonary fibrosis, cystic fibrosis, rhinosinusitis, septicemia, RSV, TB, bacterial infections, viral infections, or a combination thereof. In some embodiments, the AMP may be selected from SEQ ID NOs. 2-23 and 27-34. In some embodiments, the AMP might be selected from SEQ ID NOs. 2, 12, 18, 26, and 32-34. In some embodiments, the AMP may be in a pharmaceutical composition further comprising a pharmaceutically acceptable excipient.

In some embodiments, a method of treating cancer in a subject in need thereof comprises administering to the subject a therapeutic amount of an AMP. In some embodiments, the AMP may be selected from SEQ ID NOs. 2-23 and 27-34. In some embodiments, the AMP might be selected from SEQ ID NOs. 2, 12, 18, 26, and 32-34. In some embodiments, the AMP may be in a pharmaceutical composition further comprising a pharmaceutically acceptable excipient.

In some embodiments, the therapeutic amount of an AMP is about 1 mg/kg to about 150 mg/kg, about 5 mg/kg to about 145 mg/kg, about 10 mg/kg to about 140 mg/kg, about 15 mg/kg to about 135 mg/kg, about 20 mg/kg to about 130 mg/kg, about 25 mg/kg to about 125 mg/kg, about 30 mg/kg to about 120 mg/kg, about 35 mg/kg to about 120 mg/kg, about 40 mg/kg to about 115 mg/kg, about 45 mg/kg to about 110 mg/kg, about 50 mg/kg to about 105 mg/kg, about 55 mg/kg to about 100 mg/kg, about 60 mg/kg to about 95 mg/kg, about 65 mg/kg to about 90 mg/kg, about 70 mg/kg to about 85 mg/kg, about 75 mg/kg to about 80 mg/kg, or a value within any of the foregoing ranges.

In some embodiments, the therapeutic amount of an AMP is from about 0.1 µM to about 32 µM, about 1 µM to about 32 µM, about 2 µM to about 30 µM, about 4 µM to about 28 µM, about 6 µM to about 26 µM, about 8 µM to about 24 µM, about 10 µM to about 22 µM, about 12 µM to about 20 µM, about 14 µM to about 18 µM, or a value within any of the forgoing ranges.

It is well known that small drug molecules cannot easily penetrate biofilm, but AMPs can penetrate and disrupt the biofilm. In some embodiments, a method of reducing biofilm in a subject in need thereof comprises administering to the subject a therapeutic amount of an AMP. To reduce or destroy biofilm, it is believed a higher concentration of the AMP is required. In some embodiments, the therapeutic amount of an AMP is from about 1 mg/kg to about 150 mg/kg, about 5 mg/kg to about 145 mg/kg, about 10 mg/kg to about 140 mg/kg, about 15 mg/kg to about 135 mg/kg, about 20 mg/kg to about 130 mg/kg, about 25 mg/kg to about 125 mg/kg, about 30 mg/kg to about 120 mg/kg, about 35 mg/kg to about 120 mg/kg, about 40 mg/kg to about 115 mg/kg, about 45 mg/kg to about 110 mg/kg, about 50 mg/kg to about 105 mg/kg, about 55 mg/kg to about 100 mg/kg, about 60 mg/kg to about 95 mg/kg, about 65 mg/kg to about 90 mg/kg, about 70 mg/kg to about 85 mg/kg, or about 75 mg/kg to about 80 mg/kg, or a value within any of the foregoing ranges. In some embodiments, the therapeutic amount of an AMP is from about 0.1 µM to about 32 µM, about 1 µM to about 32 µM, about 2 µM to about 30 µM, about 4 µM to about 28 µM, about 6 µM to about 26 µM, about 8 µM to about 24 µM, about 10 µM to about 22 µM, about 12 µM to about 20 µM, about 14 µM to about 18 µM, or a value within any of the forgoing ranges.

In some embodiments, a method of decreasing inflammation in a subject in need thereof comprises administering to the subject a therapeutic amount of an AMP. The immunoregulatory response is activated once a subject is infected with an infectious microbe; when the infectious microbe is killed the surrounding cells secrete tumor necrosis factor (TNF). This response leads to inflammation and, if left untreated or uncontrolled, can lead to tissue damage. Inflammation is controlled as the concentration of TNF secreted is lessened. In some embodiments, the AMP may control inflammation and the amount of TNF secreted without killing the infectious agent. In some embodiments, the AMP may control inflammation and the amount of TNF secreted and kills the infectious agent.

In some embodiments, a method of minimizing the cytopathic effect of antimicrobials on a subject comprises administering to the subject a therapeutic amount of an AMP to a subject in need thereof. Cytopathic effect or cytopathogenic effect (abbreviated CPE) refers to structural changes in host cells that are caused by viral invasion. Due to CPEs, the infecting virus causes lysis of the host cell or when the cell dies without lysis due to an inability to reproduce. Common examples of CPE include rounding of the infected cell, fusion with adjacent cells to form syncytia, and the appearance of nuclear or cytoplasmic inclusion bodies. Minimizing of CPE would result in an increased survival of the host cells.

In certain embodiments, the pharmacokinetic (PK) properties of AMPs may be improved by conjugating molecules to the peptide. The AMPs of embodiments herein may be amidated at the C-terminus. The AMPs may be covalently bound to a protease-sensitive linker for the release of the active drug once at the site of infection. The protease-sensitive linker is selected from the group consisting of cathepsin B and polyethylene glycol (PEG) polymer. The conjugated AMP may also be packaged into liposomes or attached to nanoparticles for delivery. The AMPs may be stapled or "stitched" at 2 or more sites to enhance the pharmaceutical properties.

In some embodiments, the antimicrobial peptide is administered with a traditional antibiotic. In certain embodiments, the antibiotic is selected from the group consisting of penicillin, cephalosporin, vancomycin, polymyxin, rifamycin, lipiarmycin, quinolone, sulfonamide, macrolide, lincosamide, tetracycline, cyclic lipopeptides, glycylcyclines, oxazolidinones, lipiarmycins, and any other known antibiotic.

For example, in some aspects, a pharmaceutical composition comprises an antimicrobial peptide of embodiments herein and a pharmaceutically acceptable carrier or diluent. Methods of embodiments herein may comprise administering an effective amount of a pharmaceutical composition comprising an AMP of embodiments herein.

The AMPs of embodiments herein may be administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the AMPs of embodiments herein (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication. The selection of the specific route of administration and the dose regimen is to be adjusted or titrated by the clinician according to methods known to the clinician in order to obtain the optimal clinical response. The amount of AMP to be administered is that amount which is therapeutically effective. The dosage to be administered will depend on the characteristics of the subject being treated (e.g., the particular animal treated, age, weight, health, types of concurrent treatment, if any), and frequency of treatments, which can be easily determined by one of skill in the art (e.g., by the clinician).

Pharmaceutical formulations containing the AMPs of embodiments herein and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of embodiments herein. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, chemical preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The AMPs of embodiments herein can be formulated for parenteral or intravenous administration by injection, e.g., by bolus injection or infusion. The AMPs can be administered by infusion subcutaneously or intravenously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the AMPs can be formulated readily by combining these AMPs with pharmaceutically acceptable carriers well known in the art. Such carriers enable the AMPs of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active AMPs can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the compositions can take the form of, e.g., tablets or lozenges formulated in a conventional manner.

For administration by inhalation, the AMPs for use according to embodiments herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the AMP and a suitable powder base such as lactose or starch.

The AMPs of embodiments herein can also be formulated in rectal compositions such as suppositories or retention enemas, e.g., containing conventional suppository bases such as cocoa butter or other glycerides.

In addition to the formulations described previously, the AMPs of embodiments herein can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the AMPs can be formulated with suitable polymeric or hydrophobic materials (for example as an emulsion in an acceptable oil) or ion exchange resins, or as sparingly soluble derivatives, for example, as a sparingly soluble salt.

In transdermal administration, the AMPs of embodiments herein, for example, can be applied to a plaster, or can be applied by transdermal, therapeutic systems that are consequently supplied to the organism.

Pharmaceutical compositions of the AMPs also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The AMPs of embodiments herein can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component comprises one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearyl fumarate, fatty acid, fatty alcohol, fatty acid ester, glyceryl behenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

This invention and embodiments illustrating the method and materials used may be further understood by reference to the following non-limiting examples.

Example 1

Antimicrobial Efficacy

Figure 2A:
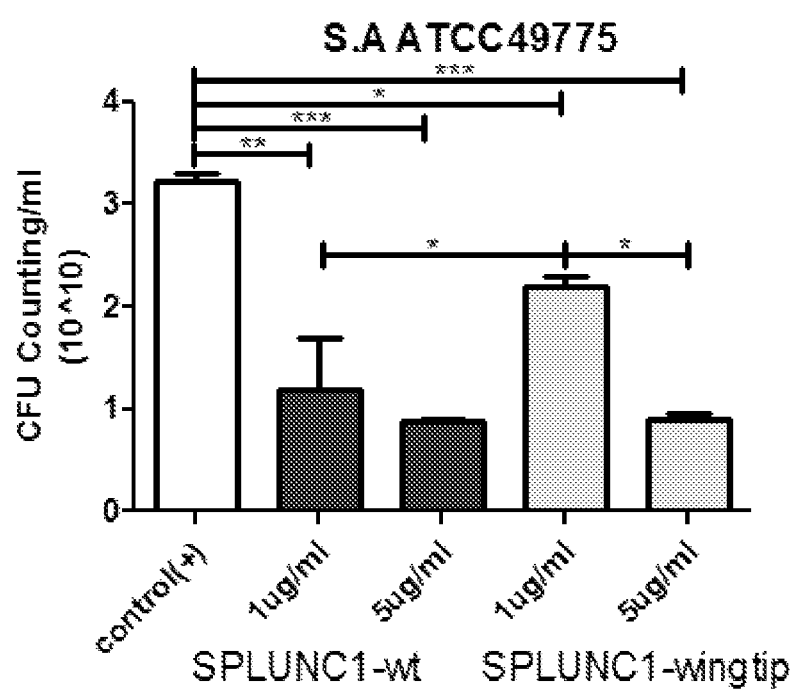
FIG. 2A demonstrates that the SPLUNC1-wt and SPLUNC-wingtip have antimicrobial properties against S.A. ATCC49775.
Figure 2B:
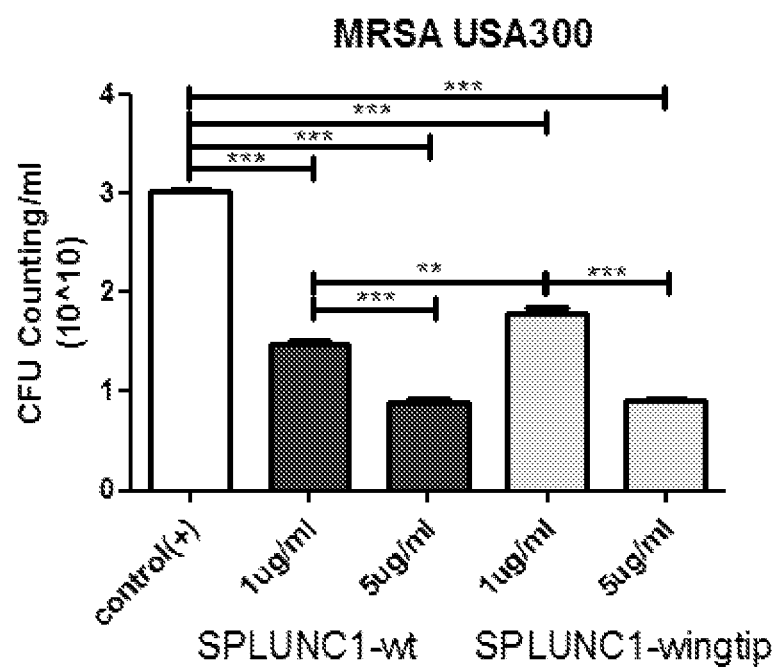
FIG. 2B demonstrates that the SPLUNC1-wt and SPLUNC-wingtip have antimicrobial properties against MRSA USA300.
Figure 2C:
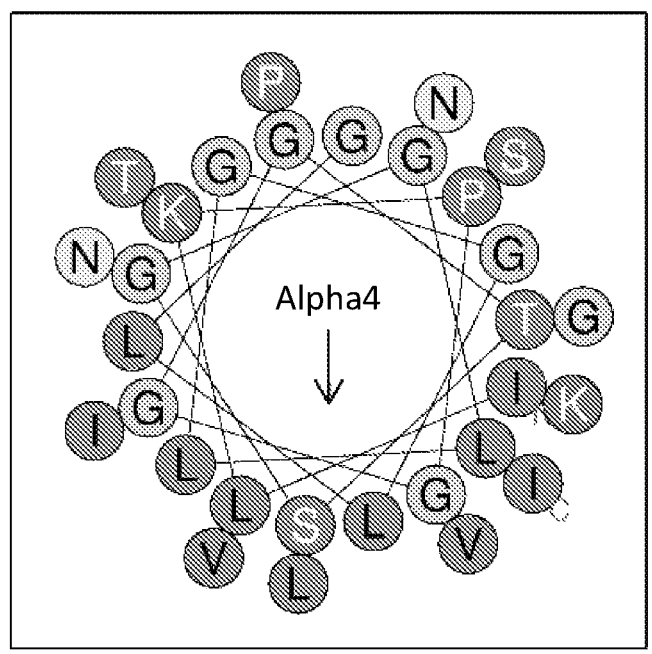
FIG. 2C illustrates the amino acid sequence of Alpha4 (A4, SEQ ID No. 1) in alpha helical structure derived from SPLUNC1, a naturally secreted antimicrobial protein.

The AMPs disclosed herein were derived from the naturally secreted antimicrobial protein SPLUNC1. FIG. 2 demonstrates that SPLUNC1-wt (the wildtype version of the protein) has significant antimicrobial activity against A) S.A. ATCC49775 and B) MRSA USA300 and the antimicrobial activity of SPLUNC1 was decreased when the alpha 4 region was deleted (referred to as the wingtip), see SPLUNC1-wingtip in FIG. 2A) S.A. ATCC49775 and FIG. 2B) MRSA USA300. FIG. 2C) illustrates the alpha helical structure of alpha4 (A4), the 30 residue sequence used as the template to design the disclosed AMPs listed in Table 2.

MIC (minimum inhibitory concentration) was determined using a kinetic killing assay to monitor the bacterial growth once every hour for 18 hours. The bactericidal activities were examined using standard bacterial culture media (MHB) without the inclusion of human blood. The AMPs described herein displayed superior bactericidal activity compared with other naturally-occurring AMPs and clinically used antibiotics (i.e. Colistin).

Figure 5:
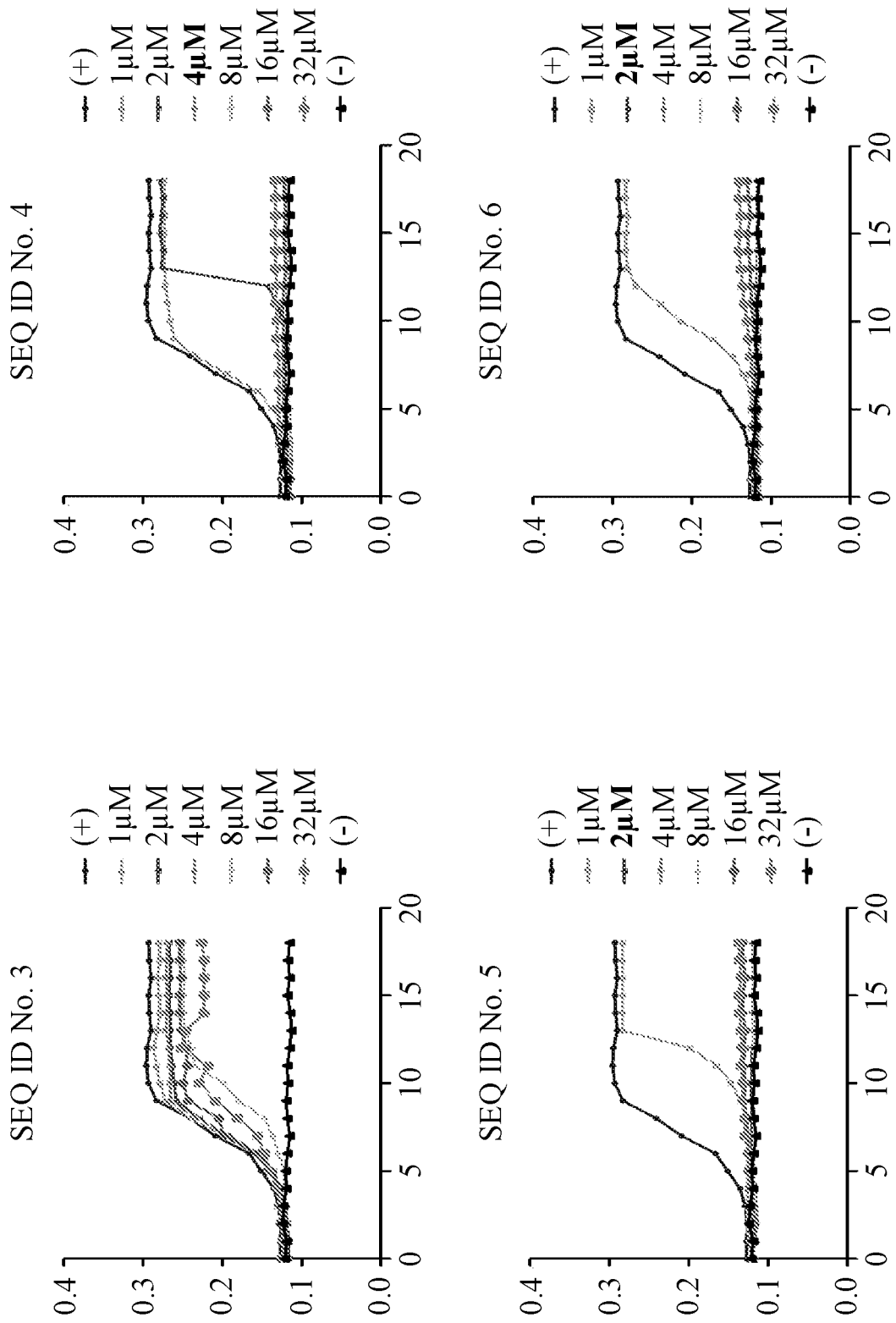
FIG. 5 illustrates the bactericidal activity of 30 amino acid AMP series against *Pseudomonas aeruginosa* (by kinetic bactericidal assay) over time (hours).
Figure 5:
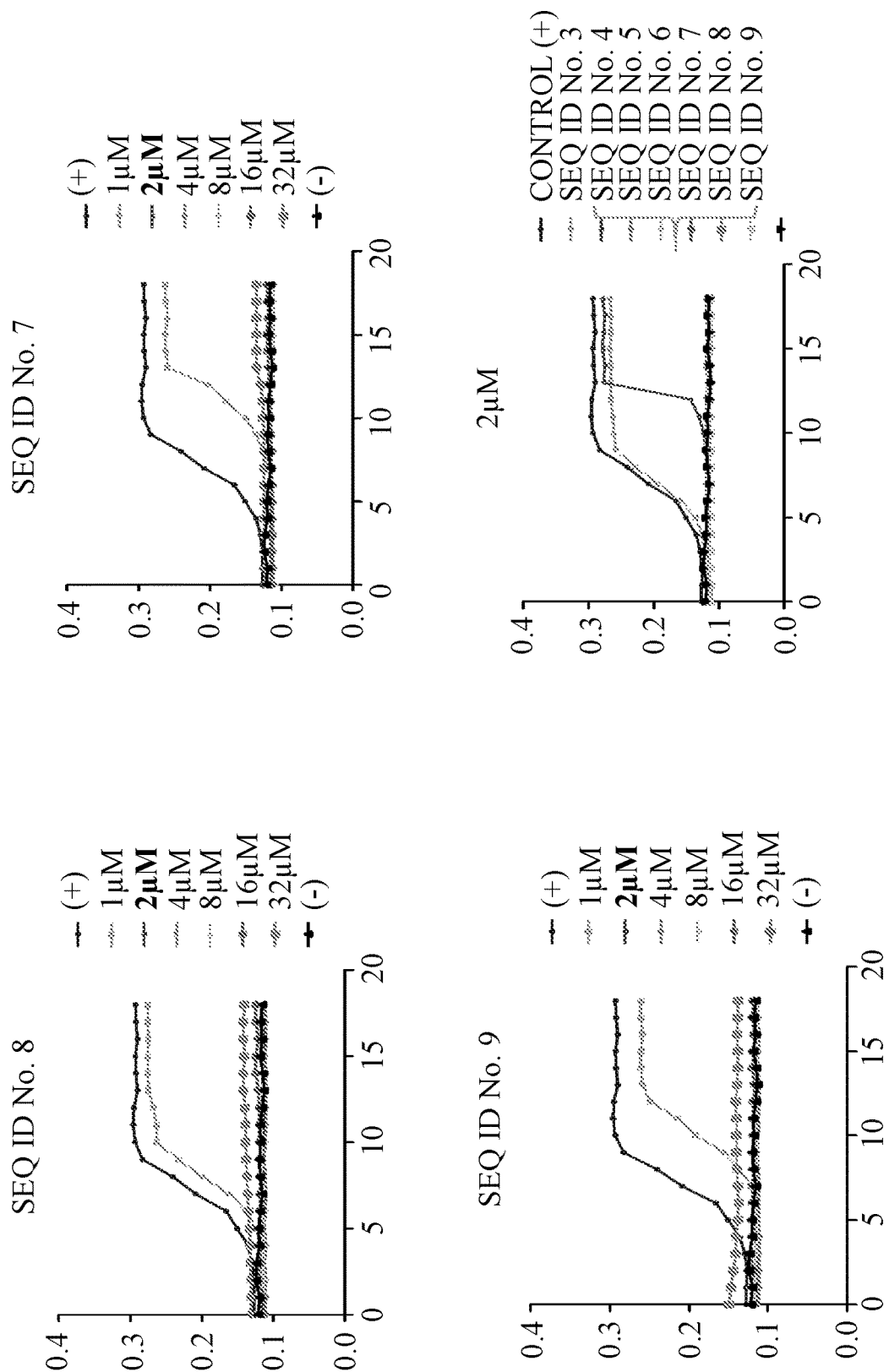

FIG. 5 illustrates the bactericidal activity of the 30 amino acid AMP series against *Pseudomonas aeruginosa* (by kinetic assay) over time (hours). SEQ ID No. 3 did not have strong bactericidal activity against *Pseudomonas aeruginosa* but all other modified AMPs in the 30 amino acid AMP series displayed excellent bactericidal activity. OD reading, at 570 nm, represents bacterial growth; background reading (~0.05) was subtracted from sample readings. Bolded concentration indicates the determined MIC. For example, MIC for SEQ ID No. 4 was 4 µM, MIC for SEQ ID No. 8 was 2 µM, MIC for SEQ ID No. 7 was 2 µM, MIC for SEQ ID No. 5 was 2 µM, MIC for SEQ ID No. 6 was 2 µM, and MIC for SEQ ID No. 9 was 2 µM.

Figure 6:
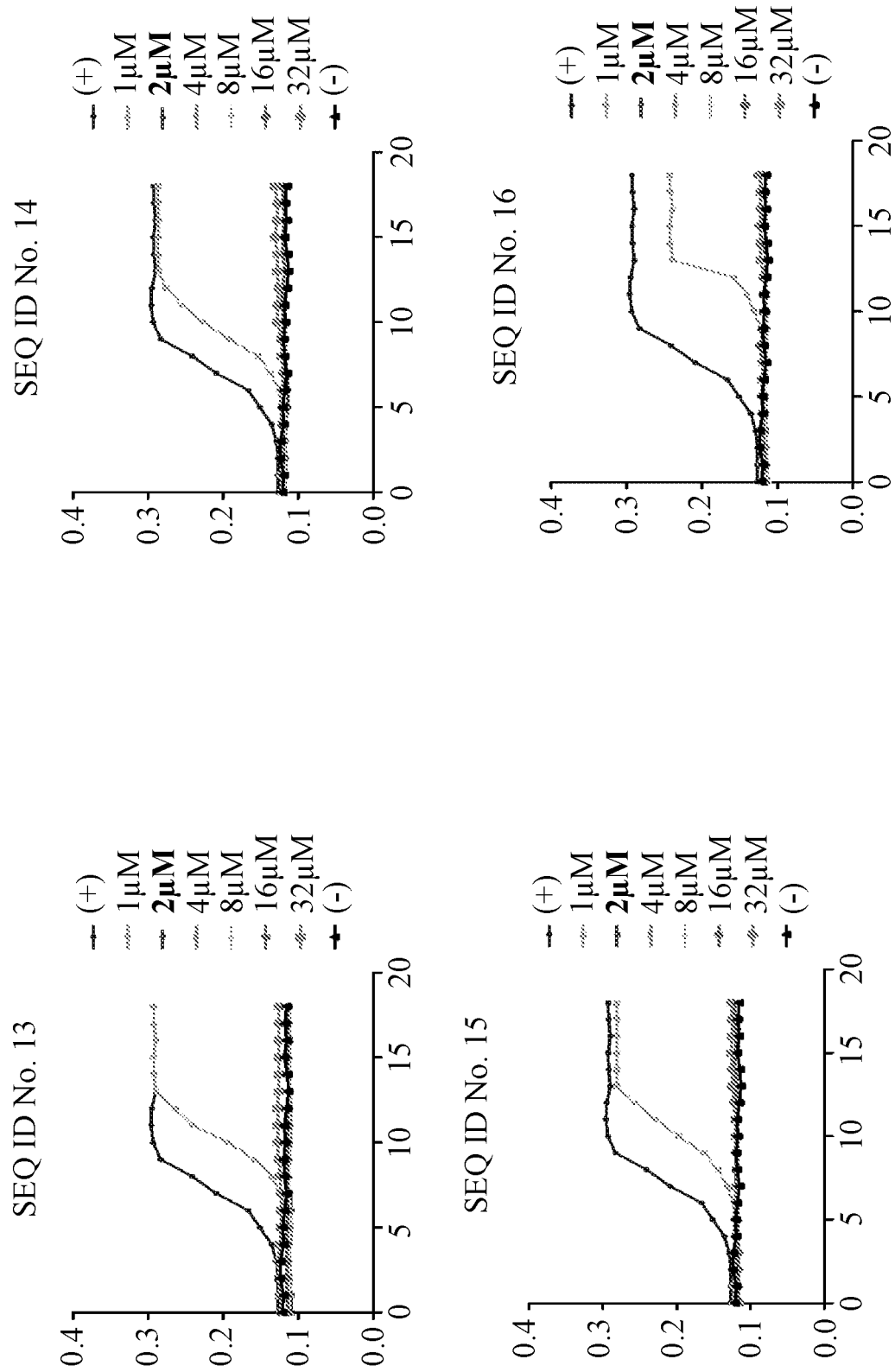
FIG. 6 illustrates the bactericidal activity of 24 amino acid AMP series against *Pseudomonas aeruginosa* (by kinetic bactericidal assay) over time (hours).
Figure 6:
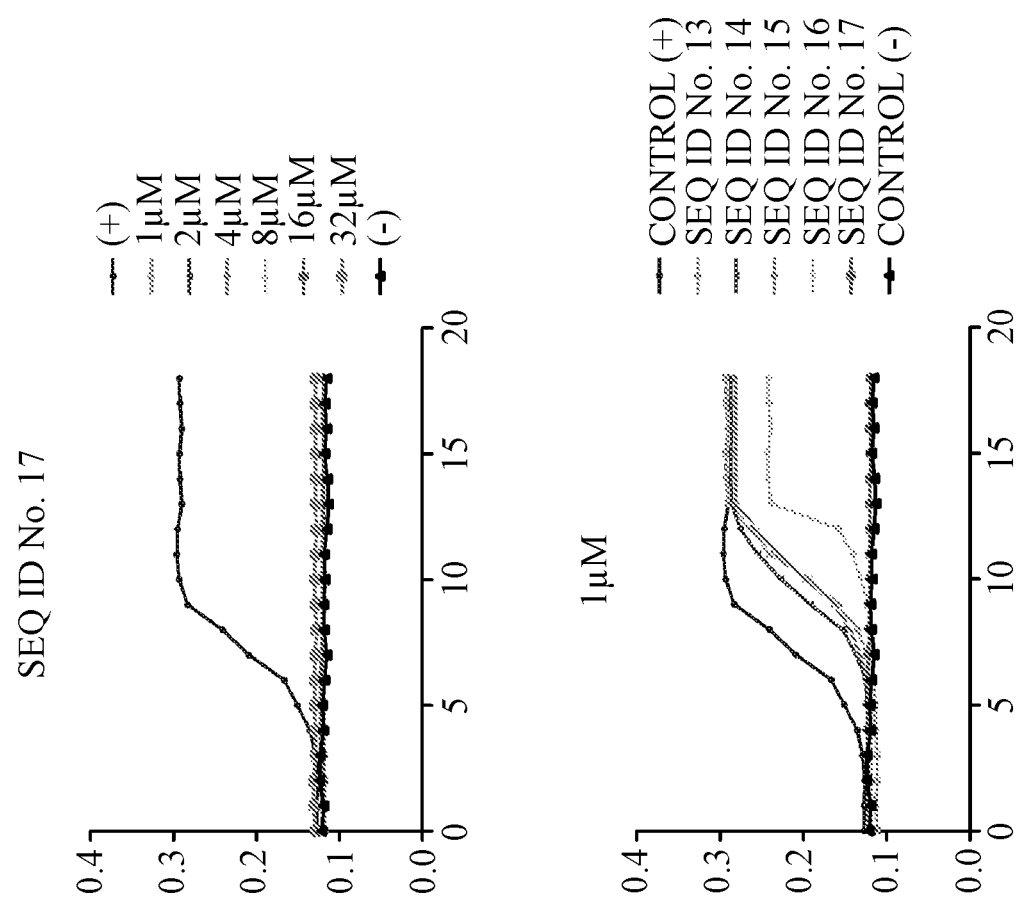

FIG. 6 illustrates the bactericidal activity of the 24 amino acid AMPs series against *Pseudomonas aeruginosa* (by kinetic assay) over time (hours). SEQ ID Nos. 13-17 all demonstrated strong bactericidal activity (MIC=2 uM) against *Pseudomonas aeruginosa*. OD reading, at 570 nm, represents bacterial growth; background reading (~0.05) was subtracted from sample readings. Bolded concentration indicates the determined MIC.

Tables 3 and 4 provide the MIC data for the tested AMPs against a variety of infectious species. The following strains were tested: *Enterococcus faecium* MDR clinical isolates Ef 25153 and Ef 26125; methicillin-resistant *Staphylococcus aureus* (MRSA) clinical isolates USA300 and 150-10; *Klebsiella pneumonia* MDR clinical isolates C3, C5, A5, D7 and E6; and *Pseudomonas aeruginosa* MDR clinical isolates PA 82-8 and PA 129-5. A MIC of >32 indicated that the tested peptide does not kill the infectious species. Table 5 provides the data for the D-amino acid substituted AMPs and their bactericidal activities against various *Klebsiella pneumonia* multi-drug resistant (MDR) clinical isolates. All odd number Kp bacteria (isolated prior to colistin treatment; colistin sensitive) are paired with the corresponding even number Kp bacteria (isolated after colistin treatment; colistin resistant) from the same patient. O.D. readings represent the bacterial growth with a background reading of about 0.049+/−0.003. SEQ ID No. 26 and SEQ ID No. 34 displayed the strongest bactericidal activity with no bacterial growth. There was minimal bacterial growth of some Kp strains (n=7) treated by SEQ ID No. 33 while only 2 Kp isolated showed minimal bacterial growth.

Disclosed herein are novel cationic AMPs with broad-spectrum activity against diverse gram-positive and gram-negative drug-resistant pathogens. The described AMPs are also capable of killing drug resistant bacteria at very low concentrations (as low as 1 µM, which is better than SEQ ID No. 26 (WLBU2) and SEQ ID No. 25 (LL37)).

TABLE 3

MIC (µM) data for Control Peptides and Alpha4 for each infectious species listed

| Peptide Name | Ef 25153 | Ef 26125 | MRSA USA300 | MRSA 150-10 | C3 | C5 | A5 | D7 | E6 | PA 82-8 | PA 129-5 |
|---|---|---|---|---|---|---|---|---|---|---|---|
| SEQ ID No. 26 | <4 | <4 | <4 | 8 | 16 | 16 | >8 | <4 | <4 | 4 | <4 |
| SEQ ID No. 34 | <4 | <4 | <4 | 16 | 8 | 8 | >8 (~10) | <4 | <4 | >8 | 2 |
| SEQ ID No. 33 | <4 | <4 | <4 | 16 | >8 | 8 | >8 | <4 | <4 | >8 | 4 |
| SEQ ID No.32 | <4 | <4 | <4 | 8 | 4 | 4 | >8 | <4 | <4 | >8 | <4 |
| Colistin | <16 | <16 | <16 | <16 | >32 | >32 | >32 | <16 | <16 | <16 | <16 |
| SEQ ID No. 25 | <16 | <16 | >32 | 32 | 32 | >32 | >32 | <16 | <16 | 32 | 16 |
| SEQ ID No. 1 | >32 | >32 | >32 | >32 | >32 | >32 | >32 | >32 | >32 | >32 | >32 |
| SEQ ID No. 24 | >32 | 16 | >32 | >32 | 32 | Not tested | 32 | <16 (~8) | <16 (~8) | >32 | <16 |

TABLE 4

MIC (μM) data for AMPs for each infectious species listed

| Peptide Name | Ef 25153 | Ef 26125 | MRSA USA300 | MRSA 150-10 | C3 | C5 | A5 | D7 | E6 | PA82 82-8 | PA 129-5 |
|---|---|---|---|---|---|---|---|---|---|---|---|
| SEQ ID No. 13 | <16 | <8 | <8 | >16 (~20) | >16 | 16 | >16 | <8 | <8 | 16 | <16 |
| SEQ ID No. 14 | <2 | <2 | <2 | <2 | <2 | 4 | >4 | <2 | <2 | <2 | <2 |
| SEQ ID No. 15 | 2 | <1 | 4 | 2 | <2 | 4 | >4 | 2 | 2 | 2 | 1 |
| SEQ ID No. 16 | <2 | <2 | <2 | 4 | <2 | 4 | >4 | <2 | <2 | 4 | 4 |
| SEQ ID No. 17 | <2 | <2 | <2 | <2 | <2 | 4 | >4 | <2 | <2 | 4 | <2 |
| SEQ ID No. 19 | <2 | <2 | <2 | <1 | <2 | Not tested | <2 | <2 | <2 | 8 | <1 |
| SEQ ID No. 3 | 16 | 16 | <32 | <32 | >32 | >32 | 32 | <32 (~16) | <32 (~16) | >32 | >32 |
| SEQ ID No. 4 | >4 | <2 | >4 | >4 | >4 | 4 | >4 | <2 | >4 | >4 | 4 |
| SEQ ID No. 5 | >4 | <2 | >4 | >4 | 4 | 2 | >4 | <1 | 4 | >4 | <1 |
| SEQ ID No. 6 | >4 | <1 | >4 | <2 | 4 | 4 | >4 | 4 | 4 | >4 | >4 |
| SEQ ID No. 7 | >4 | <2 | <2 | <2 | <2 | 4 | >4 (~5) | <2 | <2 | 2 | <2 |
| SEQ ID No. 8 | >4 | <2 | <2 | 4 | <2 | 4 | >4 | <2 | <2 | >4 | <2 |
| SEQ ID No. 9 | <2 | <2 | <2 | <2 | <2 | 4 | >4 | <2 | <2 | >4 | >4 |

TABLE 5

O.D. readings for AMPs against various *Klebsiella* pneumonia

| Kp Strain Bacteria | SEQ ID No. 26 | SEQ ID No. 32 | SEQ ID No. 33 | SEQ ID No. 34 |
|---|---|---|---|---|
| 1 | 0.308 | 0.047 | 0.039 | 0.104 | 0.043 |
| 2 | 0.192 | 0.047 | 0.044 | 0.108 | 0.048 |
| 3 | 0.224 | 0.048 | 0.043 | 0.048 | 0.051 |
| 4 | 0.223 | 0.048 | 0.042 | 0.047 | 0.051 |
| 5 | 0.366 | 0.048 | 0.042 | 0.053 | 0.05 |
| 6 | 0.183 | 0.055 | 0.107 | 0.12 | 0.062 |
| 7 | 0.367 | 0.048 | 0.042 | 0.046 | 0.049 |
| 8 | 0.318 | 0.048 | 0.04 | 0.056 | 0.047 |
| 9 | 0.328 | 0.049 | 0.042 | 0.043 | 0.045 |
| 10 | 0.33 | 0.048 | 0.048 | 0.131 | 0.05 |
| 11 | 0.327 | 0.048 | 0.048 | 0.057 | 0.051 |
| 12 | 0.333 | 0.049 | 0.05 | 0.066 | 0.053 |
| 13 | 0.319 | 0.048 | 0.048 | 0.05 | 0.05 |
| 14 | 0.329 | 0.048 | 0.047 | 0.089 | 0.05 |
| 15 | 0.391 | 0.052 | 0.048 | 0.048 | 0.049 |
| 16 | 0.351 | 0.087 | 0.045 | 0.054 | 0.045 |
| 17 | 0.388 | 0.061 | 0.045 | 0.044 | 0.042 |
| 18 | 0.586 | 0.049 | 0.047 | 0.048 | 0.046 |
| 19 | 0.306 | 0.046 | 0.048 | 0.049 | 0.048 |
| 20 | 0.307 | 0.051 | 0.049 | 0.05 | 0.051 |
| 21 | 0.291 | 0.05 | 0.051 | 0.048 | 0.049 |
| 22 | 0.295 | 0.046 | 0.048 | 0.05 | 0.049 |
| 23 | 0.287 | 0.046 | 0.048 | 0.047 | 0.048 |
| 24 | 0.278 | 0.047 | 0.11 | 0.076 | 0.05 |

Example 2

Anti-Inflammatory Activity

Anti-inflammatory activity is based on the determination of cytokine stimulation of major inflammatory (e.g. TNF) or anti-inflammatory (e.g., IL-10) cytokines. For in vitro studies, TNF is measured using culture medium from LPS-stimulated macrophage cultures in the presence or absence of peptide treatment. For in vivo studies, cytokine levels in bronchoalveolar lavage (BAL) fluid were quantified using the mouse cytokine multiplex panel assay (Milliplex; Millipore, Billerica, Mass.). The expressions of cytokines were analyzed using the Luminex assay system, based on manufacturer's instructions and our previous publication. Standard recombinant protein solution was used to generate a standard curve for each analyzed protein. Absolute cytokine concentrations were calculated from the standard curve for each cytokine.

Figure 7:
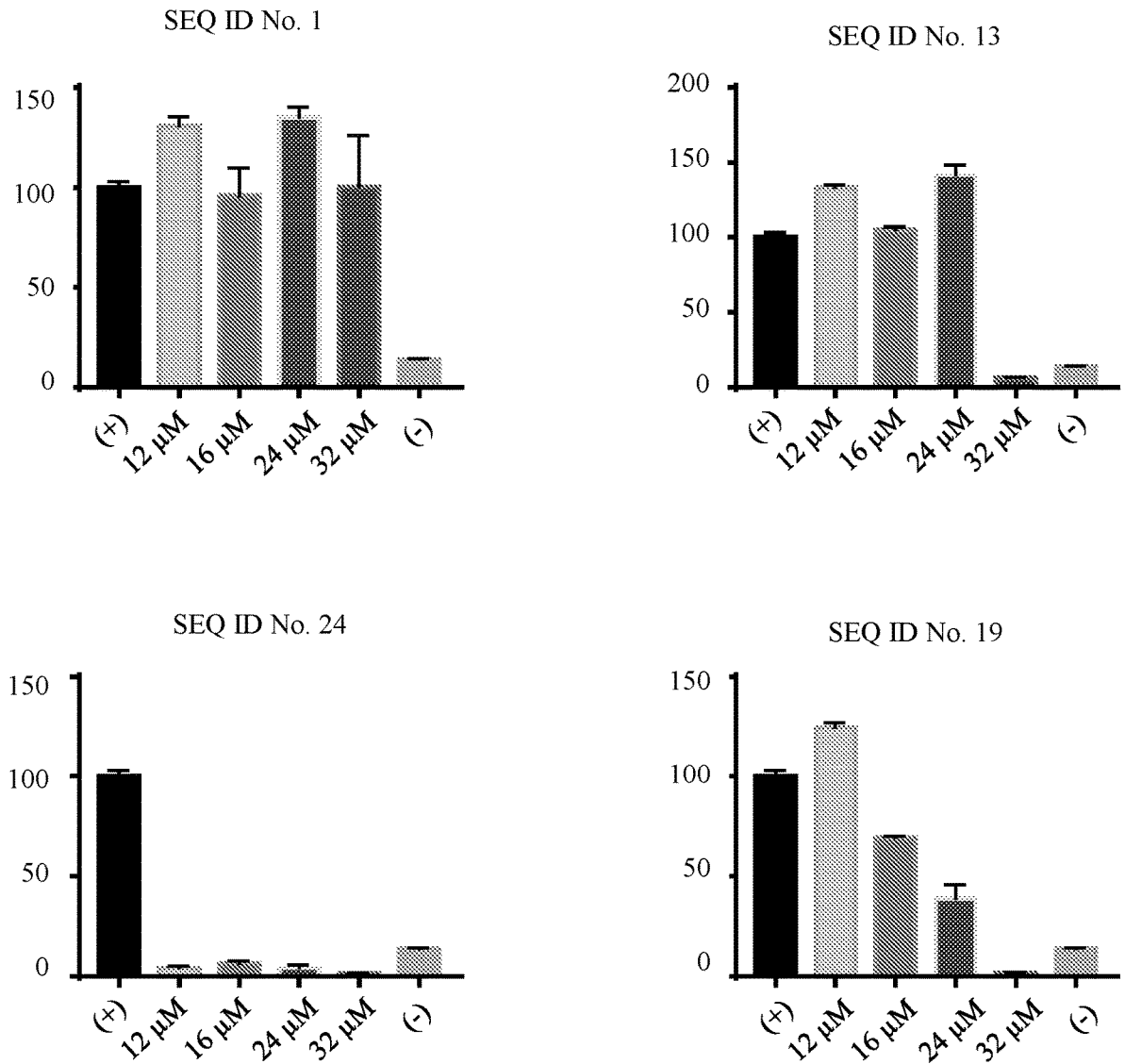
FIG. 7 demonstrates that 24 amino acid AMPs (SEQ ID Nos. 13, 19, 24) Display Neutralizing Activities Against *P. aeruginosa* Lipopolysaccharide (LPS)-Induced Secretion of Tumor Necrosis Factor (TNF) in Raw (264.7) Cells.

FIG. 7 demonstrates that modified AMPs (SEQ ID No. 1, SEQ ID No. 13, SEQ ID No. 19, and SEQ ID No. 24) display neutralizing activities against *P. aeruginosa* lipopolysaccharide (LPS)-induced secretion of tumor necrosis factor (TNF) in Raw (264.7) Cells. A high dosage (1 μg/ml) of LPS was used to stimulate the TNF secretion in raw cells. SEQ ID No. 16 and SEQ ID No. 19 displayed good activity in neutralizing the LPS-induced TNF secretion.

Figure 8:
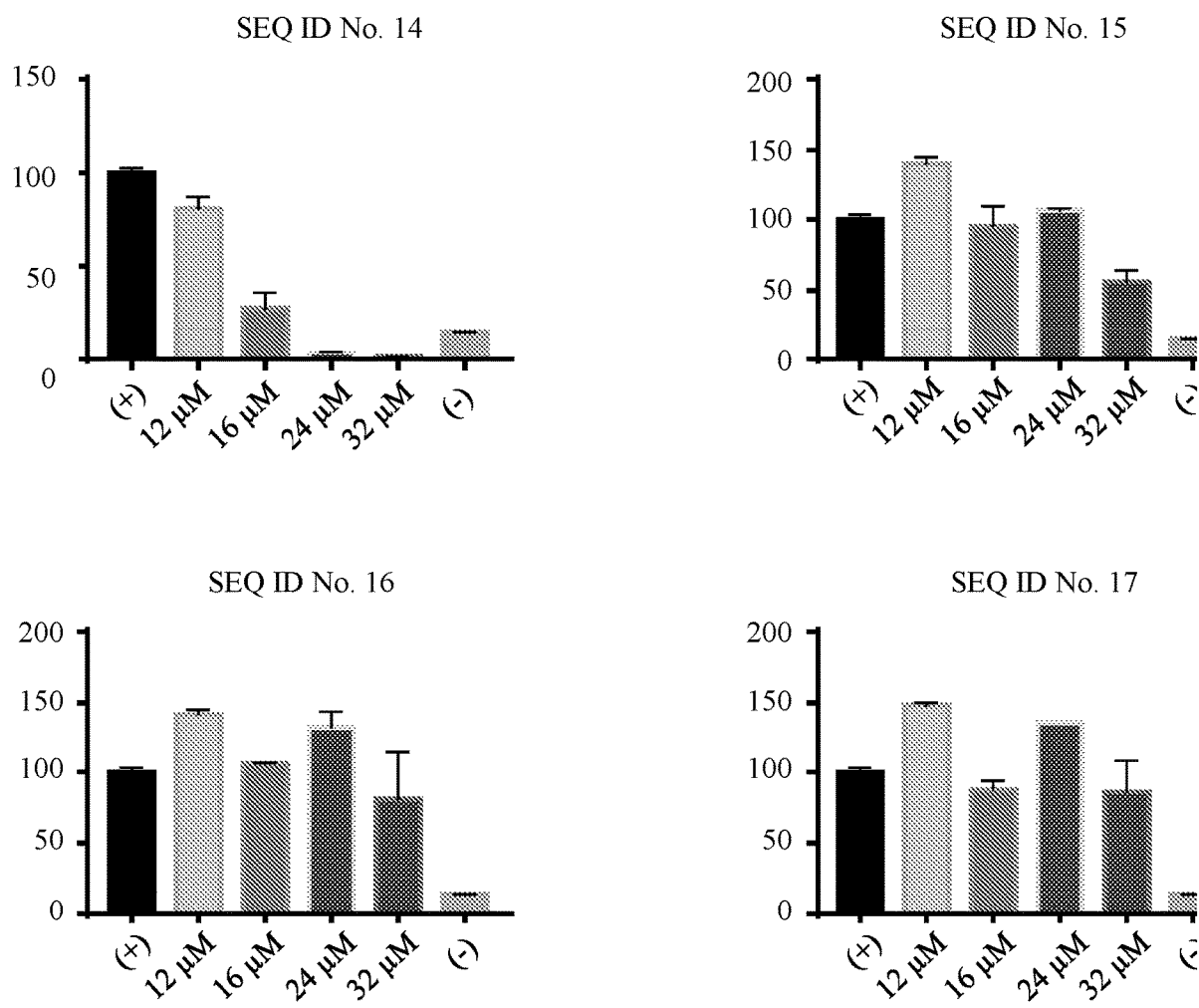
FIG. 8 demonstrates that 24 amino acid AMPs (SEQ ID Nos. 14, 15, 16, 17) Display Neutralizing Activities Against *P. aeruginosa* Lipopolysaccharide (LPS)-Induced Secretion of Tumor Necrosis Factor (TNF) in Raw (264.7) Cells.

FIG. 8 demonstrates that modified AMPs (SEQ ID No. 14, SEQ ID No. 15, SEQ ID No.16, and SEQ ID No. 17) neutralizing activities against *P. aeruginosa* lipopolysaccharide (LPS)-induced secretion of tumor necrosis factor (TNF) in Raw (264.7) Cells. A high dosage (1 μg/ml) of LPS was used to stimulate the TNF secretion in raw cells. SEQ ID No. 14 displayed good activity in neutralizing the LPS-induced TNF secretion.

Figure 9:
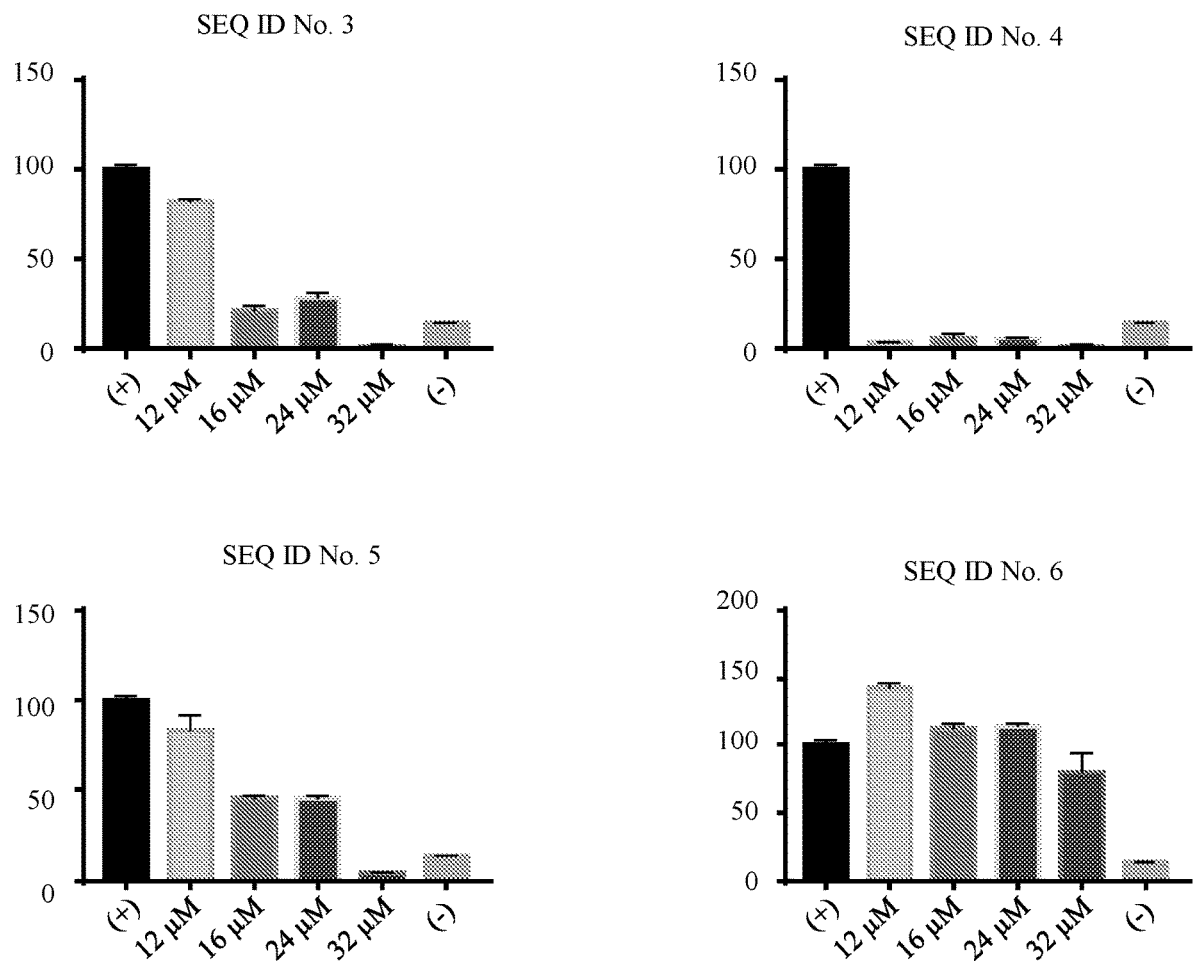
FIG. 9 demonstrates that 30 amino acid AMPs (SEQ ID Nos. 3, 4, 5, 6) display Neutralizing Activities Against *P. aeruginosa* Lipopolysaccharide (LPS)-Induced Secretion of Tumor Necrosis Factor (TNF) in Raw (264.7) Cells.

FIG. 9 demonstrates that modified AMPs (SEQ ID No. 3, SEQ ID No. 4, SEQ ID No. 5, and SEQ ID No. 6) display neutralizing activities against *P. aeruginosa* lipopolysaccharide (LPS)-induced secretion of tumor necrosis factor (TNF) in Raw (264.7) Cells. A high dosage (1 μg/ml) of LPS was used to stimulate the TNF secretion in raw cells. SEQ ID No. 3, SEQ ID No. 4, and SEQ ID No. 5 displayed good activity in neutralizing the LPS-induced TNF secretion.

Figure 10:
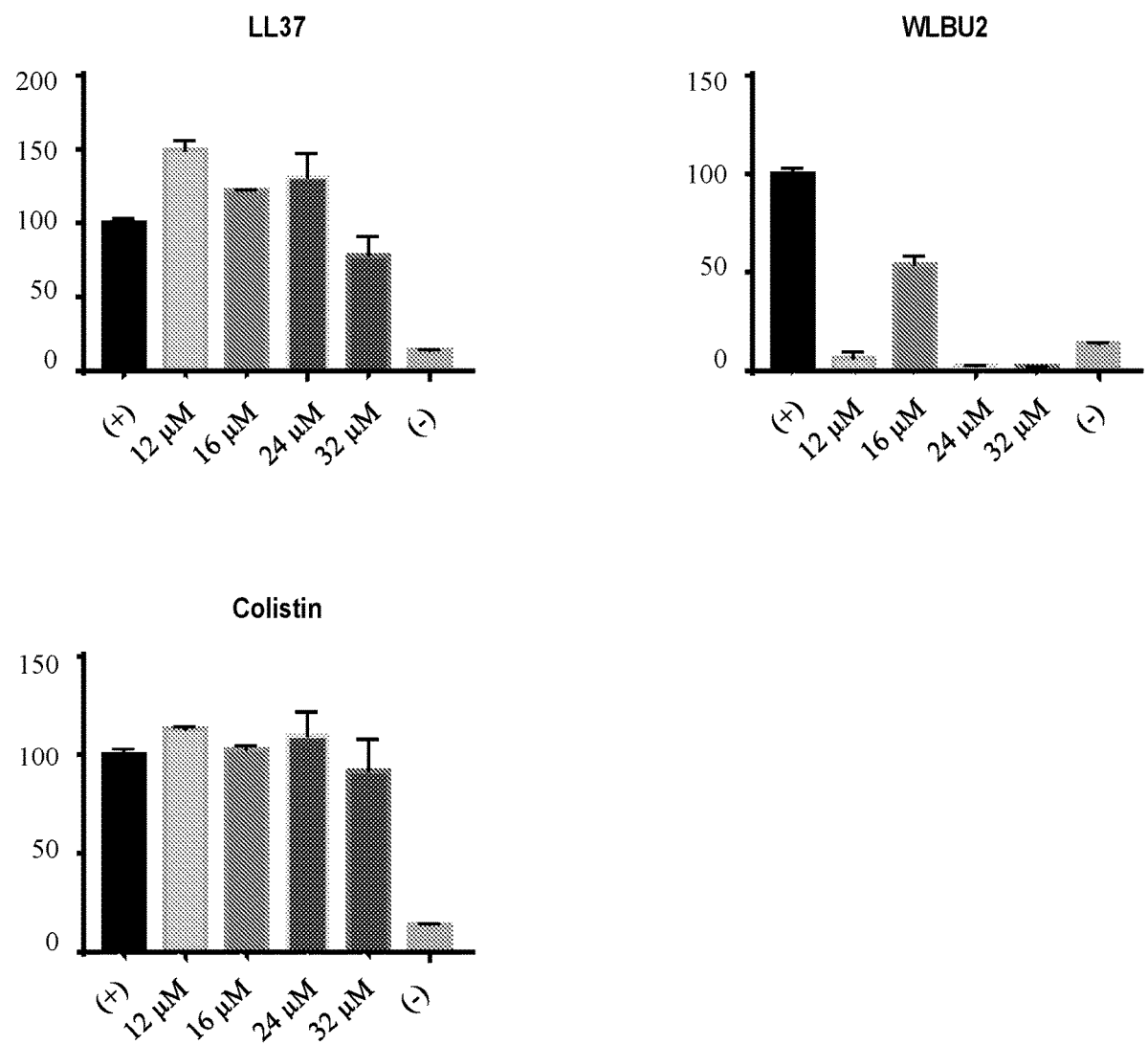
FIG. 10 demonstrates that Colistin and LL37 (SEQ ID No. 25) Do Not Neutralize *P. aeruginosa* Lipopolysaccharide (LPS)-Induced Secretion of Tumor Necrosis Factor (TNF) in Raw (264.7) Cells, while WLBU2 (SEQ ID No. 26) does Neutralize *P. aeruginosa* Lipopolysaccharide (LPS)-Induced Secretion of Tumor Necrosis Factor (TNF) in Raw (264.7) Cells.

FIG. 10 demonstrates that Colistin and LL37 (SEQ ID No. 25) do not neutralize *P. aeruginosa* lipopolysaccharide (LPS)-induced secretion of tumor necrosis factor (TNF) in Raw (264.7) Cells. A high dosage (1 μg/ml) of LPS was used to stimulate the TNF secretion in raw cells. Colistin and LL37 (SEQ ID No. 25) do not possess activity in neutralizing the LPS-induced TNF secretion but WLBU2 (SEQ ID No. 26) does possess activity in neutralizing the LPS-induced TNF secretion.

Accordingly, the cationic antimicrobial peptides described herein have demonstrated anti-inflammatory activity in neutralizing LPS-induced TNF secretion by macrophages.

Example 3

Disruption of Biofilm

Figure 11:
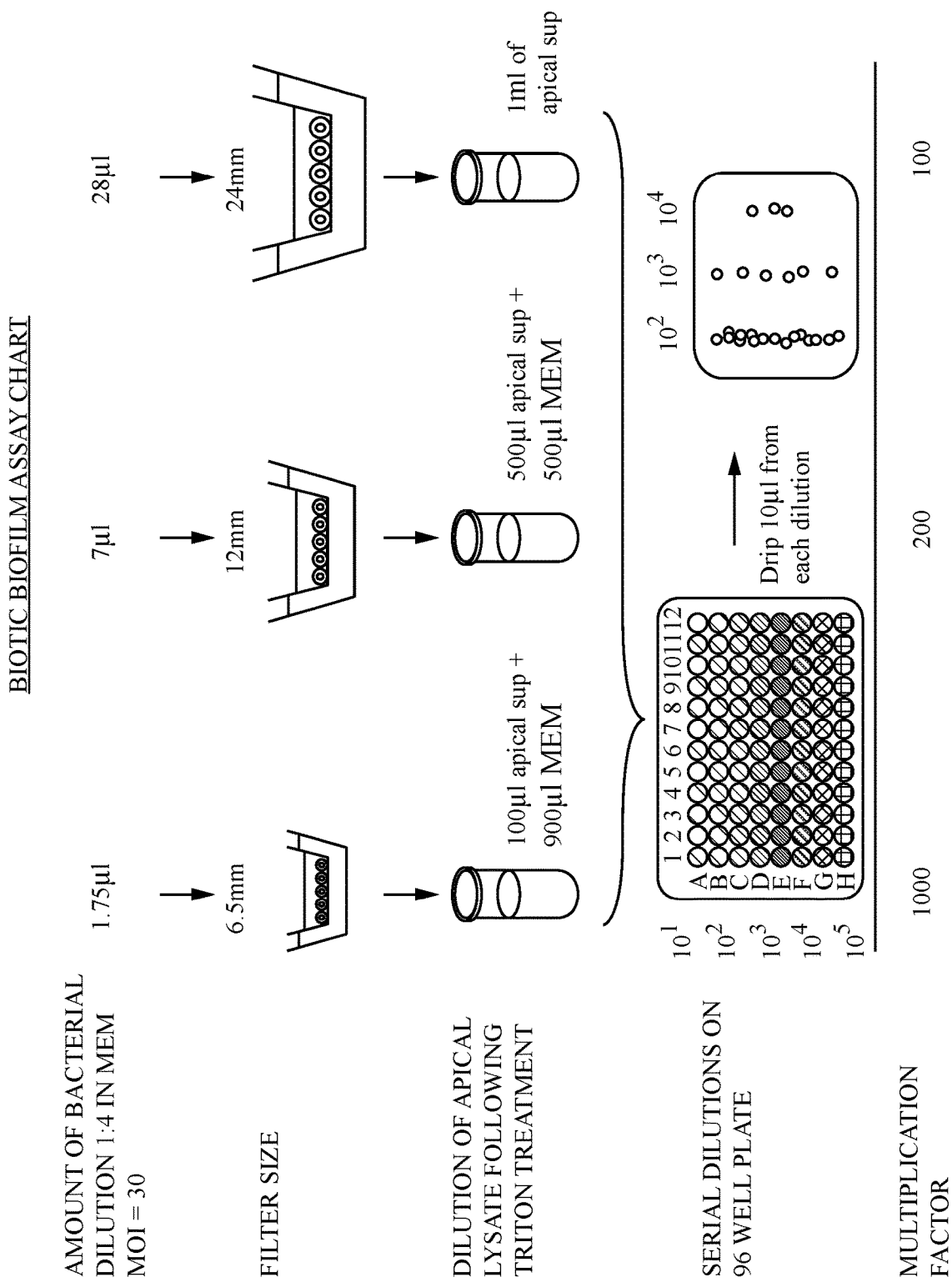
FIG. 11 illustrates the Biotic Biofilm Assay.

The Biotic Biofilm Assay is intended to mimic the conditions in the lungs of healthy subjects and patients with pulmonary diseases such as cystic fibrosis and other disorders where infectious agents are not efficiently removed from the surface of the alveoli. FIG. 11 provides a diagram of the steps involved in the Biotic Biofilm Assay. The Biotic Biofilm Assay is based on bacteria/epithelial cell co-culture model. Primary mouse or human airway epithelial cell (AEC) cultures were established as described in previous publications (Liu, Y., Di, M. E., Chu, H. W., Liu, X., Wang, L., Wenzel, S., and Di, Y. P. (2013) Increased susceptibility to pulmonary *Pseudomonas* infection in Splunc1 knockout mice, J Immunol 191, 4259-4268. Liu, Y., Bartlett, J. A., Di, M. E., Bomberger, J. M., Chan, Y. R., Gakhar, L., Mallampalli, R. K., McCray, P. B., Jr., and Di, Y. P. (2013) SPLUNC1/BPIFA1 contributes to pulmonary host defense against *Klebsiella pneumoniae* respiratory infection, Am J Pathol 182, 1519-1531). Human AEC are extracted from human tissues obtained from UPMC Presbyterian Hospital. For mouse AEC, mice were euthanized and tracheas immediately removed. Tracheal epithelial cells or human AEC were dissociated and seeded onto collagen-coated, semipermeable membranes with a 0.4-μm pore size (Millicell-HA; surface area, 0.6 cm², Millipore, Bedford, Mass.). Cells were maintained in small airway epithelial cell growth medium (Lonza, Allendale, N.J.) and the mucosal medium was removed 24 h after seeding and the cells were allowed to grow and differentiate at the air-liquid interface.

To assess the viability of bacteria, biofilms were grown on polarized and confluent mouse tracheal epithelial cells or human AEC. Bacteria were inoculated on the apical surface of epithelial cells grown on filters (multiplicity of infection of 25). After 1 h of incubation at 37° C., unattached bacteria were removed. Filters containing epithelial cells and the attached bacteria were returned to 37° C. and 5% $CO_2$ for the duration of each experiment (5 h). Arginine was added to the medium to prolong the viability of tracheal epithelial cells incubated with bacteria under static conditions. At the end of the treatment, biofilms remaining at the apical side of airway cells were washed once with minimal Earle's medium, and then 0.1% Triton X-100 was added to the medium for 15 min to lyse the epithelial cells and dissociate the biofilms. The lysate was vortexed for 3 min and serial dilutions were spot titered onto Luria-Bertani plates to determine the CFU per milliliter.

Figure 12A:
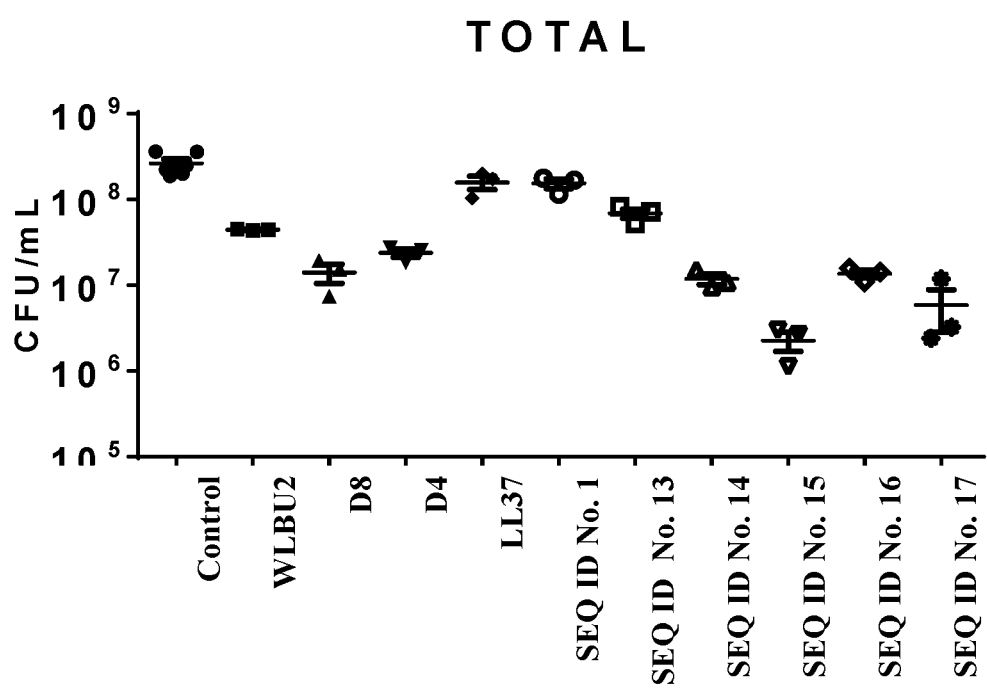
FIG. 12A and FIG. 12B provide the data from 2 separate experiments demonstrating that 24 amino acid AMPs display better anti-biofilm activity (biotic system) than natural AMP LL37 (SEQ ID No. 25) and WLBU2 (SEQ ID No. 26).
Figure 12B:
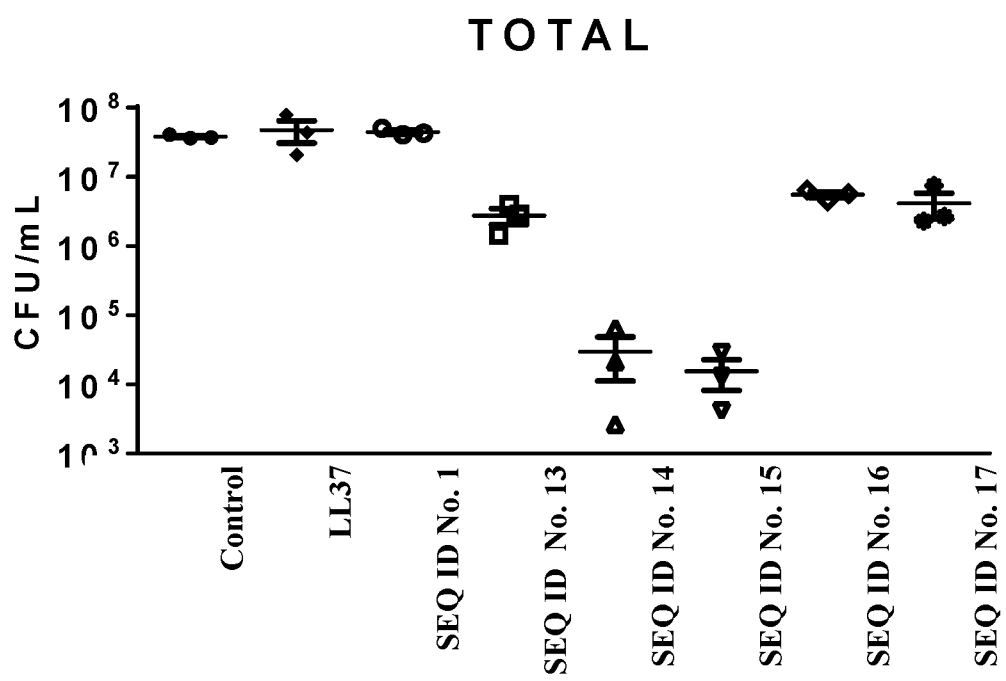

Data from 2 separate experiments, FIGS. 12A and 12B, demonstrate that the modified AMPs display better anti-biofilm activity (biotic system) than natural AMP LL37 (SEQ ID No. 25) and WLBU2 (SEQ ID No. 26). Anti-biofilm properties include the disruption of a biotic biofilm performed in 96-well plates. Sonication causes the release of bacterial cells from the biofilm, CFU/mL is measured for each bacterial dilution. The two separate experiments showed similar results, modified AMPs, SEQ ID No. 13, SEQ ID No. 14, SEQ ID No. 15, SEQ ID No. 16, SEQ ID No. 17, are superior to LL37 (SEQ ID No. 25) and WLBU2 (SEQ ID No. 26) in anti-biofilm activity.

The disclosed cationic AMPs have strong anti-biofilm activity over either WLBU2 (SEQ ID No. 26) or LL37 (SEQ ID No. 25).

Figure 24:
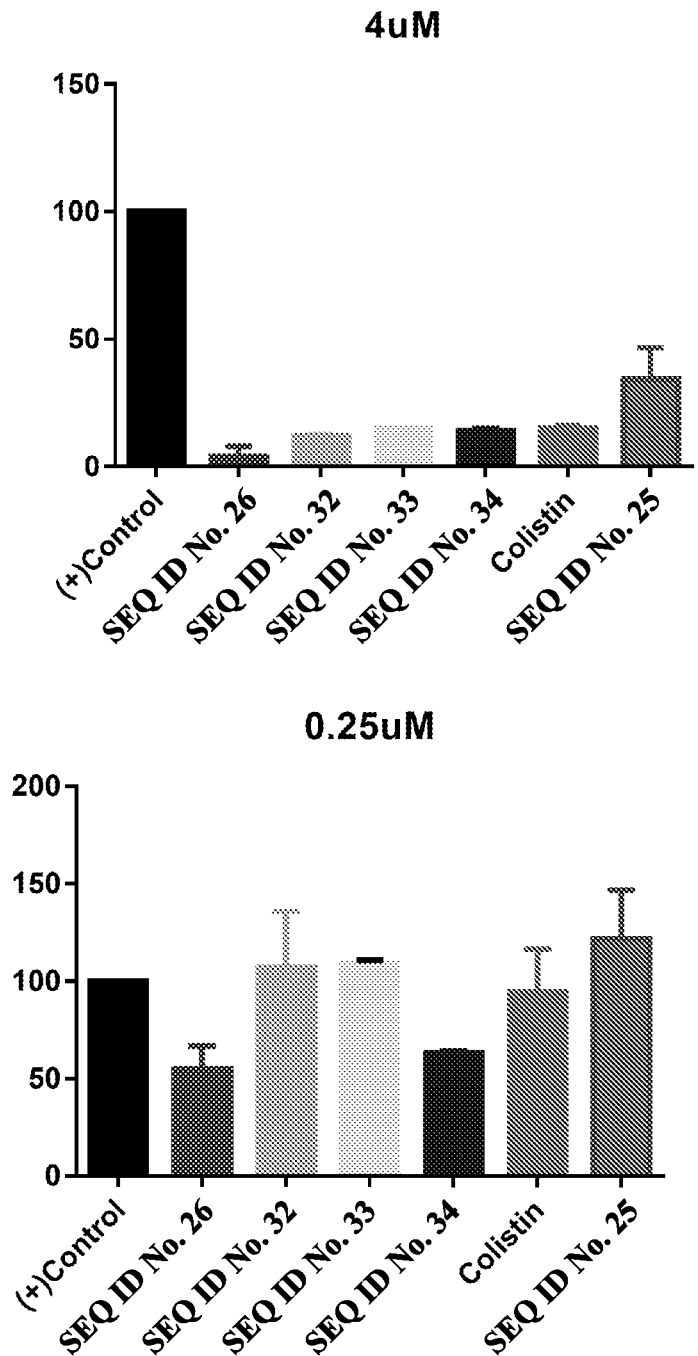
FIG. 24 shows anti-biofilm formation against *P. aeruginosa*.

Further, SEQ ID No. 34 maintains its anti-biofilm activity even at 1/8 MIC concentration (0.25 μM) against *P. aeruginosa*. FIG. 24 provides the results comparing SEQ ID Nos. 25-26, 32-34 and Colistin.

Example 4

Stability in Biological Fluids

Figure 25:
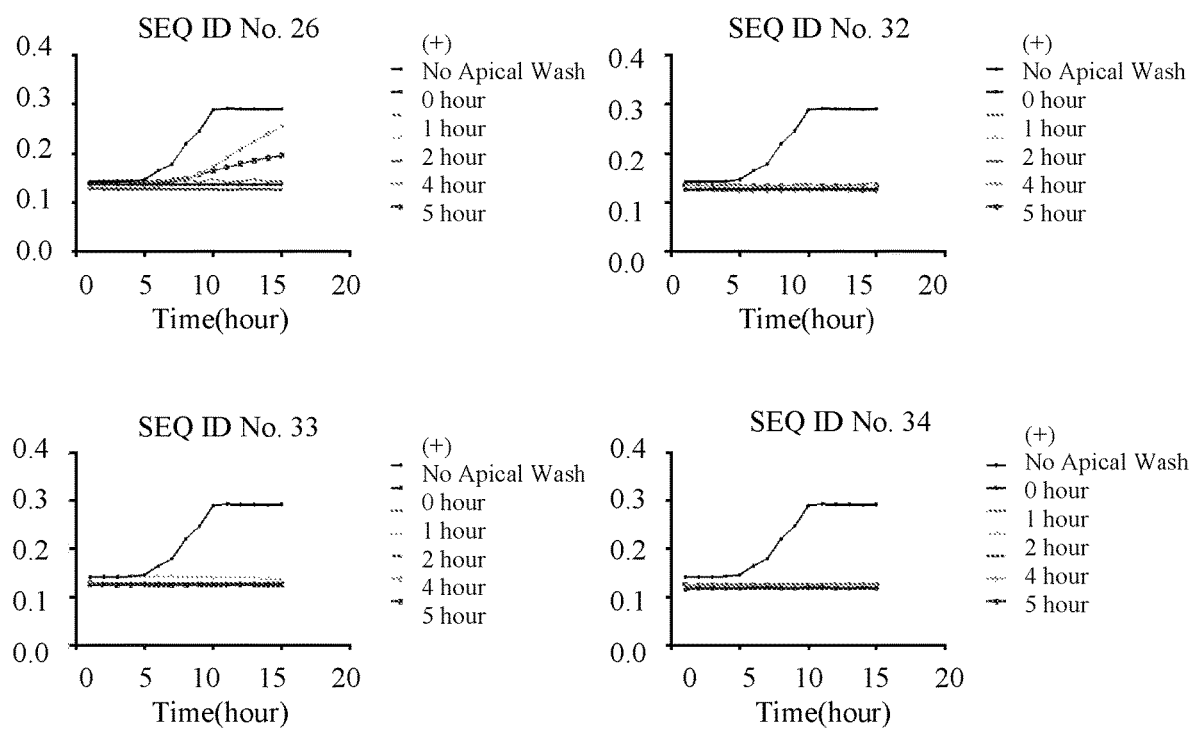
FIG. 25 shows the stability of AMPs in biological fluids at 4 µM.

Apical epithelial secretion is collected from the apical site of air-liquid interface (ALI) cultured primary human epithelial (HBE) cells. Different AMPs were incubated at 4 μM with apical epithelial secretion for different periods of time (as indicated) to determine their stability. There were no bacterial growth in *Pseudomonas aeruginosa* cultures treated with SEQ ID No. 32, SEQ ID No. 33, and SEQ ID No. 34. SEQ ID No. 26 lost part of its bactericidal activity after incubation with apical epithelial secretion. See FIG. 25. The stability may not due to resistance to N.E. digestion because there should be no N.E. in ALI HBE cultured cells. This observation indicates unexpected unique feature of D-WBLU2. These data indicate that the D-amino acid substitutions of WLBU2 unexpectedly increase its antimicrobial activity in addition to enhancing the peptide stability.

Figure 26:
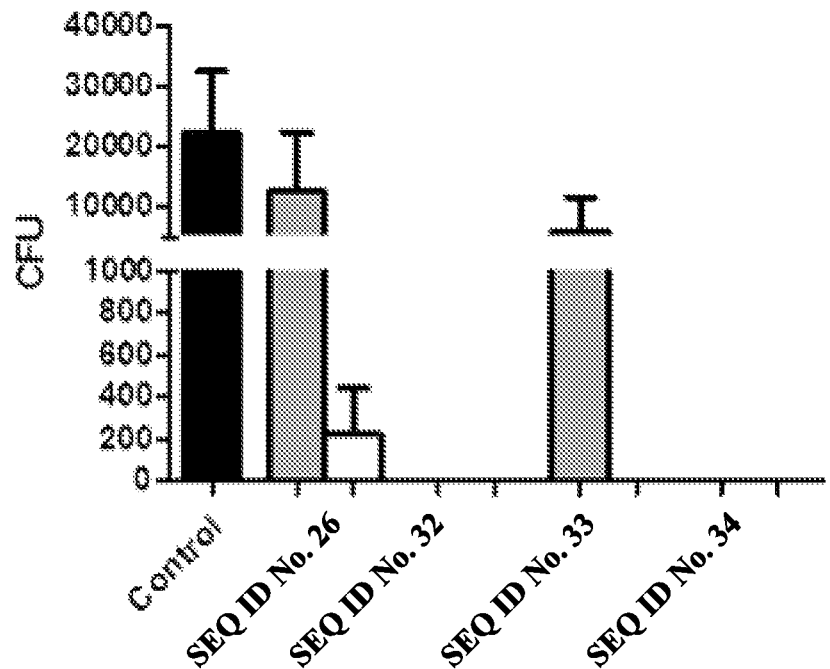
FIG. 26 shows the results of direct bacterial killing assay.
Figure 26:
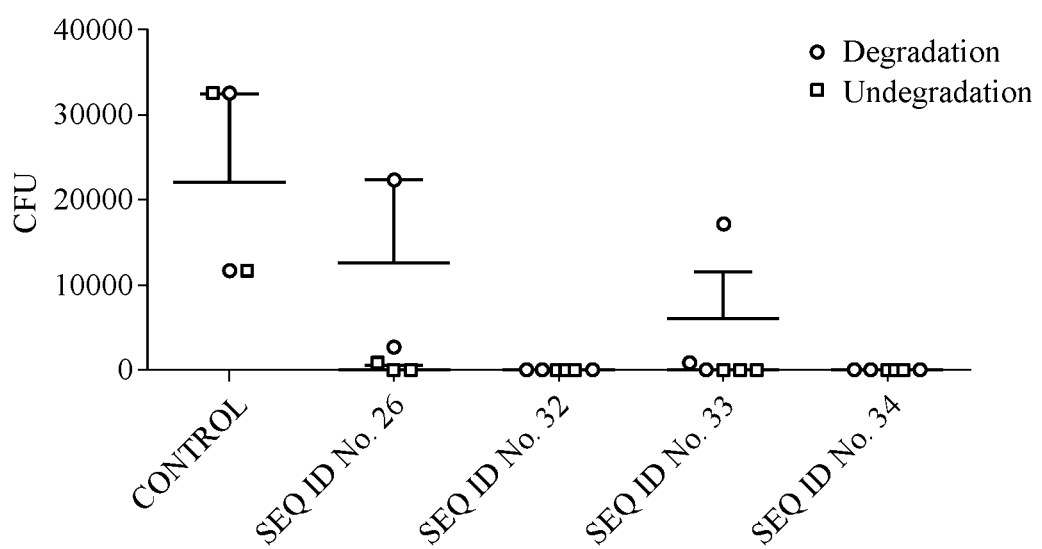

Quantitative results of direct bacterial killing assay shows resistance to apical protease digestion. See FIG. 26. Degradation refers to two hours incubation on the surface of ALI HBE cells, min degradation mean 15 minutes overlay of AMPs to the epithelial cell surface.

Example 5

Toxicity

Figure 13:
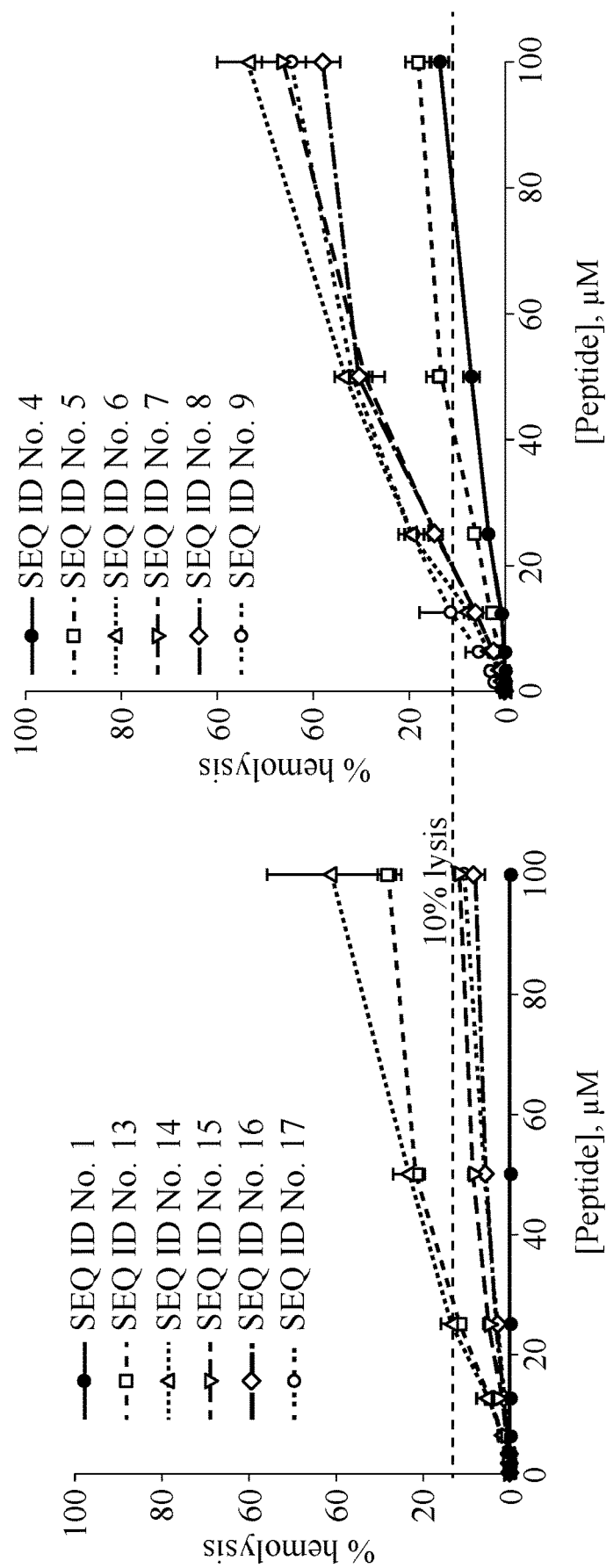
FIG. 13 demonstrates that in Preliminary hemolytic assays AMPs show less toxicity than WLBU2 (SEQ ID No. 26).

Cell toxicity is measured using a hemolytic assay, where the percentage of RBC lysis demonstrates increased toxicity, FIG. 13. The modified AMPs SEQ ID No. 15, SEQ ID No. 16, and SEQ ID No. 17 show less than 10% lysis all the way up to 100 μM. All tested modified AMPs showed 50% or less lysis up to 100 μM. Preliminary hemolytic assays suggested less toxicity than WLBU2 (SEQ ID No. 26).

Figure 14A:
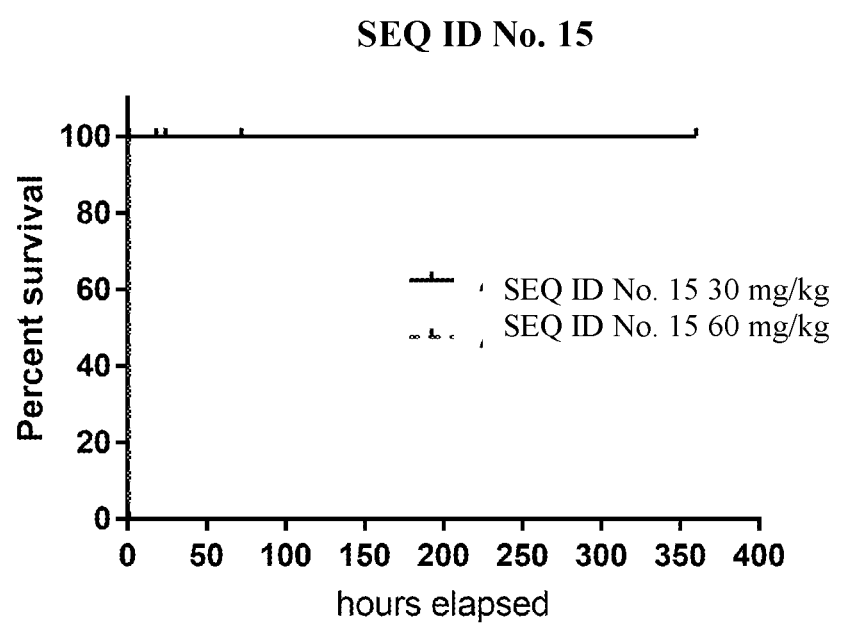
FIG. 14A demonstrates that SEQ ID No. 15 has lower toxicity (higher MTD) than WLBU2 (SEQ ID No. 26).

The modified AMPs show a lower toxicity and higher maximum tolerated dosage (MTD) than WLBU2 (SEQ ID No. 26). The MTD for WLBU2 (SEQ ID No. 26) is 15 mg/kg, for Colistin is 10 mg/kg, and SEQ ID No. 15 is 30 mg/kg (FIG. 14A).

Figure 14B:
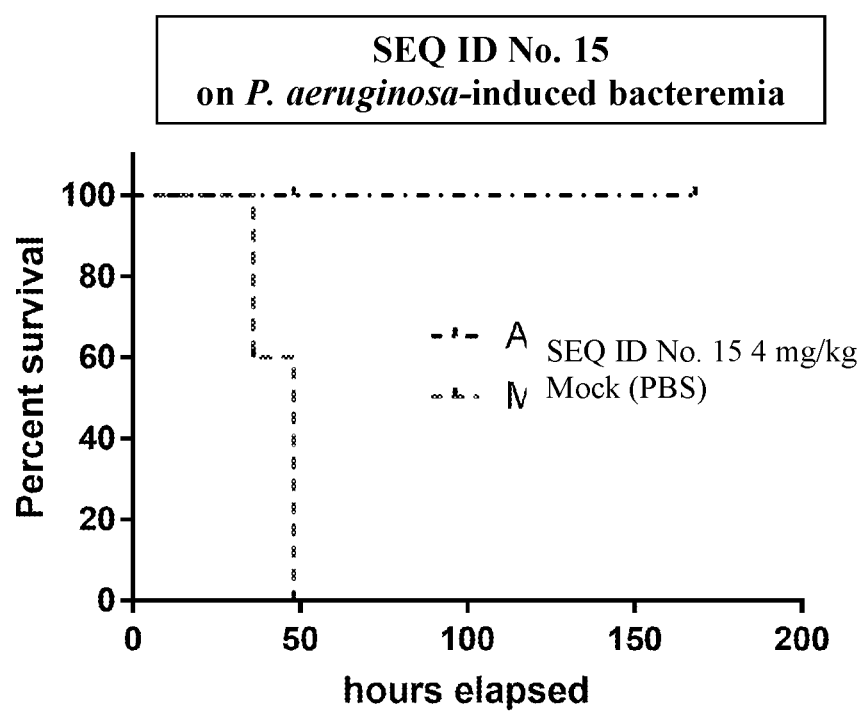
FIG. 14B shows that SEQ ID No. 15 provides excellent protection against bacteremia.

In vivo experiments using IV injection of PAO1 at ~$3\times10^7$ CFU and SEQ ID No. 15 at 4 mg/kg. shows excellent protection against bacteremia (FIG. 14 B).

Disclosed cationic AMPs have lower in vivo toxicity (MTD 30 mg/kg) than WLBU2 (SEQ ID No. 26) (MTD 15 mg/kg), and lower cytotoxicity in vitro than WLBU2 (SEQ ID No. 26).

Figure 27:
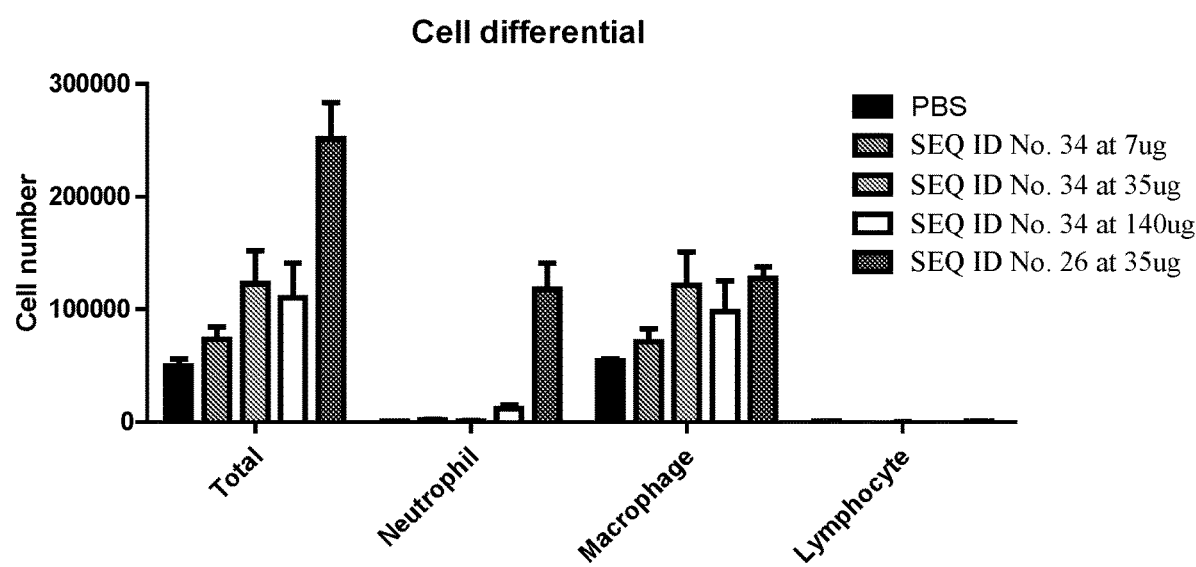
FIG. 27 shows the results of the in vivo pulmonary toxicity test.

Pulmonary toxicity was tested in mouse lung. See FIG. 27. The recruitment of leukocytes (a measure of inflammation) in SEQ ID No. 34 treated mouse lung was significantly lower than SEQ ID No. 26 even at four times the concentration of SEQ ID No. 26. The mice also more active and responsive (to the hand grab) after SEQ ID No. 34 treatment than the SEQ ID No. 26 treatment.

Example 6

Treatment of Primary and Secondary Infections

Figure 15A:
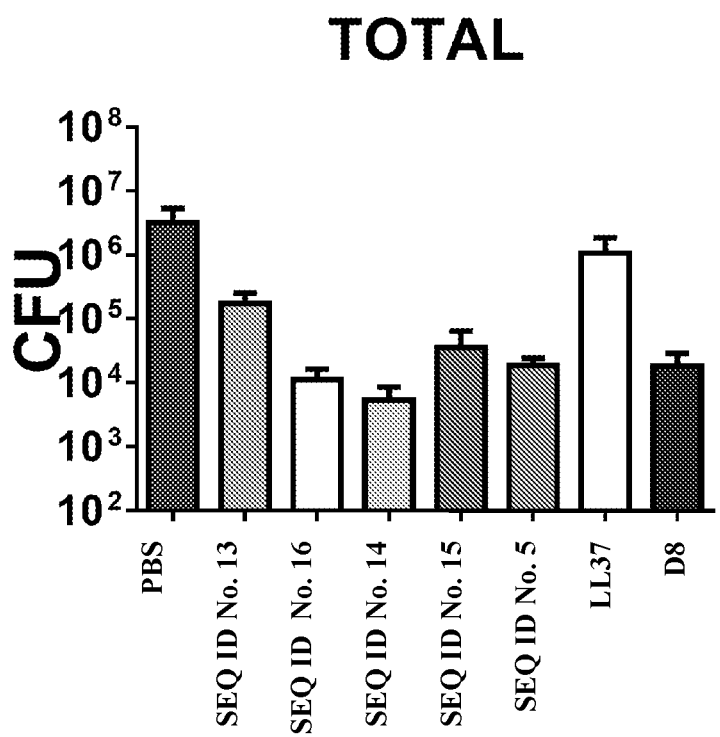
FIG. 15A demonstrates AMPs superior antimicrobial activity compared with LL37 (SEQ ID No. 25) against respiratory *P. aeruginosa* infection.
Figure 15B:
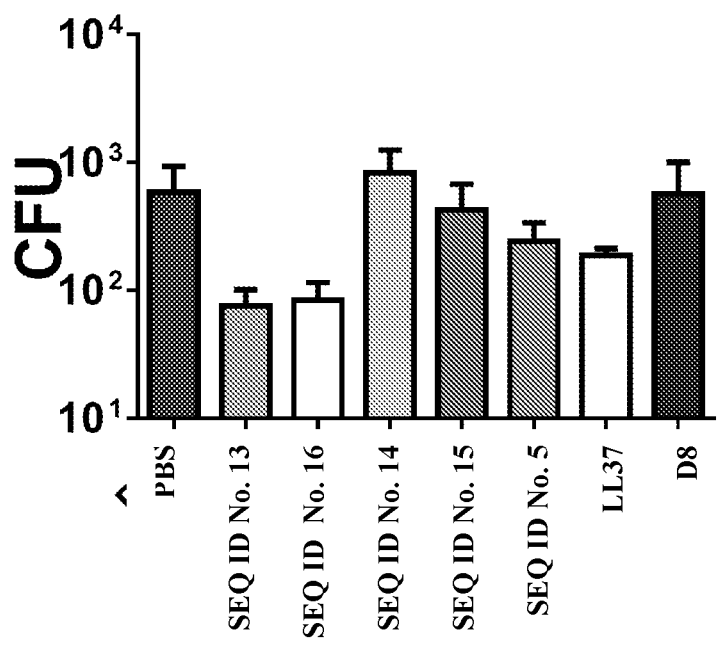
FIG. 15B demonstrates AMPs provide antimicrobial activity in the spleen.

This example illustrates the effect of the modified AMPs on primary respiratory infection and secondary infections. The in vivo experiments used a low dosage bacterial inoculation of P. aeruginosa. AMPs demonstrate superior antimicrobial activity compared with LL37 (SEQ ID No. 25) and D8 (SEQ ID No. 34) against the primary respiratory infection site (FIG. 15A) and the secondary spleen infection site (FIG. 15B).

Figure 16:
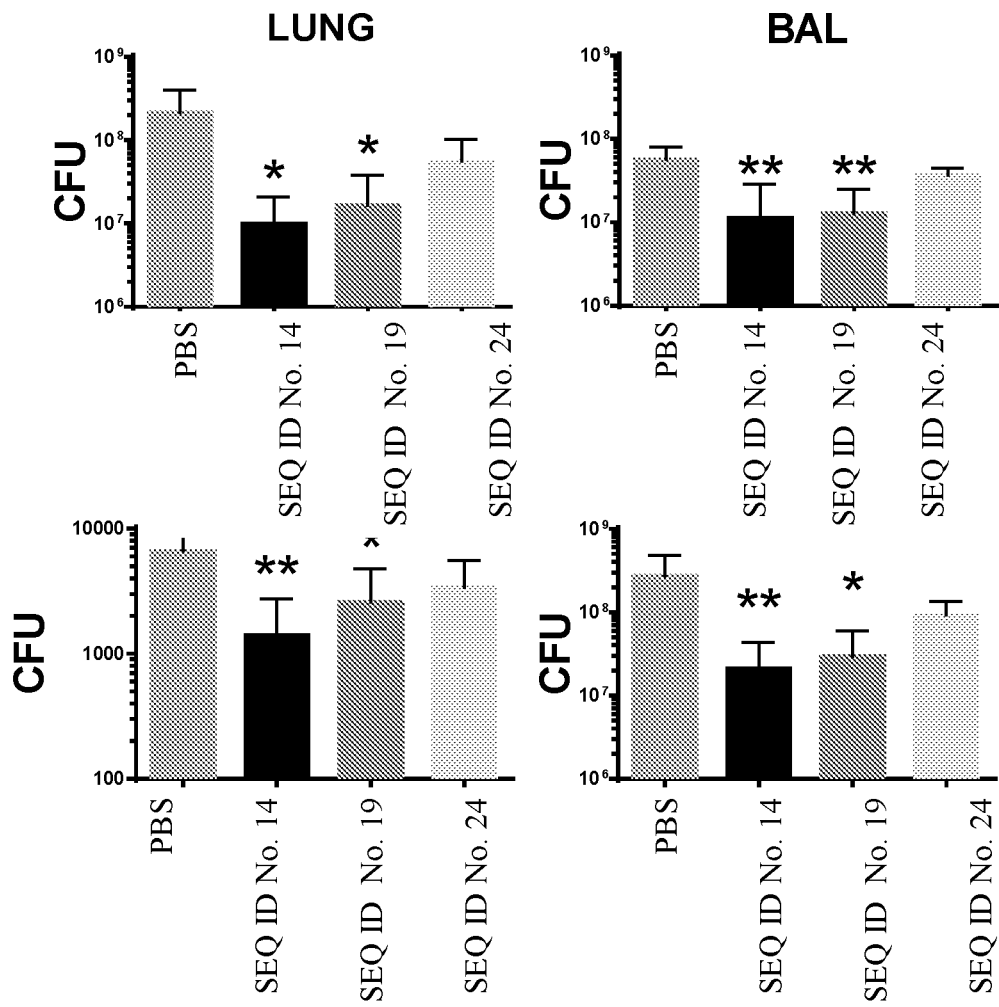
FIG. 16 demonstrates that SEQ ID No. 19 has excellent antimicrobial activity against respiratory *P. aeruginosa* infection.

SEQ ID No. 14 and SEQ ID No. 19 have excellent antimicrobial activity against respiratory P. aeruginosa infection using a high dosage bacterial inoculation (FIG. 16) compared with a negative control.

Disclosed cationic AMPs have strong in vivo efficacy with higher therapeutic index (TI) than WLBU2 (SEQ ID No. 26) and efficacy against respiratory pseudomonas infection (similar to or better than WLBU2 (SEQ ID No. 26) or D8 (SEQ ID No. 34)).

Figure 28:
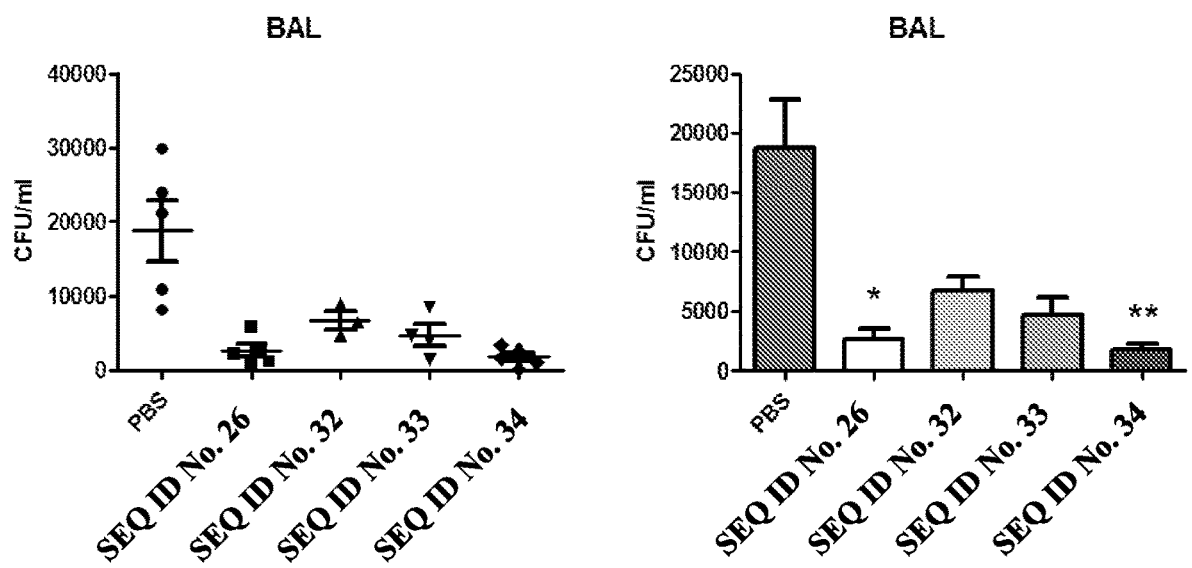
FIG. 28 shows in vivo anti-microbial activity against respiratory infection at 1 µg.
Figure 29:
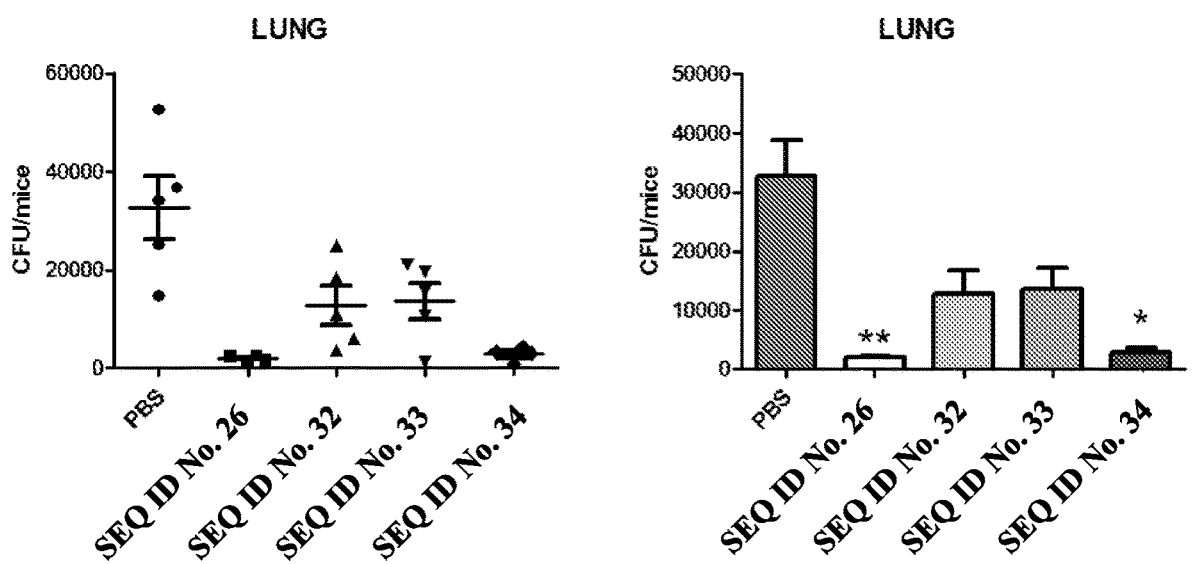
FIG. 29 shows in vivo anti-microbial activity against respiratory infection at 1 µg.

Experiments were also performed with D-amino acid substituted AMPs at 1 μg. See FIGS. 28 and 29.

Example 7

Treatment of Viral Infections

RSV a major cause of lower respiratory tract infection in children and elderly adults, is also a major pathogen frequently associated with asthma exacerbation. Most cases of RSV are not severe, however, in cases of compromised immunity, pre-mature birth or congenital heart disease the infection may lead to hospitalization and sometimes even death. RSV also increases risk of Bronchiolitis and pneumonia. Natural AMPs are short cationic peptides (usually <50 a.a.) that interact with microorganisms to fight against inhaled pathogens and maintain homeostasis of the airways and lung. We have pioneered the development of novel AMPs for the treatment of microbial infections based on computationally engineered cationic AMPs that are sequenced to form optimized amphipathic helices. Our studies to date have characterized the minimum peptide length necessary to achieve optimal in vitro activity against a broad spectrum of microbial pathogens, while minimizing hemolytic and cytotoxic effects. Having been optimized for amphipathicity and positive charge, these novel AMPs possess higher antibacterial activity than the original protein. Thus, AMPs exhibit great potential as new therapeutic agents because of their novel antimicrobial activity mechanism. However, the potential of AMPs to block viral replication remains unknown. The current study explores the anti-viral potential of these AMPs against RSV, which can be extended to activity against all enveloped viruses such as poxvirus, herpesvirus, rhabdovirus, hepadnavirus, baculovirus, orthomyxovirus, paramyxovirus, retrovirus, togavirus, bunyavirus and flavivirus, and other RNA viruses such as Respiratory Syncytial Virus (RSV), measles, mumps, parainfluenza viruses and others.

Research dedicated to combatting RSV takes a pharmaceutical approach by employing immune components such as IFN-gamma against the virus. A proteinic approach has been taken in this study, examining the effects of newly synthesized AMPs on RSV. These AMPs have been enhanced by optimizing amphipathicity and positive charge to yield a sequence which has more potent antibacterial activity. However, the anti-viral characteristics of AMPs are not clearly understood.

In this study, a Hep2 epithelial cell line has been treated with different formulations of an AMP and optimization of dosage was performed.

Figure 17:
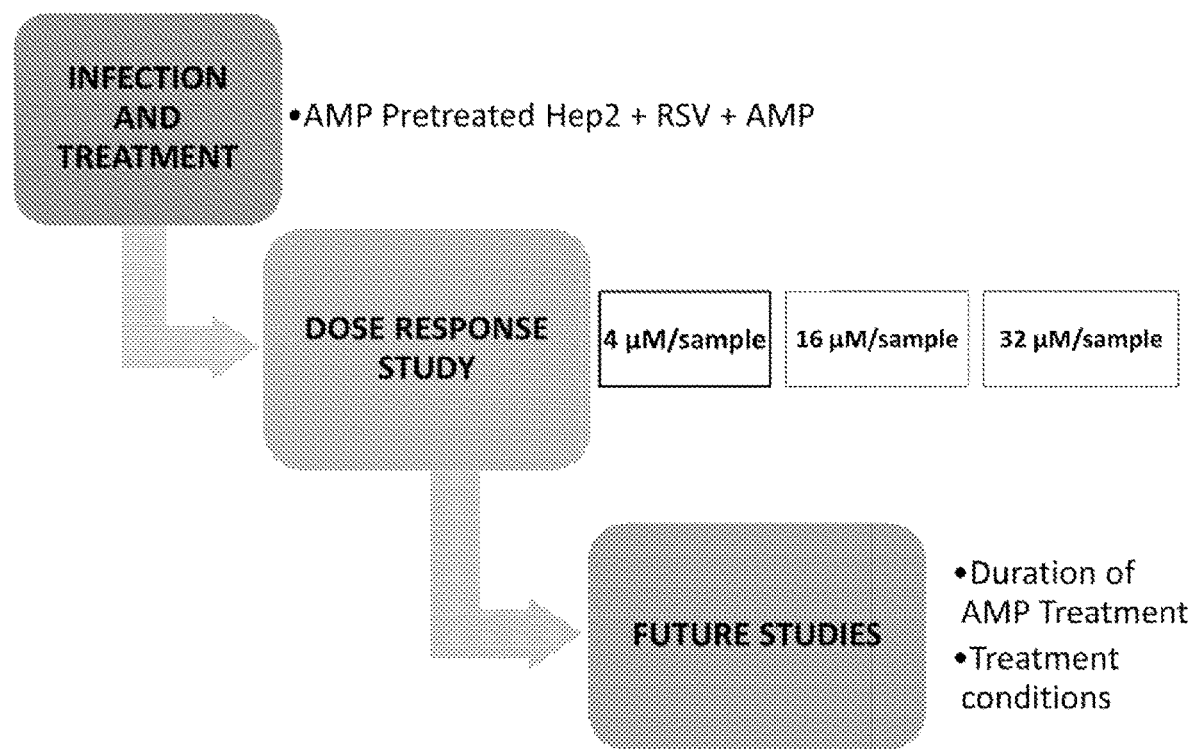
FIG. 17 illustrates the RSV plaque assay used to evaluate whether the AMPs had anti-viral activity against Respiratory Syncytial Virus.

Methods: RSV Plaque Assay (FIG. 17).

Using a standard plaque assay, RSV replication was quantified in permissive Hep2 epithelial cells in the presence or absence of various AMPs. RSV plaque assays were used to determine the minimum dose required to induce Hep2 cytopathology and maximum anti-viral effects. Experimental controls included Hep2 cells+/−RSV and Hep-2 cells with AMP only.

Hep-2 epithelial cells were plated in 12-well plates and allowed to grow to confluency. The cells were pre-treated with the AMP SEQ ID No. 15 at different dosages for an hour. Subsequently the cells were infected with diluted A2 line of RSV (10-5 dilution) for another hour. This was followed by another round of treatment with AMP SEQ ID No. 15. Finally, methylcellulose was added on the cells to contain the infection.

After a 5-day incubation period, the viral infection was quantified by staining the cells with Hematoxylin and Eosin and counting the formed plaques.

Results: Some tested AMPs caused extensive cytopathology at 32 uM. Nonetheless, we found the selected AMPs were able to elicit significant reduction in viral plaques titers with no apparent cytopathology.

Figure 18:
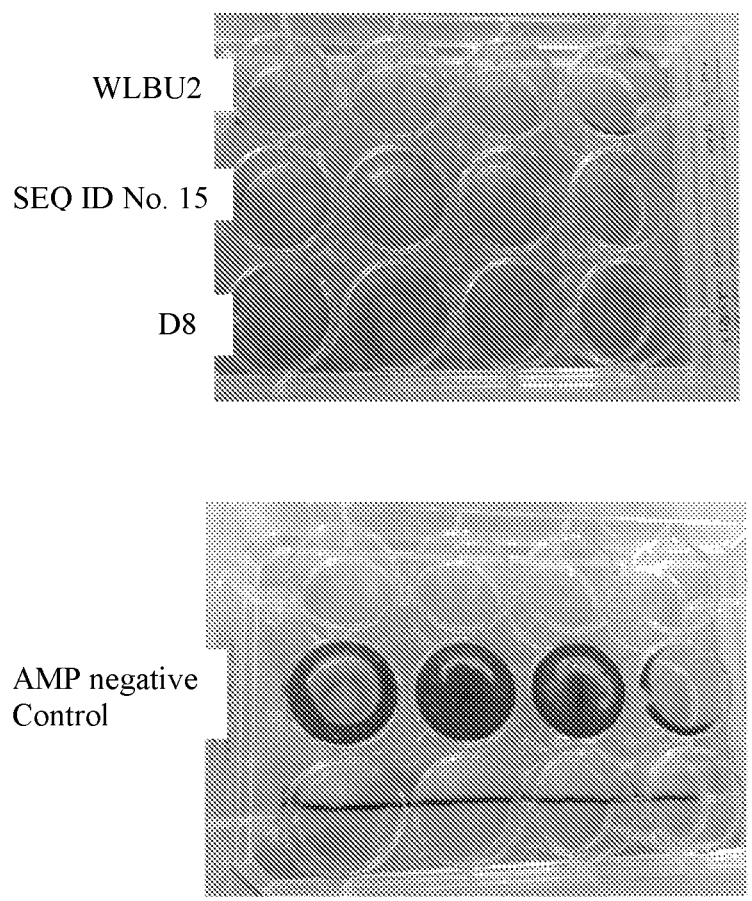
FIG. 18 demonstrates that the 32 µM dosage of AMP SEQ ID No. 15, WLBU2 (SEQ ID No. 26), and D8 (SEQ ID No. 34) all caused cytopathology in the Hep2 cells when compared to the AMP negative control.

32 μM dosage of AMP SEQ ID No. 15 and 26 caused cytopathology in the Hep2 cells when compared to AMP negative control group. Hep2 control cells without the AMP were also plated. Both plates were infected with the same dilution of A2 RSV virus. There is extensive sloughing of cells treated with the peptide (top plate) as compared to cells which were not (bottom plate), FIG. 18. This data suggests that the 32 μM dosage may have been cytotoxic to the cells, therefore causing the sloughing.

Figure 19A:
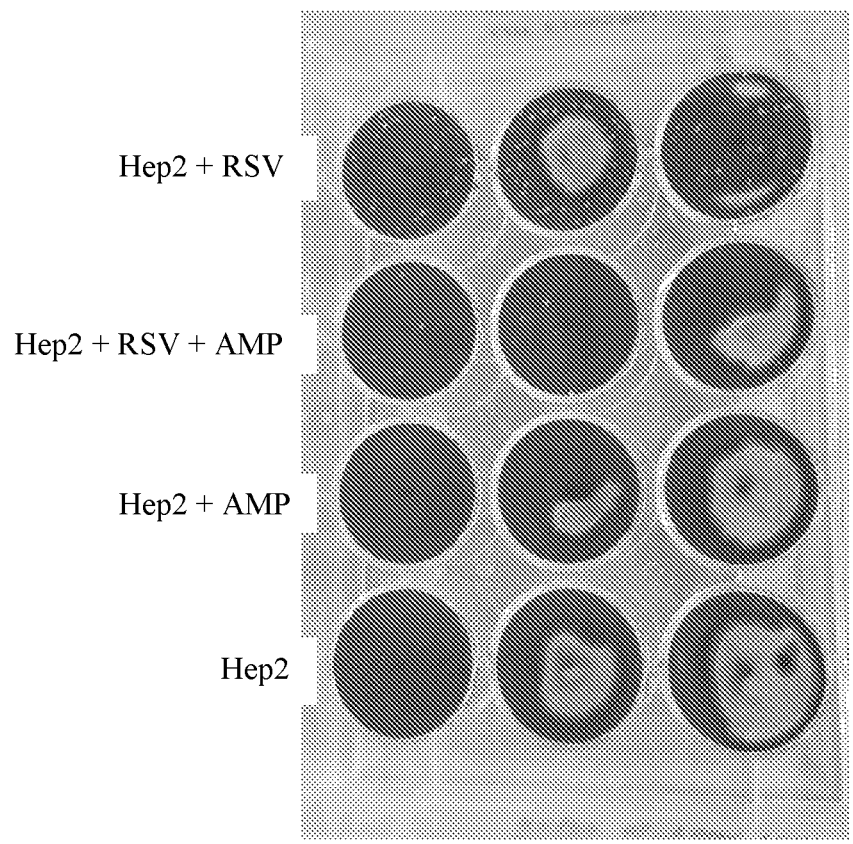
FIG. 19A demonstrates that 4 µM AMP SEQ ID No. 15 has a reduction in the number of plaques compared to a negative control FIG. 19B demonstrates that 16 µM AMP SEQ ID No. 15 reduces viral plaque formation to a greater extent when compared to both a negative control and the 4 µM dosage.
Figure 19B:
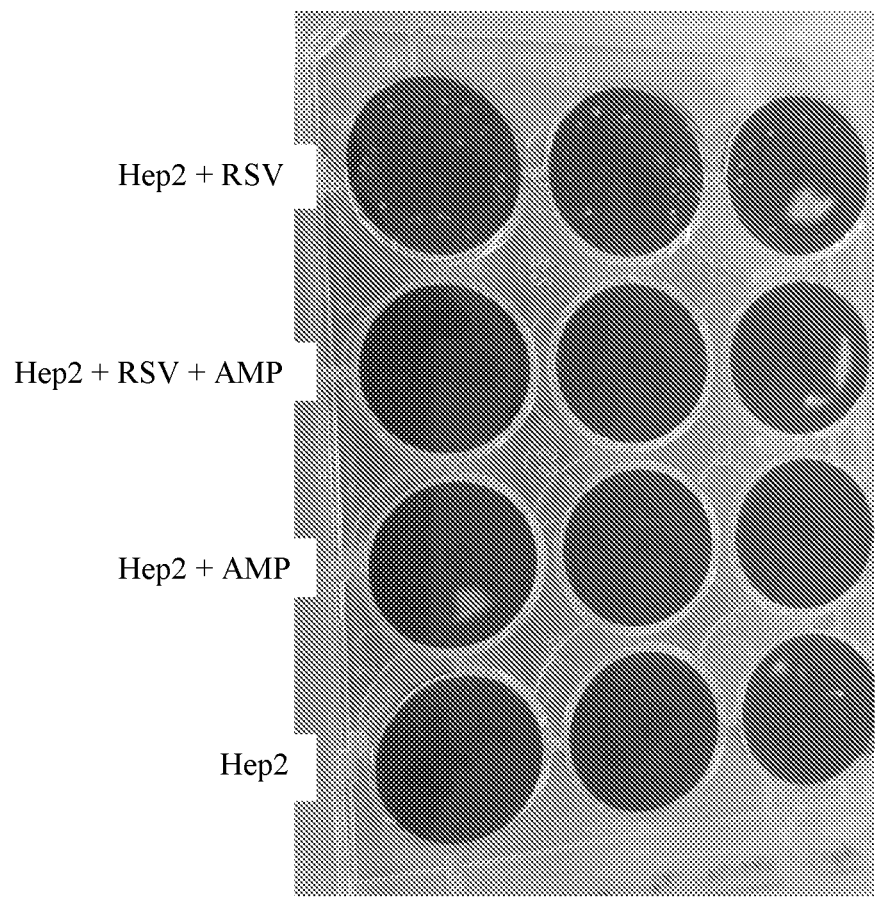

A comparative study between lower doses (4 μM and 16 μM) shows a reduced cytopathic effect and further demonstrated reduced viral plaques in cells treated with 16 μM dosage. Hep2 cells infected with 4 μM dosage of AMP SEQ ID No. 15 (FIG. 19A) reduced the number of plaques when compared to the AMP negative control cells. Wells treated with 16 μM (FIG. 19B) displayed extensively reduced plaque formation when compared to the negative control and the 4 μM dosage. This is visible in the images of FIGS. 19A and 19B, second row of wells.

Figure 20:
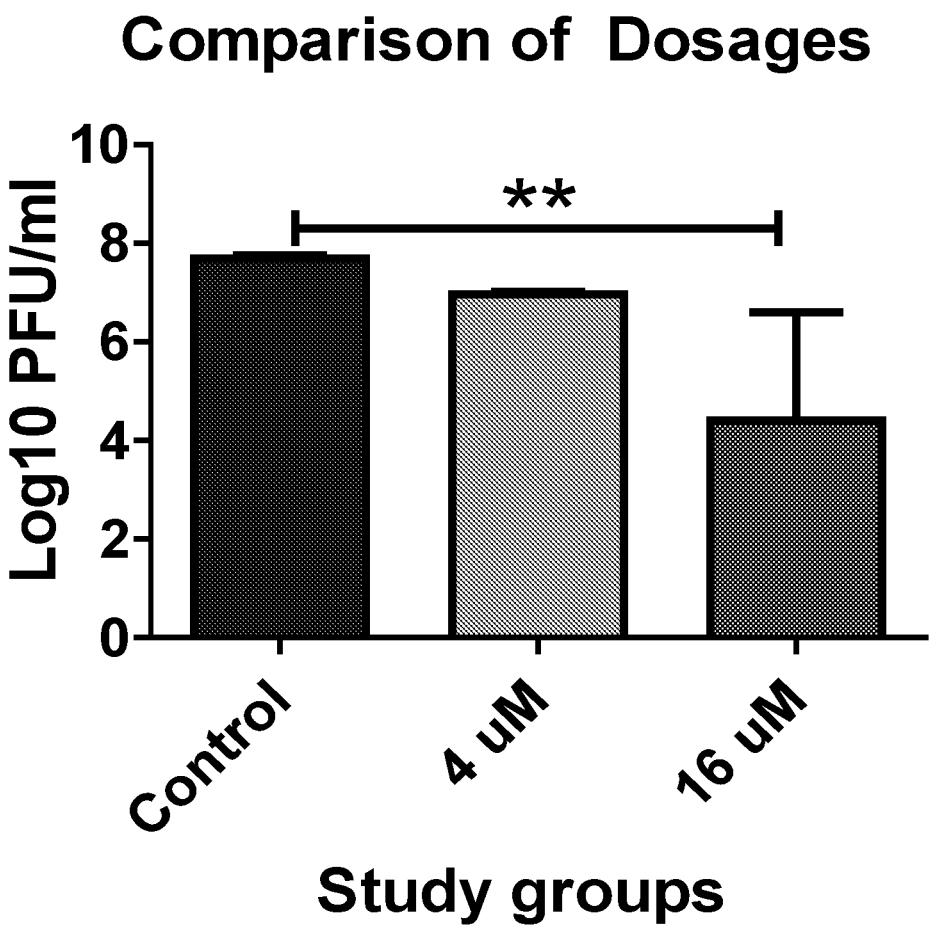
FIG. 20 depicts the log difference between the plaque formation in the 4 µM and 16 µM AMP SEQ ID No. 15 dosage groups compared to the control group.

Viral Plaque quantification shows approximately a 3 log difference between the plaques in the negative control group and the 16 μM dosage group, and only a 1 log difference in 4 μM group. FIG. 20.

Conclusion: We have successfully identified that AMP SEQ ID No. 15 effectively reduces viral titers in RSV-infected Hep2 cells without apparent cytopathology. Hep2 cells treated with 32 μM dosage of different AMP formulations were washed away during the staining process—indicating that this dosage is too high and causes cytotoxicity. At lower dosages of AMP SEQ ID No. 15, there was no cytotoxic effect on the Hep2 cells as can be observed in RSV negative control wells. A 4 μM concentration of AMP SEQ ID No. 15 is not cytotoxic, but fails to significantly reduce viral titers. A 16 μM concentration of AMP SEQ ID No. 15 almost entirely eliminated viral plaques and produced a 3 log reduction in viral plaques when compared to the control. Further studies are needed to optimize dose and duration of the AMP treatment to maximize anti-viral activity while preserving cellular integrity. Many other aforementioned AMPs, not yet tested, are predicted to display antiviral properties as well.

Future studies will include safety and efficacy studies in an RSV-infected animal model.

Example 8

Anti-Cancer Activity

The antitumor properties of AMPs derived from animals based on two sets of mechanisms, selective plasma membrane disruption or non-membranolytic cytotoxicity were examined.

Figure 21A:
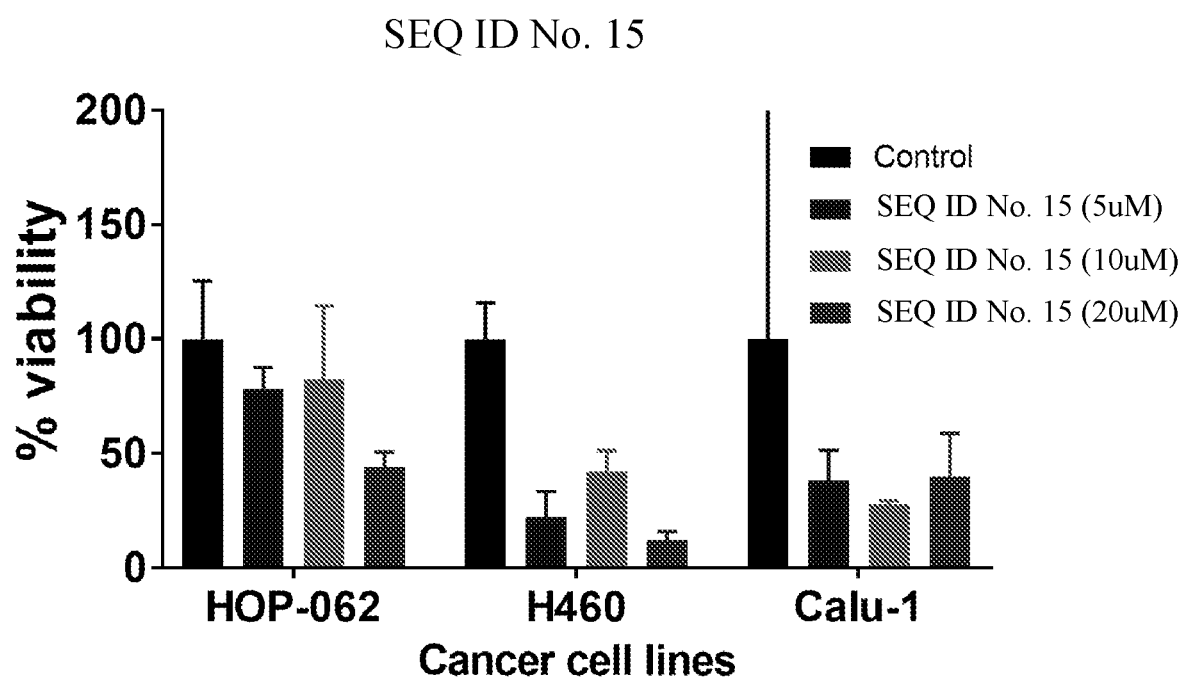
FIG. 21A depicts the anti-cancer activity of AMP SEQ ID No. 15.
Figure 21B:
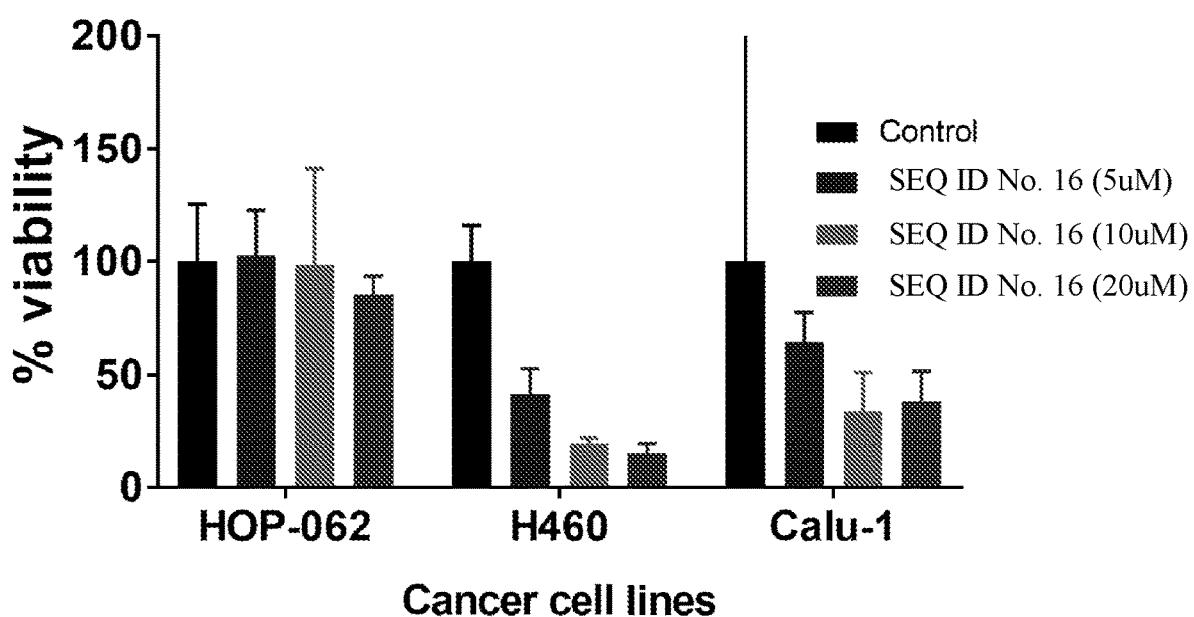
FIG. 21B depicts the anti-cancer activity of AMP SEQ ID No. 16.
Figure 21C:
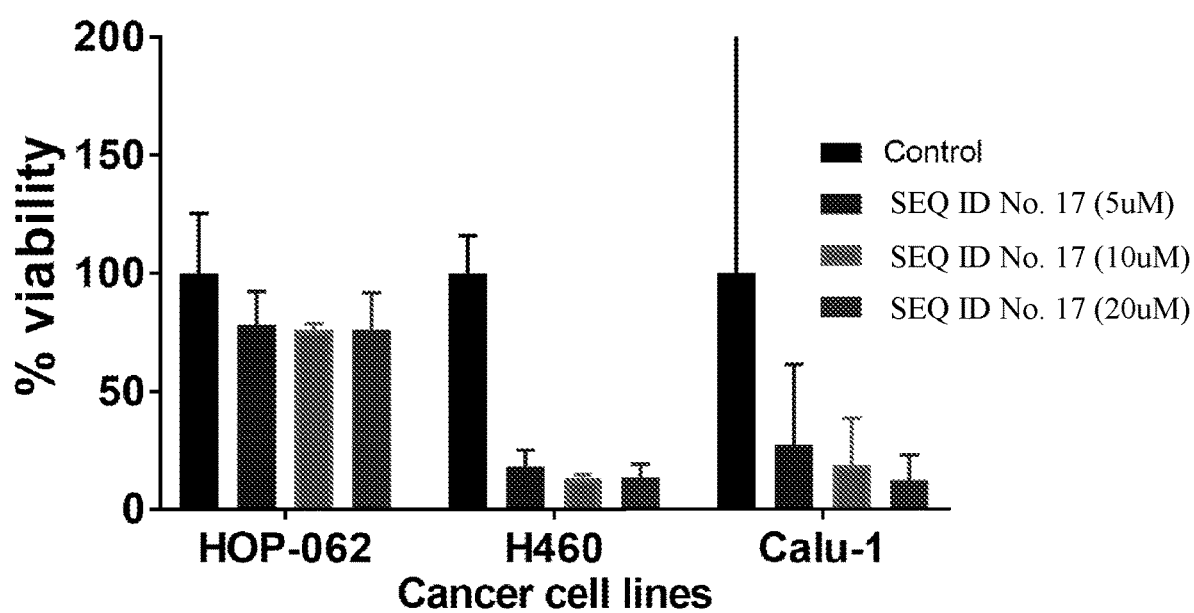
FIG. 21C depicts the anti-cancer activity of AMP SEQ ID No. 17.

Three A4 peptides (see FIG. 21A for SEQ ID No. 15, FIG. 21B for SEQ ID No. 16, and FIG. 21C for SEQ ID No. 17) were examined for anti-cancer activities using three different human cancer cell lines of the respiratory system: HOP-062 (lung adenocarcinoma), H460 (large cell lung cancer), and Calu-1 (non-small cell lung cancer). The cells were grown to 80% confluence and then treated with each A4 AMP for 2 h. Percent viability was examined using a tetrazolium-based assay assessing the mitochondrial integrity. The peptides were highly active against the cancer cell lines with differential selectivity depending on the peptide: SEQ ID No. 15 and 16, most selective toward H460; SEQ ID No. 17, most selective toward both H460 and Calu-1. HOP-062 was relatively resistant to the peptides, with only SEQ ID No. 15 displaying >50% toxicity at 20 µM.

Figure 22A:
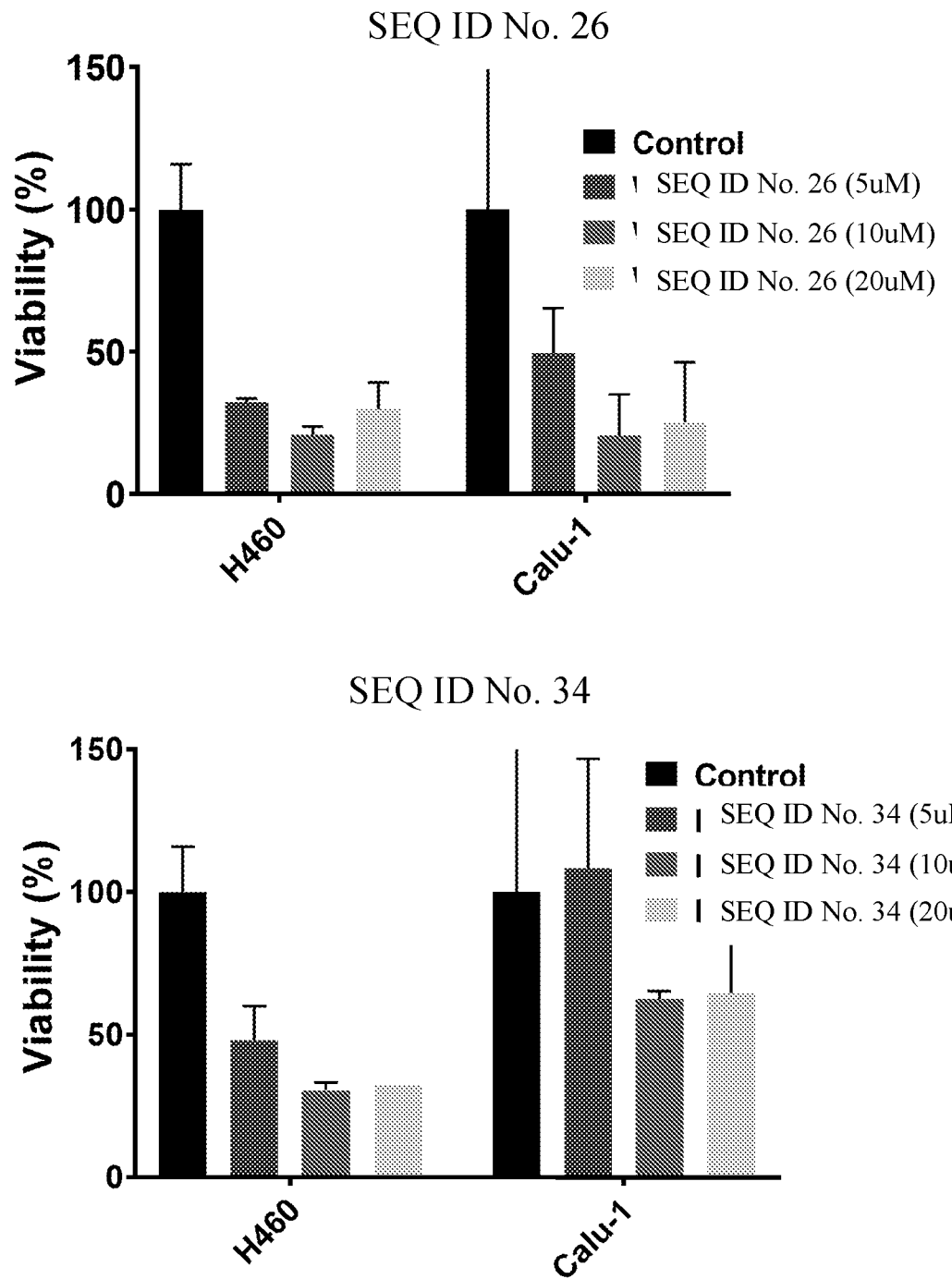
FIG. 22A depicts the anti-cancer activity of SEQ ID No. 26 and its D-amino acid modified enantiomers, SEQ ID No. 34, in H460 (large cell lung cancer) and Calu-1 (non-small cell lung cancer) cell lines.
Figure 22B:
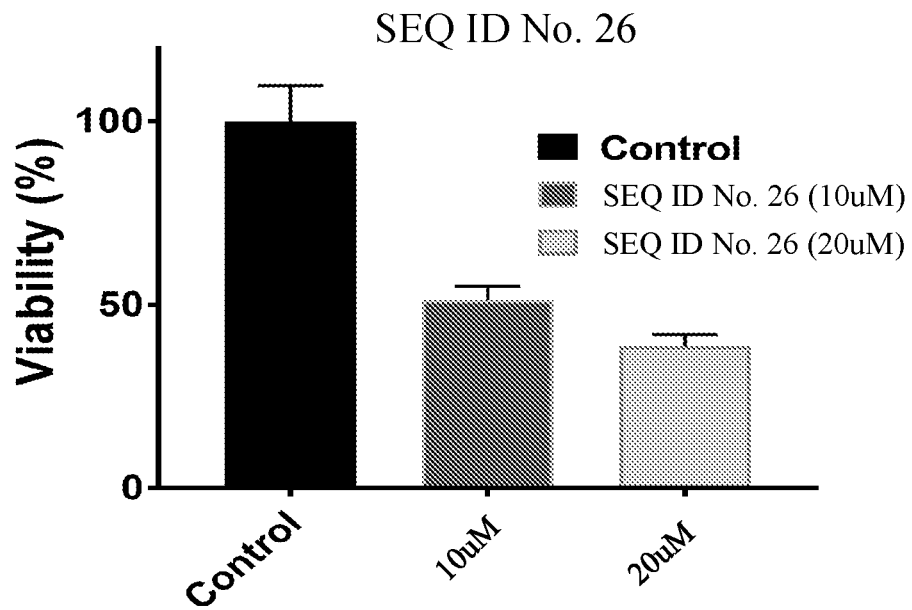
FIG. 22B depicts the anti-cancer activity of SEQ ID No. 26 and its D-amino acid modified enantiomers, SEQ ID No. 34, in primary Human bronchial epithelial (HBE) cells.
Figure 22B:
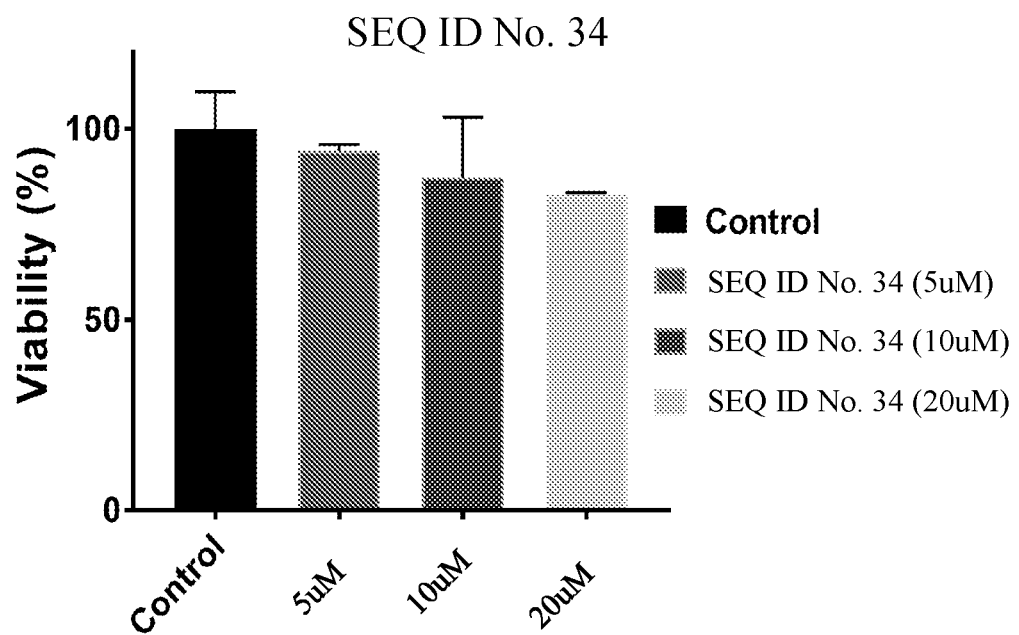

Anti-cancer activity of SEQ ID No. 26 and its D-amino acid modified enantiomer, SEQ ID. No. 34. SEQ ID. No. 34 was compared to SEQ ID No. 26 for selective anti-cancer activities using cancer cell lines of the respiratory system. See FIG. 22A for H460 (large cell lung cancer) and Calu-1 (non-small cell lung cancer) and FIG. 22B for primary Human bronchial epithelial (HBE) cells. The cells were grown to 80% confluence and then treated with each AMP for 2 h. Percent viability was examined using a tetrazolium-based assay assessing the mitochondrial integrity. SEQ ID No. 26 was more active against the cancer cells than SEQ ID. No. 34; however SEQ ID. No. 26 was also toxic to primary HBE cells, in contrast to SEQ ID. No. 34. Therefore, SEQ ID. No. 34 is more selectively anti-tumorous than SEQ ID. No. 26.

Example 9

Anti-TB Activity

Figure 23:
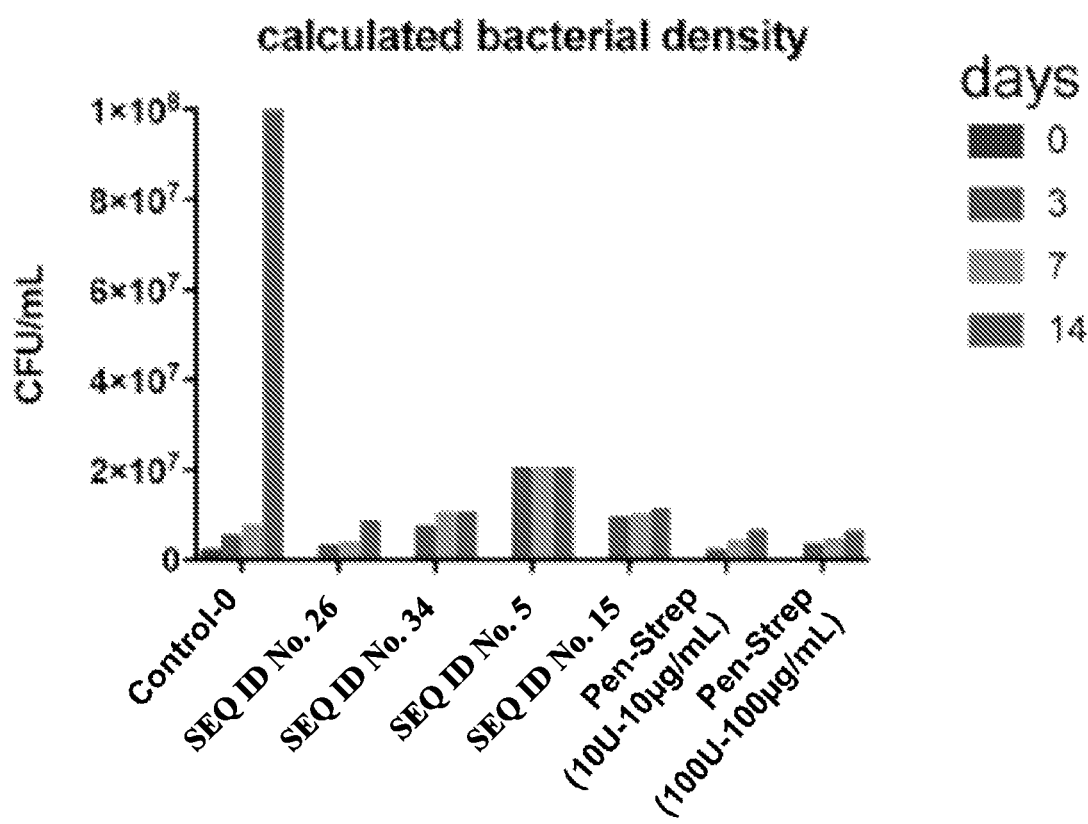
FIG. 23 depicts the comparative anti-TB activities of SEQ ID No. 26, SEQ ID No. 34, SEQ ID No. 5, SEQ ID No. 15, and penicillin/Streptomycin (Pen/Strep) over 14 days.

Data demonstrating the anti-TB activities of SEQ ID. No. 26, SEQ ID. No. 34, SEQ ID. No. 5, SEQ ID. No. 15, and penicillin/Streptomycin (Pen/Strep) in provided in FIG. 23. *Mycobacterium tuberculosis* (MTB) was treated with each peptide [40 uM in 200 uL culture] or PBS and CFU determined after days 0, 3, 7, and 14 (left). The anti-TB activities of the AMPs was more noticeable after MTB was grown for 14 days.

Although the present invention has been described in considerable detail with reference to certain preferred embodiments thereof, other versions are possible. Therefore, the spirit and scope of the appended claims should not be limited to the description and the preferred versions contained within this specification.

Example 10

Low In Vivo Activity

Figure 30:
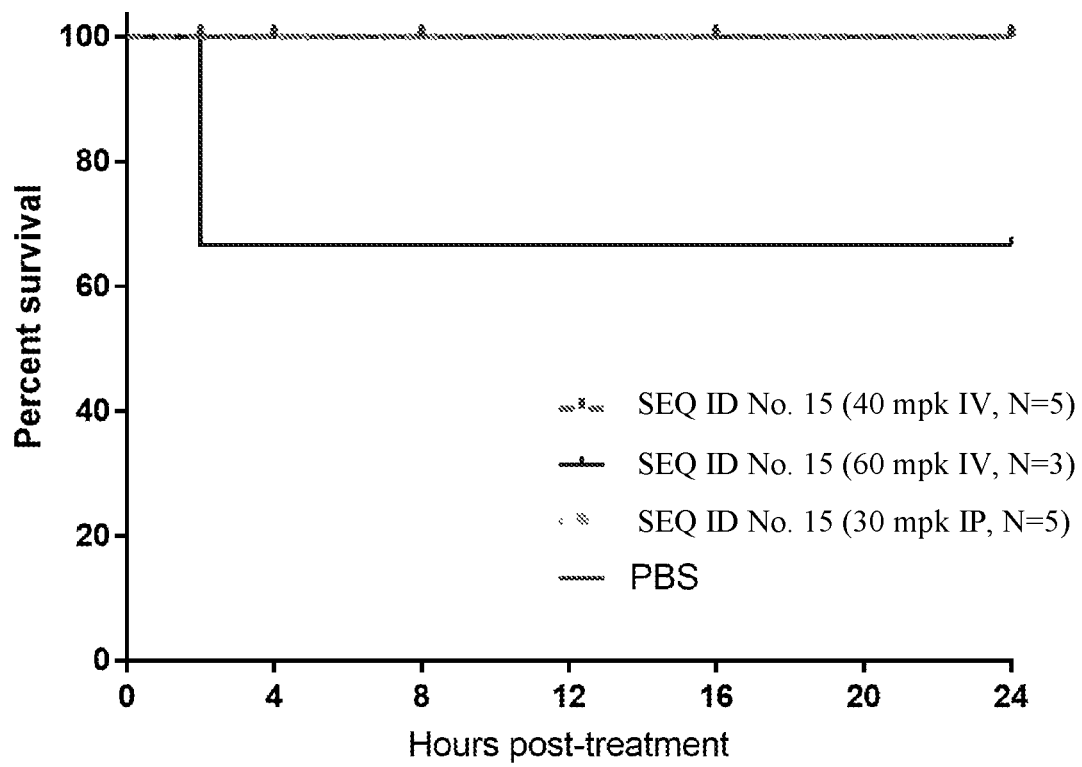
FIG. 30 shows that SEQ ID No. 15 has very low in vivo toxicity.

Mice (strain: Swiss Webster) were injected with SEQ ID No. 15 peptides intravenously (i.v.) or intraperitoneally (i.p.) at the concentrations indicated. One mouse injected with 60 mg/kg (mpk, i.v.) died but all mice were active and tolerated the dosage at 40 mpk (i.v.) and 30 mpk (i.p.). See FIG. 30. Thus, the estimated maximum tolerated dose (MTD) is around 40-50 mpk (i.v.). On a similar setting of testing other AMPS, the MTD for WLBU2 is 15 mpk (i.v.) and 10 mpk (i.v.) for colistin.

AMP Efficacy Against *Pseudomonas aeruginosa*-Induced Septicemia

Figure 31:
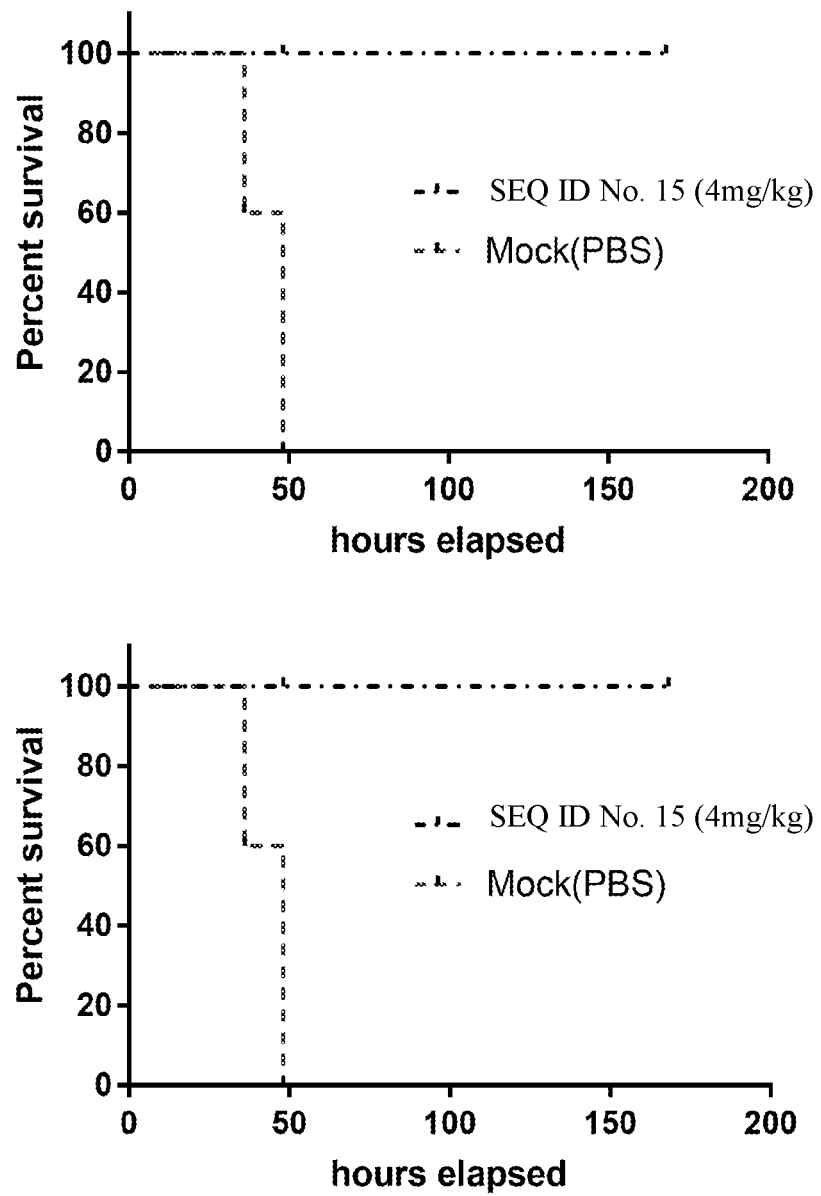
FIG. 31 demonstrates that SEQ ID No. 15 has excellent efficacy against *Pseudomonas aeruginosa*-induced Septicemia.

The administration of 4 mg/kg of SEQ ID No. 15 at 1 hour after high dose bacterial infection (*P. aeruginosa* strain PAO1, $2\times10^7$ CFU) using two different animal models demonstrated 100% protection of bacteria infected mice while all mice treated with phosphate buffer saline (PBS) control died. Swiss Webster mice were infected intravenously (i.v.), N=5 mice per group, p<0.0001, see FIG. 31 top. CD-1 mice were infected intraperitoneally (i.p.), N=6 in mock group and N=9 in test group, see FIG. 31 bottom.

AMP Decreases Host Bacterial Burden in a Sepsis Animal Model Induced by *Pseudomonas aeruginosa* (i.p.)

Figure 32:
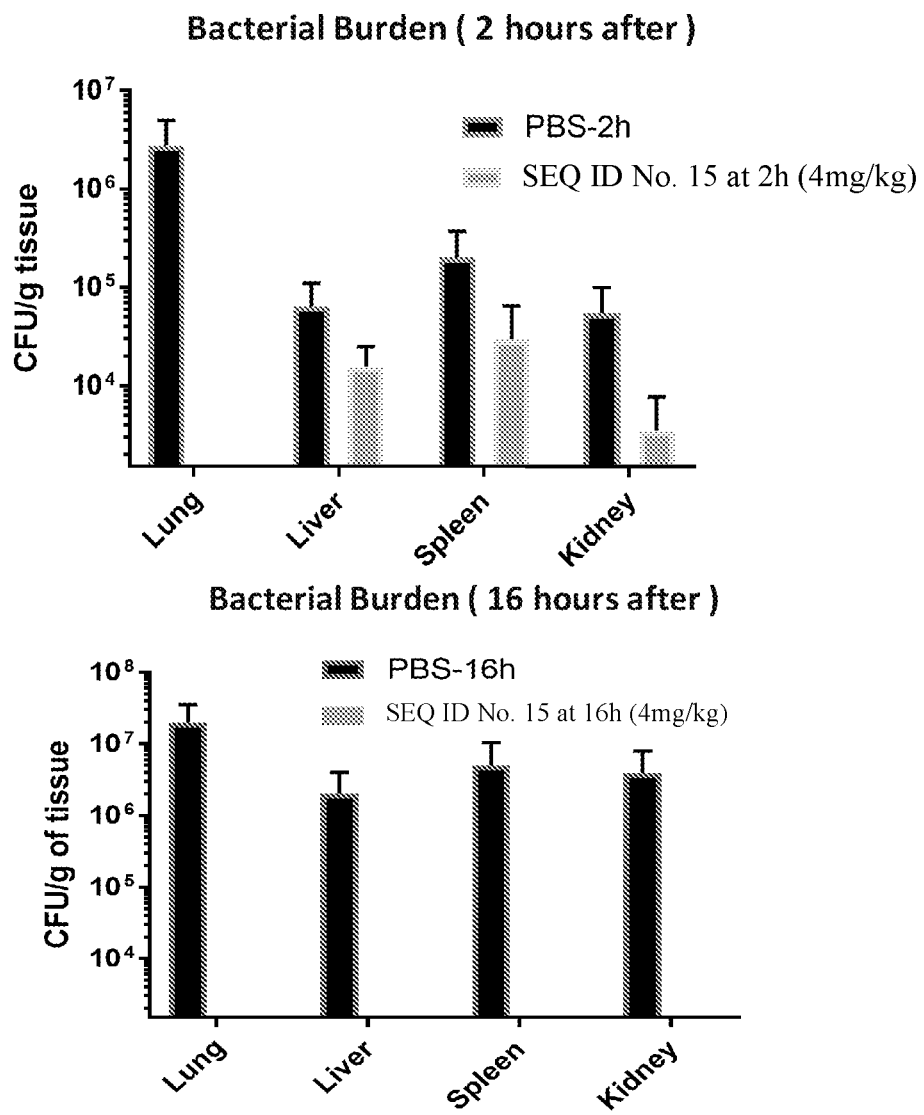
FIG. 32 shows that SEQ ID No. 15 decreases host bacterial burden in a sepsis animal model induced by *Pseudomonas aeruginosa* (i.p.).

Bacterial burden in multiple organs of *Pseudomonas aeruginosa* (PAO1, ~$1\times10^7$ CFU, i.p.) infected mice was determined at 2 hours and 16 hours after the intravenous (i.v.) administration with either SEQ ID No. 15 (4 mpk) or PBS, treatment was performed at one hour post infection. There was significantly less bacterial burden in antimicrobial peptide treated group of mice at 2 hours after the SEQ ID No. 15 administration (p=0.005) when compared with PBS treatment group. See FIG. 32 top, N=5 in PBS group and N=5 in test group. At 16 hours after the treatment, there was no bacteria detected in different organs of the SEQ ID No. 15-treated group while the bacterial burden further increased in PBS-treated group of mice. See FIG. 32 bottom, N=4 in PBS group and N=6 in test group. The data suggests that the administration of SEQ ID No. 15 effectively eliminated *Pseudomonas aeruginosa* infection that otherwise would result in bacterial infection-induced multi-organ failure and death.

---

The invention claimed is:

1. A method of treating a microbial infection in a subject in need thereof comprising administering to the subject a therapeutically effective amount of a composition comprising one or more antimicrobial peptides (AMPs) comprising a helical amphipathic structure provided in formula I: wherein the formula I numbering refers to an order of 18 contiguous amino acid residues within the AMPs from an N-terminal to a C-terminal direction and wherein amino acid residues 1, 4, 5, 8, 11, 12, 15, and 16 are hydrophobic amino acids, and amino acid residues 2, 3, 6, 7, 9, 10, 13, 14, 17, and 18 are any non-hydrophobic or hydrophilic amino acids, wherein the one or more AMPs comprise a sequence selected from the group consisting of ILKKWWββαβGLLGβLLGαVββVIKβLββI (SEQ ID NO 2), LKKWWKβαKGLLGGLLGKVββVIK (SEQ ID NO 12), and αKKααKKαKGαLGGLαGK (SEQ ID NO 18) wherein α is a hydrophobic amino acid selected from the group consisting of the L or D form of the following: alanine, isoleucine, leucine, tryptophan, phenylalanine, valine, proline, and glycine and wherein β is a non-hydrophobic or hydrophilic amino acid selected from the group consisting of the L or D form of the following: arginine, lysine, aspartic acid, glutamic acid, glutamine, asparagine, histidine, serine, threonine, tyrosine, cysteine, methionine, selenocysteine, and pyrrolysine, wherein the microbial infection is caused by a microbe selected from the group consisting of *Enterococcus faecium, Staphylococcus aureus, Klebsiella pneumonia, Pseudomonas aeruginosa, Mycobacterium tuberculosis, Escherichia coli*, Enterobacteriaceae, *Acinetobacter baumannii*, and respiratory syncytial virus.

2. The method of claim 1, wherein a valine is substituted with the D-amino acid version.

3. The method of claim 1, wherein the one or more AMPs are administered in an amount of about 1 mg/kg to about 150 mg/kg.

4. The method of claim 1, further comprising administering an antibiotic with the one or more AMPs.

5. The method of claim 4, wherein the antibiotic is selected from the group consisting of penicillin, cephalosporin, vancomycin, polymyxin, rifamycin, lipiarmycin, quinolone, sulfonamide, macrolide, lincosamide, tetracycline, cyclic lipopeptides, glycylcyclines, oxazolidinones, and lipiarmycins.

6. The method of claim 1, wherein the microbial infection is caused by the respiratory syncytial virus.

7. The method of claim 1, wherein the microbial infection is caused by *Mycobacterium tuberculosis*.

8. The method of claim 1, wherein administering the therapeutically effective amount of the one or more AMPs reduces a biofilm in the subject.

9. The method of claim 1, wherein administering the therapeutically effective amount of the one or more AMPs decreases inflammation in the subject.

10. The method of claim 1, wherein administering the therapeutically effective amount of the one or more AMPs treats chronic obstructive pulmonary disease (COPD), asthma, pulmonary fibrosis, cystic fibrosis, septicemia, rhinosinusitis, or tuberculosis.

11. The method of claim 1, wherein the one or more AMPs comprise the sequence of LKKWWKKVKGLLGGLLGKVTSVIK (SEQ ID NO 15).

* * * * *

SEQUENCE LISTING

```
<160> NUMBER OF SEQ ID NOS: 34

<210> SEQ ID NO 1
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 1

Ile Leu Lys Pro Gly Gly Gly Thr Ser Gly Gly Leu Leu Gly Gly Leu
```

Leu Gly Lys Val Thr Ser Val Ile Pro Gly Leu Asn Asn Ile
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is non-hydrophobic or hydrophilic amino
    acid
<220> FEATURE:
<221> NAME/KEY: MISC_FEATURE
<222> LOCATION: (8)..(8)
<223> OTHER INFORMATION: Xaa is non-hydrophobic or hydrophilic amino
    acid
<220> FEATURE:
<221> NAME/KEY: MISC_FEATURE
<222> LOCATION: (9)..(9)
<223> OTHER INFORMATION: Xaa is hydrophobic amino acid
<220> FEATURE:
<221> NAME/KEY: MISC_FEATURE
<222> LOCATION: (10)..(10)
<223> OTHER INFORMATION: Xaa is non-hydrophobic or hydrophilic amino
    acid
<220> FEATURE:
<221> NAME/KEY: MISC_FEATURE
<222> LOCATION: (15)..(15)
<223> OTHER INFORMATION: Xaa is non-hydrophobic or hydrophilic amino
    acid
<220> FEATURE:
<221> NAME/KEY: MISC_FEATURE
<222> LOCATION: (19)..(19)
<223> OTHER INFORMATION: Xaa is hydrophobic amino acid
<220> FEATURE:
<221> NAME/KEY: MISC_FEATURE
<222> LOCATION: (21)..(21)
<223> OTHER INFORMATION: Xaa is non-hydrophobic or hydrophilic amino
    acid
<220> FEATURE:
<221> NAME/KEY: MISC_FEATURE
<222> LOCATION: (22)..(22)
<223> OTHER INFORMATION: Xaa is non-hydrophobic or hydrophilic amino
    acid
<220> FEATURE:
<221> NAME/KEY: MISC_FEATURE
<222> LOCATION: (26)..(26)
<223> OTHER INFORMATION: Xaa is non-hydrophobic or hydrophilic amino
    acid
<220> FEATURE:
<221> NAME/KEY: MISC_FEATURE
<222> LOCATION: (28)..(28)
<223> OTHER INFORMATION: Xaa is non-hydrophobic or hydrophilic amino
    acid
<220> FEATURE:
<221> NAME/KEY: MISC_FEATURE
<222> LOCATION: (29)..(29)
<223> OTHER INFORMATION: Xaa is non-hydrophobic or hydrophilic amino
    acid

<400> SEQUENCE: 2

Ile Leu Lys Lys Trp Trp Xaa Xaa Xaa Xaa Gly Leu Leu Gly Xaa Leu
1               5                   10                  15
Leu Gly Xaa Val Xaa Xaa Val Ile Lys Xaa Leu Xaa Xaa Ile
            20                  25                  30

<210> SEQ ID NO 3
<211> LENGTH: 30
<212> TYPE: PRT
<213> ORGANISM: Artificial Sequence

```
<220> FEATURE:
<223> OTHER INFORMATION: Synthetic Peptide

<400> SEQUENCE: 3

Ile Leu Lys Lys Trp Trp Gly Thr Ser Gly Gly Leu Leu Gly Gly Leu
1               5                   10                  15

Leu Gly Lys Val Thr Ser Val Ile Lys Gly Leu Asn Asn Ile
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 4

Ile Leu Lys Lys Trp Trp Lys Thr Ser Gly Gly Leu Leu Gly Gly Leu
1               5                   10                  15

Leu Gly Lys Val Thr Ser Val Ile Lys Gly Leu Asn Asn Ile
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 5

Ile Leu Lys Lys Trp Trp Lys Thr Ser Lys Gly Leu Leu Gly Gly Leu
1               5                   10                  15

Leu Gly Lys Val Thr Ser Val Ile Lys Gly Leu Asn Asn Ile
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 6

Ile Leu Lys Lys Trp Trp Lys Thr Ser Lys Gly Leu Leu Gly Gly Leu
1               5                   10                  15

Leu Gly Lys Val Thr Ser Val Ile Lys Gly Leu Lys Asn Ile
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 7

Ile Leu Lys Lys Trp Trp Lys Thr Ser Lys Gly Leu Leu Gly Gly Leu
1               5                   10                  15

Leu Gly Gly Val Thr Ser Val Ile Lys Lys Leu Lys Lys Ile
            20                  25                  30

<210> SEQ ID NO 8
<211> LENGTH: 30
<212> TYPE: PRT
```

```
<213> ORGANISM: Artificial Sequence
<220> FEATURE:
<223> OTHER INFORMATION: Synthetic Peptide

<400> SEQUENCE: 8

Ile Leu Lys Lys Trp Trp Lys Thr Ser Lys Gly Leu Leu Gly Gly Leu
1               5                   10                  15

Leu Gly Gly Val Thr Ser Val Ile Lys Lys Leu Lys Lys Ile
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 9

Ile Leu Lys Lys Trp Trp Lys Thr Val Lys Gly Leu Leu Gly Gly Leu
1               5                   10                  15

Leu Gly Gly Val Thr Ser Val Ile Lys Lys Leu Lys Lys Ile
            20                  25                  30

<210> SEQ ID NO 10
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 10

Ile Leu Lys Lys Trp Trp Lys Lys Val Lys Gly Leu Leu Gly Lys Leu
1               5                   10                  15

Leu Gly Gly Val Lys Ser Val Ile Lys Gly Leu Asn Asn Ile
            20                  25                  30

<210> SEQ ID NO 11
<211> LENGTH: 30
<212> TYPE: PRT
<213> ORGANISM: Artificial Sequence
<220> FEATURE:
<223> OTHER INFORMATION: Synthetic Peptide

<400> SEQUENCE: 11

Ile Leu Lys Lys Trp Trp Lys Lys Val Lys Gly Leu Leu Gly Lys Leu
1               5                   10                  15

Leu Gly Gly Val Lys Lys Val Ile Lys Gly Leu Asn Asn Ile
            20                  25                  30

<210> SEQ ID NO 12
<211> LENGTH: 24
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is non-hydrophobic or hydrophilic amino
      acid
<220> FEATURE:
<221> NAME/KEY: MISC_FEATURE
<222> LOCATION: (8)..(8)
<223> OTHER INFORMATION: Xaa is hydrophobic amino acid
<220> FEATURE:
<221> NAME/KEY: MISC_FEATURE
<222> LOCATION: (20)..(20)
```

```
<223> OTHER INFORMATION: Xaa is non-hydrophobic or hydrophilic amino
      acid
<220> FEATURE:
<221> NAME/KEY: MISC_FEATURE
<222> LOCATION: (21)..(21)
<223> OTHER INFORMATION: Xaa is non-hydrophobic or hydrophilic amino
      acid

<400> SEQUENCE: 12

Leu Lys Lys Trp Trp Lys Xaa Xaa Lys Gly Leu Leu Gly Gly Leu Leu
1               5                   10                  15

Gly Lys Val Xaa Xaa Val Ile Lys
            20

<210> SEQ ID NO 13
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 13

Leu Lys Lys Trp Trp Lys Thr Ser Lys Gly Leu Leu Gly Gly Leu Leu
1               5                   10                  15

Gly Lys Val Thr Ser Val Ile Lys
            20

<210> SEQ ID NO 14
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 14

Leu Lys Lys Trp Trp Lys Thr Val Lys Gly Leu Leu Gly Gly Leu Leu
1               5                   10                  15

Gly Lys Val Thr Ser Val Ile Lys
            20

<210> SEQ ID NO 15
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 15

Leu Lys Lys Trp Trp Lys Lys Val Lys Gly Leu Leu Gly Gly Leu Leu
1               5                   10                  15

Gly Lys Val Thr Ser Val Ile Lys
            20

<210> SEQ ID NO 16
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 16

Leu Lys Lys Trp Trp Lys Lys Val Lys Gly Leu Leu Gly Gly Leu Leu
1               5                   10                  15

Gly Lys Val Lys Ser Val Ile Lys
            20
```

```
<210> SEQ ID NO 17
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 17

Leu Lys Lys Trp Trp Lys Lys Val Lys Gly Leu Leu Gly Gly Leu Leu
1               5                   10                  15

Gly Lys Val Lys Lys Val Ile Lys
            20

<210> SEQ ID NO 18
<211> LENGTH: 18
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa is hydrophobic amino acid
<220> FEATURE:
<221> NAME/KEY: MISC_FEATURE
<222> LOCATION: (4)..(4)
<223> OTHER INFORMATION: Xaa is hydrophobic amino acid
<220> FEATURE:
<221> NAME/KEY: MISC_FEATURE
<222> LOCATION: (5)..(5)
<223> OTHER INFORMATION: Xaa is hydrophobic amino acid
<220> FEATURE:
<221> NAME/KEY: MISC_FEATURE
<222> LOCATION: (8)..(8)
<223> OTHER INFORMATION: Xaa is hydrophobic amino acid
<220> FEATURE:
<221> NAME/KEY: MISC_FEATURE
<222> LOCATION: (11)..(11)
<223> OTHER INFORMATION: Xaa is hydrophobic amino acid
<220> FEATURE:
<221> NAME/KEY: MISC_FEATURE
<222> LOCATION: (16)..(16)
<223> OTHER INFORMATION: Xaa is hydrophobic amino acid

<400> SEQUENCE: 18

Xaa Lys Lys Xaa Xaa Lys Lys Xaa Lys Gly Xaa Leu Gly Gly Leu Xaa
1               5                   10                  15

Gly Lys

<210> SEQ ID NO 19
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 19

Leu Lys Lys Trp Trp Lys Lys Val Lys Gly Leu Leu Gly Gly Leu Leu
1               5                   10                  15

Gly Lys

<210> SEQ ID NO 20
<211> LENGTH: 18
<212> TYPE: PRT
<213> ORGANISM: Artificial Sequence
<220> FEATURE:
<223> OTHER INFORMATION: Synthetic Peptide
```

```
<400> SEQUENCE: 20

Leu Lys Lys Leu Leu Lys Lys Val Lys Gly Trp Leu Gly Gly Leu Trp
1               5                   10                  15

Gly Lys

<210> SEQ ID NO 21
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 21

Val Lys Lys Leu Leu Lys Lys Val Lys Gly Trp Leu Gly Gly Leu Trp
1               5                   10                  15

Gly Lys

<210> SEQ ID NO 22
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 22

Gly Lys Lys Leu Leu Lys Lys Val Lys Gly Trp Leu Gly Gly Leu Trp
1               5                   10                  15

Gly Lys

<210> SEQ ID NO 23
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 23

Gly Lys Lys Leu Leu Lys Lys Gly Lys Gly Trp Leu Gly Gly Leu Trp
1               5                   10                  15

Gly Lys

<210> SEQ ID NO 24
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 24

Gly Val Lys Lys Lys Trp Lys Lys Lys Leu Gly Leu Lys Leu Trp Leu
1               5                   10                  15

Lys Ile Ser Gly Val Val Leu Gly
            20

<210> SEQ ID NO 25
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 25

Leu Leu Gly Asp Phe Phe Arg Lys Ser Lys Glu Lys Ile Gly Lys Glu
```

-continued

```
                 1               5                  10                 15
Phe Lys Arg Ile Val Gln Arg Ile Lys Asp Phe Leu Arg Asn Leu Leu
             20                  25                 30
Pro Arg Thr Glu Ser
        35

<210> SEQ ID NO 26
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 26

Arg Arg Trp Val Arg Val Arg Arg Val Trp Arg Arg Val Val Arg
1               5                   10                  15

Val Val Arg Arg Trp Val Arg Arg
            20

<210> SEQ ID NO 27
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 27

Lys Leu Trp Lys Lys Gly Lys Gly Gly Lys Leu Thr Lys Ser Leu Thr
1               5                   10                  15

Trp Val Leu Val Gly Ile Leu Val
            20

<210> SEQ ID NO 28
<211> LENGTH: 18
<212> TYPE: PRT
<213> ORGANISM: Artificial Sequence
<220> FEATURE:
<223> OTHER INFORMATION: Synthetic Peptide

<400> SEQUENCE: 28

Val Trp Lys Trp Gly Lys Leu Gly Lys Leu Leu Lys Leu Gly Lys Leu
1               5                   10                  15

Gly Lys

<210> SEQ ID NO 29
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 29

Lys Lys Leu Gly Lys Lys Val Val Gly Lys Leu Gly Thr Ser Lys Val
1               5                   10                  15

Trp Lys Leu Ile Gly Trp Leu Leu
            20

<210> SEQ ID NO 30
<211> LENGTH: 24
<212> TYPE: PRT
<213> ORGANISM: Artificial Sequence
<220> FEATURE:
<223> OTHER INFORMATION: Synthetic Peptide
```

<400> SEQUENCE: 30

Leu Lys Lys Trp Trp Lys Lys Val Leu Gly Leu Leu Gly Gly Leu Lys
1               5                   10                  15

Gly Lys Val Thr Ser Val Ile Lys
            20

<210> SEQ ID NO 31
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 31

Leu Lys Lys Trp Leu Lys Lys Val Leu Gly Leu Lys Gly Gly Leu Trp
1               5                   10                  15

Gly Lys Val Thr Ser Val Ile Lys
            20

<210> SEQ ID NO 32
<211> LENGTH: 24
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is D-valine
<220> FEATURE:
<221> NAME/KEY: MISC_FEATURE
<222> LOCATION: (15)..(15)
<223> OTHER INFORMATION: Xaa is D-valine
<220> FEATURE:
<221> NAME/KEY: MISC_FEATURE
<222> LOCATION: (17)..(17)
<223> OTHER INFORMATION: Xaa is D-valine
<220> FEATURE:
<221> NAME/KEY: MISC_FEATURE
<222> LOCATION: (22)..(22)
<223> OTHER INFORMATION: Xaa is D-valine

<400> SEQUENCE: 32

Arg Arg Trp Val Arg Arg Xaa Arg Arg Val Trp Arg Arg Val Xaa Arg
1               5                   10                  15

Xaa Val Arg Arg Trp Xaa Arg Arg
            20

<210> SEQ ID NO 33
<211> LENGTH: 24
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is D-valine
<220> FEATURE:
<221> NAME/KEY: MISC_FEATURE
<222> LOCATION: (10)..(10)
<223> OTHER INFORMATION: Xaa is D-valine
<220> FEATURE:
<221> NAME/KEY: MISC_FEATURE
<222> LOCATION: (15)..(15)
<223> OTHER INFORMATION: Xaa is D-valine
<220> FEATURE:
<221> NAME/KEY: MISC_FEATURE
<222> LOCATION: (17)..(17)
<223> OTHER INFORMATION: Xaa is D-valine

```
<220> FEATURE:
<221> NAME/KEY: MISC_FEATURE
<222> LOCATION: (18)..(18)
<223> OTHER INFORMATION: Xaa is D-valine
<220> FEATURE:
<221> NAME/KEY: MISC_FEATURE
<222> LOCATION: (22)..(22)
<223> OTHER INFORMATION: Xaa is D-valine

<400> SEQUENCE: 33

Arg Arg Trp Val Arg Arg Xaa Arg Arg Xaa Trp Arg Arg Val Xaa Arg
1               5                   10                  15

Xaa Xaa Arg Arg Trp Xaa Arg Arg
            20

<210> SEQ ID NO 34
<211> LENGTH: 24
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (4)..(4)
<223> OTHER INFORMATION: Xaa is D-valine
<220> FEATURE:
<221> NAME/KEY: MISC_FEATURE
<222> LOCATION: (7)..(7)
<223> OTHER INFORMATION: Xaa is D-valine
<220> FEATURE:
<221> NAME/KEY: MISC_FEATURE
<222> LOCATION: (10)..(10)
<223> OTHER INFORMATION: Xaa is D-valine
<220> FEATURE:
<221> NAME/KEY: MISC_FEATURE
<222> LOCATION: (14)..(14)
<223> OTHER INFORMATION: Xaa is D-valine
<220> FEATURE:
<221> NAME/KEY: MISC_FEATURE
<222> LOCATION: (15)..(15)
<223> OTHER INFORMATION: Xaa is D-valine
<220> FEATURE:
<221> NAME/KEY: MISC_FEATURE
<222> LOCATION: (17)..(17)
<223> OTHER INFORMATION: Xaa is D-valine
<220> FEATURE:
<221> NAME/KEY: MISC_FEATURE
<222> LOCATION: (18)..(18)
<223> OTHER INFORMATION: Xaa is D-valine
<220> FEATURE:
<221> NAME/KEY: MISC_FEATURE
<222> LOCATION: (22)..(22)
<223> OTHER INFORMATION: Xaa is D-valine

<400> SEQUENCE: 34

Arg Arg Trp Xaa Arg Arg Xaa Arg Arg Xaa Trp Arg Arg Xaa Xaa Arg
1               5                   10                  15

Xaa Xaa Arg Arg Trp Xaa Arg Arg
            20
```